(12) United States Patent
Cabrera Aquino et al.

(10) Patent No.: US 10,245,388 B2
(45) Date of Patent: Apr. 2, 2019

(54) INJECTION DEVICE FOR MINIMALLY INVASIVE PROCEDURES AND USES THEREOF

(71) Applicants: Jose Gustavo Cabrera Aquino, Mexico City (MX); Blanca Angelica Segura Pacheco, Mexico City (MX); Steven Gerken, Encinitas, CA (US); Steven Masterson, Encinitas, CA (US)

(72) Inventors: Jose Gustavo Cabrera Aquino, Mexico City (MX); Blanca Angelica Segura Pacheco, Mexico City (MX); Steven Gerken, Encinitas, CA (US); Steven Masterson, Encinitas, CA (US)

(73) Assignee: Global Bio Therapeutics, Inc., San Diego, CA (US)

( * ) Notice: Subject to any disclaimer, the term of this patent is extended or adjusted under 35 U.S.C. 154(b) by 948 days.

(21) Appl. No.: 14/455,865

(22) Filed: Aug. 8, 2014

(65) Prior Publication Data

US 2015/0045769 A1 Feb. 12, 2015
US 2015/0352293 A9 Dec. 10, 2015

Related U.S. Application Data

(60) Provisional application No. 61/863,888, filed on Aug. 8, 2013.

(51) Int. Cl.
*A61M 5/46* (2006.01)
*A61D 7/00* (2006.01)
(Continued)

(52) U.S. Cl.
CPC .......... *A61M 5/46* (2013.01); *A61B 17/3478* (2013.01); *A61D 7/00* (2013.01); *A61M 5/31511* (2013.01);
(Continued)

(58) Field of Classification Search
CPC .............. A61D 7/00; A61M 2090/034; A61M 2005/31598; A61M 2202/206;
(Continued)

(56) References Cited

U.S. PATENT DOCUMENTS

| 4,763,667 A | 8/1988 | Manzo .......................... 600/563 |
| 5,188,597 A | 2/1993 | Sweeney et al. ............. 604/110 |

(Continued)

FOREIGN PATENT DOCUMENTS

| EP | 2 489 380 | 8/2012 |
| JP | 2000-070336 | 3/2000 |

(Continued)

OTHER PUBLICATIONS

Letter/Written Disclosure of the Information Disclosure Statement for the above-referenced application, mailed on Oct. 26, 2015, 2 pages.

(Continued)

*Primary Examiner* — Brandy S Lee
(74) *Attorney, Agent, or Firm* — Dentons US LLP; Stephanie Seidman

(57) ABSTRACT

Provided herein is an injection device that can be used in minimally invasive procedures, such as laparoscopic surgeries, for direct administration of a fluid, such as a therapeutic, to a target tissue or organ.

52 Claims, 16 Drawing Sheets

(51) Int. Cl.

| | |
|---|---|
| *A61M 5/315* | (2006.01) |
| *A61M 5/32* | (2006.01) |
| *A61B 17/34* | (2006.01) |
| *A61B 17/00* | (2006.01) |
| *A61B 90/00* | (2016.01) |

(52) U.S. Cl.
CPC . *A61M 5/3202* (2013.01); *A61B 2017/00247* (2013.01); *A61B 2090/034* (2016.02); *A61B 2090/08021* (2016.02); *A61M 2005/31598* (2013.01); *A61M 2202/206* (2013.01); *A61M 2210/02* (2013.01); *A61M 2210/04* (2013.01); *A61M 2210/0693* (2013.01); *A61M 2210/1003* (2013.01); *A61M 2210/1039* (2013.01); *A61M 2210/1071* (2013.01); *A61M 2210/1089* (2013.01); *A61M 2210/125* (2013.01); *A61M 2210/1433* (2013.01); *A61M 2210/166* (2013.01)

(58) Field of Classification Search
CPC .......... A61M 2210/02; A61M 2210/04; A61M 2210/0693; A61M 2210/1003; A61M 2210/1039; A61M 2210/1071; A61M 2210/1089; A61M 2210/125; A61M 2210/1433; A61M 2210/166; A61M 5/31511; A61M 5/3202; A61M 5/46; A61B 17/3478; A61B 2017/00247; A61B 2090/034; A61B 2090/08021
See application file for complete search history.

(56) References Cited

U.S. PATENT DOCUMENTS

| | | | |
|---|---|---|---|
| 5,203,786 A | 4/1993 | Vernick | 606/151 |
| 5,300,041 A | 4/1994 | Haber et al. | 604/207 |
| 5,328,470 A | 7/1994 | Nabel et al. | 604/101 |
| 5,486,183 A | 1/1996 | Middleman et al. | 606/127 |
| 5,496,333 A | 3/1996 | Sackier et al. | 227/901 |
| 5,543,328 A | 8/1996 | McClelland et al. | 435/320.1 |
| 5,591,138 A | 1/1997 | Vaillancourt | 604/263 |
| 5,685,853 A | 11/1997 | Bonnet | 604/164 |
| 5,756,086 A | 5/1998 | McClelland et al. | 424/93.2 |
| 5,782,839 A | 7/1998 | Hart et al. | 606/110 |
| 5,785,689 A | 7/1998 | de Toledo et al. | 604/158 |
| 5,993,418 A | 10/1999 | Alexander | 604/110 |
| 6,004,295 A | 12/1999 | Langer et al. | 604/164.01 |
| 6,057,155 A | 5/2000 | Wickham et al. | 435/325 |
| 6,142,088 A | 11/2000 | Beyer | 112/222 |
| 6,309,375 B1 | 10/2001 | Glines et al. | 604/187 |
| 6,322,536 B1 | 11/2001 | Rosengart et al. | 604/164.01 |
| 6,723,082 B1 | 4/2004 | Payne et al. | 604/528 |
| 6,743,206 B1 | 6/2004 | Smith et al. | 604/164.01 |
| 6,821,264 B1 | 11/2004 | Khurana et al. | 604/46 |
| 7,462,592 B2 | 12/2008 | Zuckermann et al. | 514/2 |
| 8,337,468 B1 | 5/2012 | Reis et al. | 604/181 |
| 8,328,560 B2 | 12/2012 | Niblock et al. | 434/262 |
| 2004/0053875 A1 | 3/2004 | Kreutzer | 514/44 |
| 2005/0129660 A1 | 6/2005 | Hagstrom et al. | 424/93.2 |
| 2005/0261634 A1 | 11/2005 | Karlsson | 604/197 |
| 2006/0025749 A1 | 2/2006 | Moenning | 604/506 |
| 2006/0200083 A1 | 9/2006 | Freyman et al. | 604/187 |
| 2008/0009823 A1 | 1/2008 | McKay | 604/500 |
| 2008/0025952 A1 | 1/2008 | Scheule et al. | 424/93.2 |
| 2008/0281248 A1 | 11/2008 | Anheloiu et al. | 604/523 |
| 2009/0270806 A1 | 10/2009 | Macaulay et al. | 604/117 |
| 2010/0048990 A1* | 2/2010 | Bakos | A61B 17/3478 600/106 |
| 2010/0217073 A1 | 8/2010 | Fischer et al. | 600/104 |
| 2010/0312173 A1* | 12/2010 | McKay | A61B 17/3478 604/28 |
| 2011/0160533 A1 | 6/2011 | Sampson | 600/106 |
| 2011/0218485 A1 | 9/2011 | Tran et al. | 604/26 |
| 2011/0226646 A1 | 9/2011 | Wyrick | 206/365 |
| 2011/0288482 A1 | 11/2011 | Farrell et al. | 604/164.04 |
| 2011/0305772 A1 | 12/2011 | Cameron | 424/553 |
| 2013/0068224 A1 | 3/2013 | Srinivasan | 128/203.26 |
| 2013/0211380 A1 | 8/2013 | Cabrera-Aquino et al. | 604/187 |
| 2014/0081213 A1 | 3/2014 | Chevallier et al. | 604/198 |
| 2014/0323991 A1 | 10/2014 | Tang et al. | 604/272 |
| 2015/0066056 A1 | 3/2015 | Cabrera-Aquino et al. | 606/140 |

FOREIGN PATENT DOCUMENTS

| | | |
|---|---|---|
| JP | 2012-213406 | 11/2012 |
| WO | WO 2000/031235 | 6/2000 |
| WO | WO 2007/019646 | 2/2007 |
| WO | WO 2013/034651 | 3/2013 |
| WO | WO 2013/107068 | 7/2013 |
| WO | WO 2015/021448 | 2/2015 |

OTHER PUBLICATIONS

International Search Report and Written Opinion, dated Nov. 5, 2014, in connection with International Patent Application No. PCT/US2014/050441, 15 pages.

International Search Report and Written Opinion, dated Mar. 30, 2015, in connection with corresponding International Patent Application No. PCT/US2014/050446, 15 pages.

Final Office Action, dated Apr. 28, 2015, in connection with U.S. Appl. No. 13/815,206, 54 pages.

Response to International Search Report and Written Opinion, dated Jun. 8, 2015, in connection with International Patent Application No. PCT/US2014/050441, 49 pages.

Response to International Search Report and Written Opinion, dated Jun. 30, 2015, in connection with corresponding International Patent Application No. PCT/US2014/050446, 43 pages.

Written Opinion, dated Jul. 7, 2015, in connection with International Patent Application No. PCT/US2014/050441, 9 pages.

Response, dated Sep. 7, 2015, to the second Written Opinion, dated Jul. 7, 2015, in connection with International Patent Application No. PCT/US2014/050441, 40 pages.

International Report on Patentability, dated Sep. 29, 2015, in connection with corresponding International Patent Application No. PCT/US2014/050446, 35 pages.

U.S. Appl. No. 14/455,871, filed Aug. 8, 2014, 2015/0066056, Mar. 5, 2015.

Letter/Written Disclosure of the Supplemental Information Disclosure Statement for the above-referenced application, filed herewith on Jul. 12, 2017, 2 pages.

News Article, "Spotlight: Global BioTherapeutics—Cultivating Entrepreneurship in Gene Therapy," Published Sep. 30, 2015 [online] Retrieved from: <URL: mexicosalud.com/spotlight-global-biotherapeutics-cultivating-entrepreneurship-in-gene-therapy/, May 25, 2016, 6 pages.

Examination Report, dated Oct. 20, 2016, in connection with Canadian Patent Application No. 2,920,303, 3 pages.

Response, filed Nov. 28, 2016, to Examination Report, dated Oct. 20, 2016, in connection with Canadian Patent Application No. 2,920,303, 23 pages.

Notice of Allowance, dated Jan. 19, 2017, in connection with Canadian Patent Application No. 2,920,303, 1 page.

Examination Report, dated Nov. 17, 2016, in connection with European Patent Application No. 14 756 174.0, 3 pages.

Response, filed Feb. 23, 2017, to Examination Report, dated Nov. 17, 2016, in connection with European Patent Application No. 14 756 174.0, 208 pages.

Communication Pursuant to Rule 71(3) EPC (Intention to Grant), dated Apr. 28, 2017, in connection with European Patent Application No. 14 756 174.0, 7 pages.

Letter/Written Disclosure of the Supplemental Information Disclosure Statement for the above-referenced application, filed herewith on Apr. 28, 2012, 2 pages.

(56) References Cited

OTHER PUBLICATIONS

International Preliminary Report on Patentability, dated Nov. 12, 2015, in connection with International Patent Application No. PCT/US2014/050441, 36 pages.
U.S. Appl. No. 13/815,206. filed Feb. 7, 2013, 2013/0211380, Aug. 15, 2013.
U.S. Appl. No. 14/455,871, filed Aug. 8, 2014.
Letter/Written Disclosure of the Information Disclosure Statement for the above-referenced application, mailed on Nov. 26, 2014, 3 pages.
Brooks et al., "Specific organ gene transfer in vivo by regional organ perfusion with herpes viral amplicon vectors: implications for local gene therapy." Surgery 129(3):324-334 (2001).
David et al., "Gene therapy for the fetus: is there a future?" Best Pract Res Clin Obstet Gynaecol. 22(1):203-218 (2008).
Eastman et al., "Development of catheter-based procedures for transducing the isolated rabbit liver plasmid DNA," Human Gene Therapy 13:2065-2077 (2002).
Fabre et al., "Hydrodynamic gene delivery to the pig liver via an isolated segment of the inferior vena cava," Gene Ther., 15:452-462 (2008).
Fujita et al., "Sendai virus-mediated gene delivery into hepatocytes via isolated hepatic perfusion," Biological & Pharmaceutical Bulletin, 29:1728-1734 (2006).
Gagner et al., "Laparoscopic liver resection: benefits and controversies." Surg Clin North Am. 84(2):451-462 (2004).
Hodges et al., "Local delivery of viral vector mitigates neutralization by antiviral antibodies and results in efficient transduction of rabbit liver," Mol. Ther. 12:1043-1051 (2005).
Invalidity Search Report prepared by a third-party, "Invalidity Search—Provisional Application—Injectcion Device, Global Bio Therapeutics," redacted, dated May 21, 2014, 10 pages.
Jiao et al., "Clinical short-term results of radiofrequency ablation in primary and secondary liver tumors." Am J Surg. 177(4):303-306 (1999).
Kay et al., "Evidence for gene transfer and expression of factor IX in haemophilia B patients treated with an AAV vector." Nat Genet. 24(3):257-261 (2000).
Kinoshita et al., "Targeted gene delivery to selected liver segments via isolated hepatic perfusion," J Surg. Res., 160:47-51 (2010).
Kota et al., "Follistatin gene delivery enhances muscle growth and strength in nonhuman primates." Sci Transl Med. 1(6):6ra15, 8 pages (2009).
Ohashi et al., "Modified infusion procedures affect recombinant adeno-associated virus vector type 2 transduction in the liver," Human Gene Therapy 16:299-306 (2005).
Papadakis et al., "Promoters and control elements: designing expression cassettes for gene therapy." Curr Gene Ther. 4(1):89-113 (2004).
Podevin et al., "Factors influencing immune response after in vivo retrovirus-mediated gene transfer to the liver." J Gene Med. 6(1):16-21 (2004).
Schiffelers et al., "Cancer siRNA therapy by tumor selective delivery with ligand-targeted sterically stabilized nanoparticle." Nucleic Acids Res.32(19):e149, 10 pages (2004).
Shayakhmetov et al., "Adenovirus binding to blood factors results in liver cell infection and Hepatotoxicity," J. Virol. 79:7478-7491 (2005).
Yoshino et al., "Naked plasmid DNA transfers to the porcine liver using rapid injection with large volume," Gene Ther.13:1696-1702 (2006).
International Search Report and Written Opinion, dated May 23, 2013, in connection with International Patent Application No. PCT/US2013/025234, 24 pages.
Restriction Requirement, dated Sep. 19, 2013, in connection with U.S. Appl. No. 13/815,206, 6 pages.

Response to Restriction Requirement, dated Oct. 21, 2013, in connection with U.S. Appl. No. 13/815,206, 13 pages.
Response to International Search Report and Written Opinion, dated Dec. 9, 2013, in connection with International Patent Application No. PCT/US2013/025234, 49 pages.
Written Opinion, dated Jan. 27, 2014, in connection with International Patent Application No. PCT/US2013/025234, 9 pages.
Response to Written Opinion, dated Mar. 27, 2014, in connection with International Patent Application No. PCT/US2013/025234, 45 pages.
Office Action, dated Apr. 22, 2014, in connection with U.S. Appl. No. 13/815,206, 47 pages.
International Preliminary Report on Patentability, dated May 6, 2014, in connection with International Patent Application No. PCT/US2013/025234, 10 pages.
Response to Office Action, dated Oct. 22, 2014, in connection with U.S. Appl. No. 13/815,206, 31 pages.
Letter/Written Disclosure of the Supplemental Information Disclosure Statement for the above-referenced application, filed herewith on Mar. 15, 2018, 2 pages.
Machine-generated English translation of Japanese Patent No. JP 2000-070336, published on Mar. 7, 2000, generated on Nov. 28, 2017, 7 pages.
Office Action, dated Dec. 1, 2017, in connection with corresponding Chinese Patent Application No. 201480055640.0 [English translation and original document in Chinese], 8 pages.
Decision to Grant a European Patent Pursuant to Article 97(1) EPC, dated Oct. 6, 2017, in connection with corresponding European Patent Application No. 14 756 174.0, 2 pages.
Office Action, dated Oct. 3, 2017, in connection with corresponding Japanese Patent Application No. 2016-533484 [English summary, English translation and original document in Japanese], 14 pages.
Response, filed Dec. 22, 2017, to Office Action, dated Oct. 3, 2017, in connection with corresponding Japanese Patent Application No. 2016-533484 [English instructions and claims as sent Dec. 13, 2017, amended set of English claims as sent Dec. 20, 2017 and document as originally filed in Japanese with the Syringe Needle Gauge Chart of the Lab Basics Technical Library from Sigma-Aldrich], 52 pages.
Decision to Grant, dated Jan. 16, 2018, in connection with corresponding Japanese Patent Application No. 2016-533484 [English reporting letter and translation with original document in Japanese], 5 pages.
Office Action, dated Jan. 31, 2018, in connection with corresponding Eurasian Patent Application No. 201600139 [English translation and original document in Russian], 6 pages.
Letter/Written Disclosure of the Supplemental Information Disclosure Statement for the above-referenced application, filed herewith on Oct. 4, 2018, 2 pages.
Response, filed Feb. 24, 2018, to Office Action, dated Dec. 1, 2017, in connection with corresponding Chinese Patent Application No. 201480055640.0 [English instructions and document as filed in Chinese], 28 pages.
Notice of Allowance, dated Jun. 6, 2018, in connection with corresponding Chinese Patent Application No. 201480055640.0 [English translation and original document in Chinese], 4 pages.
Response, filed May 24, 2018, to Office Action, dated Jan. 31, 2018, in connection with corresponding Eurasian Patent Application No. 201600139 [English instructions and original document in Russian], 32 pages.
Letter, reporting Notice of Allowance, dated Aug. 8, 2018, in connection with corresponding Eurasian Patent Application No. 201600139 [English reporting letter and original document in Russian], 2 pages.
Certificate of Grant, dated May 11, 2018, in connection with corresponding Hong Kong Patent Application No. 16113717.7, 2 pages.

* cited by examiner

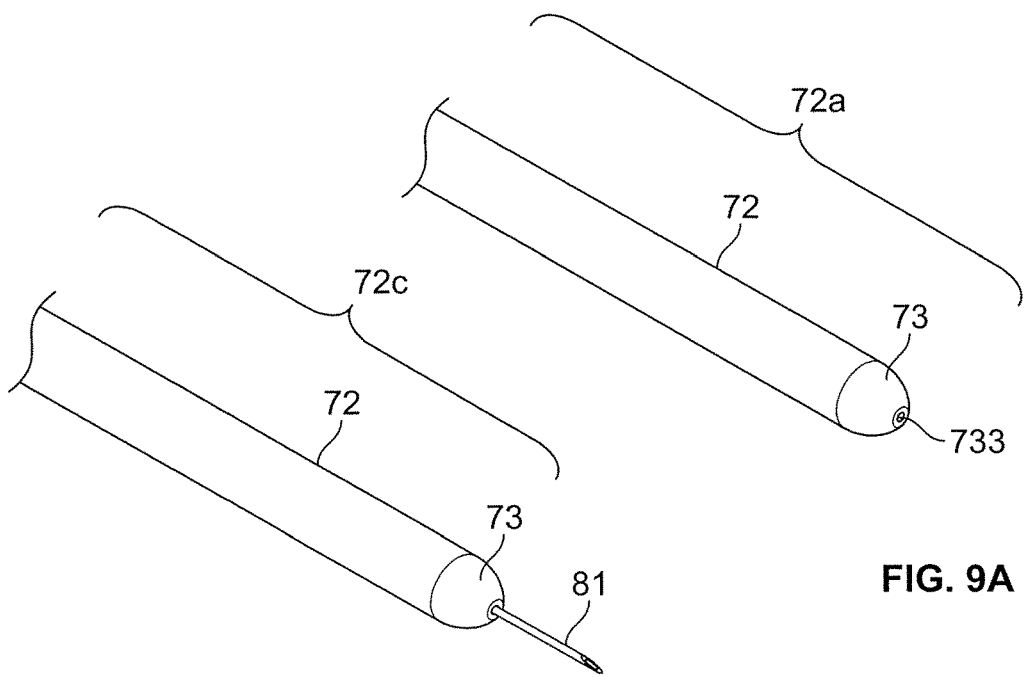
FIG. 9A
FIG. 9B
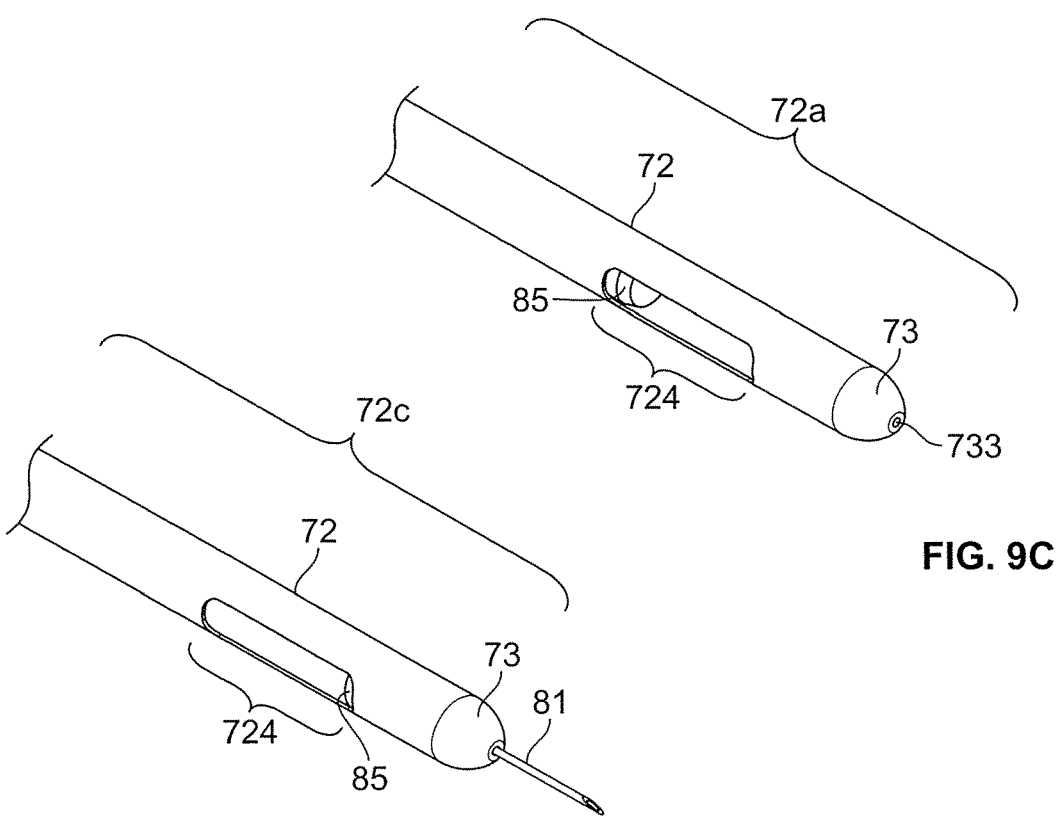
FIG. 9C
FIG. 9D

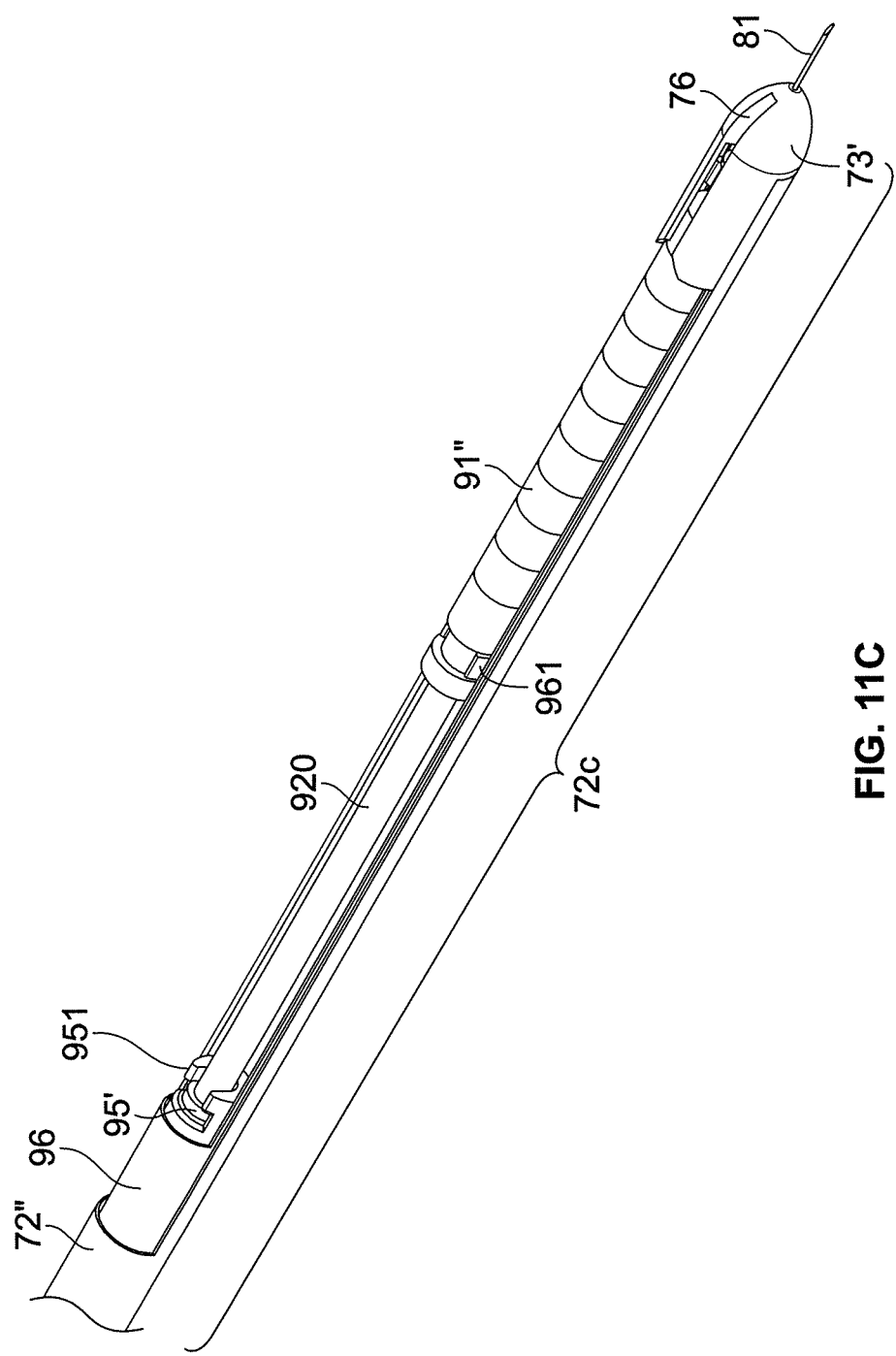

INJECTION DEVICE FOR MINIMALLY INVASIVE PROCEDURES AND USES THEREOF

RELATED APPLICATIONS

Benefit of priority is claimed to U.S. Provisional Application No. 61/863,888, filed Aug. 8, 2013, entitled "Injection Device for Minimally Invasive Procedures and Uses Thereof."

This application is related to International PCT Application Serial No. PCT/US2014/050446, filed the same day herewith, entitled "Injection Device for Minimally Invasive Procedures and Uses Thereof," which claims priority to U.S. Provisional Application No. 61/863,888.

This application is related to U.S. patent application Ser. No. 14/455,871, filed the same day herewith, and International PCT Application No. PCT/US2014/050441, filed the same day herewith, each entitled "Clamp Device for Minimally Invasive Procedures and Uses Thereof," both of which claim priority to U.S. provisional Application No. 61/863,903, filed Aug. 8, 2013, entitled "Clamp Device for Minimally Invasive Procedures and Uses Thereof".

This application also is related to U.S. application Ser. No. 13/815,206, filed Feb. 7, 2013, and International PCT Application No. PCT/US13/25234, filed Feb. 7, 2013, each entitled "Compartmentalized Method of Nucleic Acid Delivery and Compositions and Uses Thereof," both of which claim priority to U.S. Provisional Application Ser. No. 61/633,287, filed Feb. 7, 2012, entitled "Compartmentalized Method of Nucleic Acid Delivery and Compositions and Uses Thereof."

The subject matter of each of the above-noted applications is incorporated by reference in its entirety.

FIELD OF THE INVENTION

Provided herein is an injection device that can be used in minimally invasive procedures, including surgeries such as laparoscopic surgeries, for direct administration of a fluid, such as a therapeutic, to a target tissue or organ.

BACKGROUND

Many medical procedures, including minimally invasive procedures, can require direct injection of a fluid, such as a therapeutic, to a target tissue. Such procedures can require that the needle is inserted through a port at a distance far from the operator. This can create safety concerns, since it can be easy to puncture non-target tissues and/or to inadvertently puncture or pierce through tissues or organs with the needle. Thus, there is a need for injection devices that can be used in minimally invasive procedures that overcome these problems.

REFERENCE NUMERALS LIST

The following list indicates the terms used and the corresponding reference numerals. Reference to each should be made with respect to the description below and the accompanying Drawings.

60, 60' or 60"—laparoscopic injection device
71 or 71'—needle sheath controller
   710—needle sheath controller housing
   711—positioner
      711a—positioner—forward position
      711b—positioner—intermediate position
      711c—positioner—rearward position
   712—lock and release element
   713—connection member
   715—distal sheath stop
   716—proximal sheath stop
   717—controller lumen
72, 72' or 72"—needle sheath
   72a—needle sheath—sheathed position
   72b—needle sheath—transitional position
   72c—needle sheath—unsheathed position
   720—proximal portion of the needle sheath
   723—needle sheath lumen
   724—visibility window
   725—visibility window
   726—open cavity
73 or 73'—needle sheath distal tip
   733—needle channel
76—needle groove
81—injection needle
82—coupling member
83—injection tube
84—needle hub
85—needle coupler
900a—standard syringe—detached position
900b—standard syringe—connected position
910—dockable syringe
   910a—dockable syringe—undocked position
   910b—dockable syringe—docked position
91, 91' or 91"—syringe barrel
92, 92' or 92"—plunger
   920—auxiliary plunger
93—Luer fit adaptor
94—syringe barrel base
95 or 95'—plunger head
   951—plunger adaptor
96—syringe adaptor lining
   960—plunger rest cavity
   961—barrel dock
   962—barrel rest cavity
   963—barrel dock

SUMMARY

Provided herein are injection devices used for direct injection of a fluid, such as a therapeutic, to a target site of a subject, such as a target tissue or organ. The injection device can be used in minimally invasive procedures, such as surgeries and other procedures, for example in laparoscopic surgery. Also provided herein is a method and uses to use the injection devices, including in medical applications to treat diseases and conditions. As provided herein, the injection device includes a) a syringe barrel, in which the syringe barrel provides a fluid reservoir; b) a plunger configured to be controlled by the operator of the device and to move within the syringe barrel for loading and releasing fluid from the fluid reservoir in the syringe barrel; c) an injection needle that is operably coupled to the syringe barrel providing a fluid pathway for fluid contained in the syringe barrel to be injected into a target tissue when the plunger is depressed; d) an elongate sheath, which includes an internal lumen that contains the injection needle and having a distal tip that contains an opening for the injection needle, in which the sheath is movable around the injection needle; and e) a controller for positioning the sheath, which includes a housing, including at least a first and second stop to control exposure of the injection needle and that are provided within the housing at a predetermined distance from each other; a central lumen in the housing including a connection member, in which the connection member is configured to be movable in the central lumen in the housing and is coupled to the sheath, in which the proximal end of the sheath is coupled to the distal end of the connection member so that movement of the connection member controls movement of the sheath; and a positioner mounted within the housing configured to move forward towards the distal end of the controller and rearward towards the proximal end of the controller, between the stops in the housing, in which the positioner is operatively connected to the connection member to guide movement of the connection member in the same direction, whereby movement of the positioner forward towards the distal end engages the first stop and moves the sheath to enclose the injection needle inside the lumen of the sheath, and movement of the positioner rearward towards the proximal end engages the second stop and moves the sheath to expose no more than a predetermined length of the distal tip of the injection needle through the opening in the injection needle for injection into the tissue.

In examples of any of the injection devices herein, the elongate sheath has a sufficient length and width to reach an organ through an endoscopic port. For example, the elongate sheath generally has a length from its proximal to distal end of from or from about 200 mm to 600 mm and a diameter of from or from about 2 mm to 15 mm, and typically a length from its proximal to distal end of from or from about 250 to 400 mm and a diameter of 4 mm to 12 mm. For example, the elongate sheath has a length from its proximal to distal end of at least or about at least 300 mm and a diameter of at least or about at least 5 mm, 6 mm, 7 mm, 8 mm, 9 mm or 10 mm.

In examples of any of the injection devices herein, the predetermined length of the distal tip of the injection needle is generally 1 mm to 10 mm, 2 mm to 8 mm, 4 mm to 6 mm or 2 mm to 3 mm, and typically less than 10 mm, 9 mm, 8 mm, 7 mm, 6 mm, 5 mm, 4 mm, 3 mm, 2 mm or less. For example, the predetermined length is less than 5 mm.

In examples of any of the injection devices herein, the injection device can include at least 3 stops, 4 stops or 5 stops, in which the second stop is the most proximal stop and the first stop is the most distal stop and the other stop or stops are positioned between the first stop and the second stop; and each stop is positioned at a predetermined distance from adjacent stop or stops to control exposure of the needle to different predetermined lengths, in which the second stop controls exposure of the needle its longest predetermined length, whereby the positioner can move between the adjacent stops to engage with the stop to expose different predetermined lengths of the injection needle. Generally, the predetermined distance between stops is substantially the same as the predetermined length of the exposed injection needle.

In examples of any of the injection devices herein, the positioner can include a lock and release element that is configured in the positioner to engage the positioner with the stops. Typically, the lock and release element is a spring that provides an upward force against the positioner and a downward force against the connection member to lock the positioner into the stop, and is capable of being compressed to release the positioner from the stop.

In examples of any of the injection devices herein, the injection needle typically is 5 mm to 40 mm in length, and 25 gauge to 34 gauge, 25 gauge to 30 gauge or 26 gauge to 28 gauge. For example, injection needle is or is about 27 gauge.

In examples of any of the injection devices herein, the syringe barrel can be either proximal or distal to the controller.

In particular examples of the injection devices provided herein, the syringe barrel is proximal to the controller and is operably coupled to the injection needle by an injection tube, in which: the injection tube includes a proximal and a distal end, in which the proximal end is connected to the syringe barrel and the distal end connected to the injection needle; and the controller is configured to hold the injection tube and includes an opening at the proximal end so that the injection tube extends out of the controller to connect to the syringe barrel. In particular examples, the syringe barrel is configured to be connected to the injection tube so that the syringe barrel is detachable from the device. The syringe barrel can be connected to the injection tube, which includes a hub on its proximal end that is compatible with an adaptor on the distal end of the syringe barrel, and the hub of the injection tube connects to the adaptor of the syringe barrel.

In particular examples herein, the injection tube is fixed in the controller; the connection member in the controller includes a recess by which the injection tube is routed to pass from the controller into the sheath at the junction where the connection member is coupled to the sheath; and the connection member is movable around the injection tube. In some examples, the injection tube is connected directly to the injection needle. In other examples, the injection tube is connected indirectly to the injection needle via a coupler, the coupler having a proximal and distal end, the proximal end connected to the distal end of the injection tube and the distal end connected to the proximal end of the injection needle. The injection tube and injection needle can be the same gauge or a different gauges. In particular examples provided herein, the injection tube has a larger diameter than the injection needle; the injection needle can be 25 gauge to 34 gauge, 25 gauge to 30 gauge or 26 gauge to 28 gauge; and the injection tube can be 15 gauge to 25 gauge or 20 gauge to 25 gauge. For example, the injection needle is or is about 27 gauge and the injection tube is or is about 21 gauge.

In examples of any of the injection devices herein, the sheath can be opaque or transparent. In some examples of the injection devices provided herein, the coupler is opaque or transparent. In particular examples, the sheath is opaque; the coupler is transparent; and the sheath includes a window configured in the sheath to view the coupler.

In examples of any of the injection devices herein, the injection device can include a) a syringe barrel, in which the syringe barrel provides a fluid reservoir; b) a plunger configured to be controlled by the operator of the device and to move within the syringe barrel for loading and releasing fluid from the fluid reservoir in the syringe barrel; c) an injection needle that is operably coupled to the syringe barrel providing a fluid pathway for fluid contained in the syringe barrel to be injected into a target tissue when the plunger is depressed, in which: the injection needle is operably coupled to the syringe barrel by an injection tube, the injection tube includes a proximal and a distal end, the proximal end connected to the syringe barrel and the distal end directly or indirectly connected to the injection needle; the injection needle is 25 gauge to 34 gauge and has a length in the range from 5 mm to 40 mm; and the injection tube has a larger diameter than the injection needle that is has a smaller diameter than 25 gauge and is connected to the syringe barrel; d) an elongate sheath, which includes an internal lumen that contains the injection tube and injection needle and having a distal tip that contains an opening for the injection needle, in which the sheath is movable around the injection needle; and e) a controller for positioning the sheath, in which the controller is distal to the syringe barrel and plunger and which includes: a housing, including at least a first and second stop to control exposure of the injection needle and that are provided within the housing at a predetermined distance from each other; a cavity for the injection tube and an opening at the proximal end so that the injection tube extends out of the controller to connect to the syringe barrel, in which the injection tube is fixed in the controller; a central lumen in the housing which includes a connection member, in which: the connection member in the controller includes a recess by which the injection tube is routed to pass from the controller into the distal lumen of the sheath at the junction where the connection member is coupled to the sheath; the connection member is configured to be movable in the central lumen in the housing around the injection tube and is coupled to the sheath, in which the proximal end of the sheath is coupled to the distal end of the connection member so that movement of the connection member controls movement of the sheath; and a positioner mounted within the housing configured to move forward towards the distal end of the controller and rearward towards the proximal end of the controller, between the stops in the housing, in which the positioner is operatively connected to the connection member to guide movement of the connection member in the same direction, whereby movement of the positioner forward towards the distal end engages the first stop and moves the sheath to enclose the injection needle inside the lumen of the sheath, and movement of the positioner rearward towards the proximal end engages the second stop and moves the sheath to expose no more than a predetermined length of the distal tip of the injection needle through the opening in the injection needle for injection into the tissue In some examples provided herein, the total length of the injection tube and injection needle is as long as the controller and sheath. For example, the total length of the injection tube and injection needle can be 100 mm to 600 mm or 200 mm to 400 mm.

In some examples of the injection device provided herein, the syringe barrel is positioned distal to the controller and the internal lumen of the sheath includes the syringe barrel in its distal end; and the syringe barrel is configured in the lumen so that the sheath is movable around the syringe barrel. In particular examples, the sheath encloses the syringe barrel. In particular examples, the sheath can include a window to view the syringe barrel. In particular examples, the sheath includes an open cavity that includes the syringe barrel, where the open cavity of the sheath includes a lining that is configured in the sheath so that the sheath is movable around the lining; and the syringe barrel is mounted into the lining in the open cavity. In some examples, the open cavity extends the length of the sheath. The sheath can be enclosed at its proximal end and provides a conduit for the plunger and the open cavity is present at the distal end of the sheath.

In some examples provided herein, the plunger is extended to engage with the syringe barrel in the distal end of the lumen of the sheath and arranged so that the plunger is movable through the controller and within the lumen of the sheath.

In some examples provided herein, the plunger is longer than the sheath and has a length that is from or from about 100 mm to 600 mm or 200 mm to 500 mm.

In some examples provided herein, the plunger is operably connected to an auxiliary plunger provided in the lumen of the sheath; and the plunger is extended to engage with the auxiliary plunger in the lumen of the sheath and arranged so that the plunger is movable through the controller and sheath and the auxiliary plunger is movable through the sheath and configured to move within the syringe barrel, whereby depressing the plunger depresses the auxiliary plunger into the syringe barrel releasing fluid from the fluid reservoir in the syringe barrel and pulling back on the plunger pulls back on the auxiliary plunger to load fluid into the fluid reservoir in the syringe barrel. In particular examples, the plunger includes an adaptor at its distal end to connect to the proximal end of the auxiliary plunger. The sheath can include an open cavity which includes a detachable syringe; and the detachable syringe includes the syringe barrel, the auxiliary plunger having a distal end configured to be movable in the syringe barrel and a proximal end coupled to the plunger, and the injection needle that is operably coupled to the syringe. The open cavity of the sheath can include a lining that is configured in the sheath so that the sheath is movable around the lining; and the detachable syringe is mounted into the lining in the open cavity. In particular examples, the controller is configured to hold the plunger so that the plunger is movable within the controller, and the controller that includes: an opening at its proximal end to receive the plunger; and a recess in the connection member of the controller by which the plunger is routed to pass from the controller into the lumen of the sheath at the junction where the connection member is coupled to the sheath, in which the plunger and connection member move independently with respect to each other.

In some examples provided herein, the injection device includes a) a syringe barrel, in which the syringe barrel provides a fluid reservoir; b) an extended plunger configured to be controlled by the operator of the device and coupled to an auxiliary plunger to move within the syringe barrel for loading and releasing fluid from the fluid reservoir in the syringe barrel, whereby depressing the plunger depresses the auxiliary plunger into the syringe barrel releasing fluid from the fluid reservoir in the syringe barrel and pulling back on the plunger pulls back on the auxiliary plunger to load fluid into the fluid reservoir in the syringe barrel; c) an injection needle that is operably coupled to the syringe barrel providing a fluid pathway for fluid contained in the syringe barrel to be injected into a target tissue when the plunger is depressed, in which the injection needle is 25 gauge to 34 gauge and has a length in the range from 5 mm to 40 mm; d) an elongate sheath, which includes an internal lumen that contains the plunger, the auxiliary plunger, the syringe barrel and the injection needle and having a distal tip that contains an opening for the injection needle, in which: the sheath is enclosed at its proximal end and provides a conduit for the plunger, in which the plunger is movable through the sheath; the sheath includes an open cavity at the distal end, the open cavity which includes the auxiliary plunger, syringe barrel and injection needle, in which: the open cavity of the sheath includes a lining that is configured in the sheath so that the sheath is movable around the lining; the auxiliary plunger, syringe barrel and injection needle are mounted into the lining in the open cavity; and the auxiliary plunger, syringe barrel and injection needle are detachable as a unit from the open cavity; the sheath is movable around the plunger, auxiliary plunger, syringe barrel and injection needle; and e) a controller for positioning the sheath, which includes: a housing, including at least a first and second stop to control exposure of the injection needle and that are provided within the housing at a predetermined distance from each other; an opening at its proximal end to receive the plunger and which includes a cavity configured to hold the plunger so that the plunger is movable within the controller; a central lumen in the housing including a connection member, in which: the connection member includes a recess by which the plunger is routed to pass from the controller into the distal lumen of the sheath at the junction where the connection member is coupled to the sheath, in which the plunger and connection member move independently with respect to each other; the connection member is configured to be movable in the central lumen in the housing and is coupled to the sheath, in which the proximal end of the sheath is coupled to the distal end of the connection member so that movement of the connection member controls movement of the sheath; and a positioner mounted within the housing configured to move forward towards the distal end of the controller and rearward towards the proximal end of the controller, between the stops in the housing, in which the positioner is operatively connected to the connection member to guide movement of the connection member in the same direction, whereby movement of the positioner forward towards the distal end engages the first stop and moves the sheath to enclose the injection needle inside the lumen of the sheath, and movement of the positioner rearward towards the proximal end engages the second stop and moves the sheath to expose no more than a predetermined length of the distal tip of the injection needle through the opening in the injection needle for injection into the tissue.

In some examples provided herein, the injection device includes a) a syringe barrel, in which the syringe barrel provides a fluid reservoir; b) an extended plunger configured to be controlled by the operator of the device to move within the syringe barrel for loading and releasing fluid from the fluid reservoir in the syringe barrel; c) an injection needle that is operably coupled to the syringe barrel providing a fluid pathway for fluid contained in the syringe barrel to be injected into a target tissue when the plunger is depressed, in which the injection needle is 25 gauge to 34 gauge and has a length in the range from 5 mm to 40 mm; d) an elongate sheath, which includes an internal lumen that contains the plunger, the syringe barrel and the injection needle and having a distal tip that contains an opening for the injection needle, in which: the sheath is enclosed to provide a conduit for the plunger, in which the plunger is movable through the sheath; the sheath includes an a window to view the syringe barrel; the sheath is movable around the plunger, syringe barrel and injection needle; and e) a controller for positioning the sheath, which includes: a housing, including at least a first and second stop to control exposure of the injection needle and that are provided within the housing at a predetermined distance from each other; an opening at its proximal end to receive the plunger and including a cavity configured to hold the plunger so that the plunger is movable within the controller; a central lumen in the housing including a connection member, in which: the connection member includes a recess by which the plunger is routed to pass from the controller into the distal lumen of the sheath at the junction where the connection member is coupled to the sheath, in which the plunger and connection member move independently with respect to each other; the connection member is configured to be movable in the central lumen in the housing and is coupled to the sheath, in which the proximal end of the sheath is coupled to the distal end of the connection member so that movement of the connection member controls movement of the sheath; and a positioner mounted within the housing configured to move forward towards the distal end of the controller and rearward towards the proximal end of the controller, between the stops in the housing, in which the positioner is operatively connected to the connection member to guide movement of the connection member in the same direction, whereby movement of the positioner forward towards the distal end engages the first stop and moves the sheath to enclose the injection needle inside the lumen of the sheath, and movement of the positioner rearward towards the proximal end engages the second stop and moves the sheath to expose no more than a predetermined length of the distal tip of the injection needle through the opening in the injection needle for injection into the tissue.

In examples of any of the injection devices herein, the syringe barrel can be transparent and configured to hold 0.2 mL to 10 mL of fluid, 0.5 mL to 5 mL of fluid or 0.5 to 2 mL of fluid. For example, the syringe barrel holds at least or about at least or about 1 mL of fluid. The syringe barrel can be disposable or is re-usable.

In examples of any of the injection devices herein, the device can be disposable or is re-usable. The device is for delivering a therapeutic to an organ or tissue. The therapeutic can be a biologic, chemotherapeutic or gene therapy agent. For example, the therapeutic is a small molecule drug, prodrug, protein, peptide, DNA, RNA, virus, antibody, organic molecule, saccharide, polysaccharide, lipid and combinations or conjugates thereof.

Also provided herein is a method of directly administering a fluid to a tissue or an organ in a subject during a minimally invasive procedure, which includes: inserting any of the injection devices provided herein into a port or cannula configured to provide access to the tissue or organ during the minimally invasive procedure; and depressing the plunger to inject the fluid into the tissue. Methods provided herein include providing the device for inserting into the port with the positioner moved forward towards the distal end to engage with the first stop to move the sheath to enclose the injection needle inside the lumen of the sheath; and prior to depressing the plunger, moving the positioner rearward toward the proximal end to engage the second stop to move the sheath to expose the injection needle. In any of the methods provided herein, the tissue or organ is selected from among liver, brain spinal cord, pancreas, heart, skin, kidney, lung, blood vessel, bone, muscle, uterus, cervix, prostate, urethra, and intestine.

In any of the methods provided herein, the fluid is a composition including a therapeutic, which can be a biologic, chemotherapeutic or gene therapy agent. In any of the methods provided herein, the composition is a pharmaceutical composition.

In any of the methods provided herein, the therapeutic is a small molecule drug, prodrug, protein, peptide, DNA, RNA, virus, antibody, organic molecule, saccharide, polysaccharide, lipid and combinations or conjugates thereof. For example, the therapeutic can be a gene therapy agent, a chemotherapeutic agent, an analgesic agent, an anti-inflammatory agent, an antimicrobial agent, an amoebicidal agent, a trichomonocidal agent, an anti-parkinson agent, an antimalarial agent, an anticonvulsant agent, an anti-depressant agent, and antiarthritics agent, an anti-fungal agent, an antihypertensive agent, antipyretic agent, an anti-parasite agent, an antihistamine agent, an alpha-adrenergic agonist agent, an alpha blocker agent, an anesthetic agent, a bronchi dilator agent, a biocide agent, a bactericide agent, a bacteriostat agent, a beta-adrenergic blocker agent, a calcium channel blocker agent, a cardiovascular drug agent, a contraceptive agent, a decongestant agent, a diuretic agent, a depressant agent, a diagnostic agent, an electrolyte agent, a hypnotic agent, a hormone agent, a hyperglycemic agent, a muscle relaxant agent, a muscle contractant agent, an ophthalmic agent, a parasympathomimetic agent, a psychic energizer agent, a sedative agent, a sympathomimetic agent, a tranquilizer agent, a urinary agent, a vaginal agent, a viricide agent, a vitamin agent, a non-steroidal anti-inflammatory agent, an angiotensin converting enzyme inhibitor agent, an alcohol, or a sleep inducer. The therapeutic can be a polypeptide selected from among an enzyme, a hormone, a coagulation or clotting factor, a cytokine, a growth factor or active portion thereof, an antibody or antigen binding portions of antibodies, an angiogenesis modulator, an immunomodulator, a pain modulator, a receptor or active portion thereof, a transport protein, a regulatory protein, an antigen or an allergen.

In any of the methods provided herein, the therapeutic can be a nucleic acid molecule for gene therapy, and the nucleic acid molecule can encode a polypeptide. The encoded polypeptide can be an enzyme, a hormone, a coagulation or clotting factor, a cytokine, a growth factor or active portion thereof, an antibody or antigen binding portions of antibodies, an angiogenesis modulator, an immunomodulator, a pain modulator, a receptor or active portion thereof, a transport protein, a regulatory protein, an antigen and an allergen. For example, the encoded polypeptide can be adenosine deaminase, cystic fibrosis transmembrane conductance regulator (CTFR), galsulfase, laronidase, N-acetylgalactosamine 6-sulfatase, phenylalanine ammonia lyase, acid alpha glucosidase, imiglucerase, alglucosidase alpha, thyrotropin, growth hormone, insulin, thyroid hormone, erythropoietin (EPO), interleukin-1 (IL-1), IL-2, IL-3, IL-4, IL-5, IL-7, interferon-α (IFN-α), IFN-β, IFN-γ, tumor necrosis factor (TNF), IL-12, IL-18, Fms-Related Tyrosine Kinase 3 (flt3), neuropilin-2 (NP2), bone morphogenic protein (BMPs), epidermal growth factor (EGF), erythropoietin (EPO), fibroblast growth factor (FGF), granulocyte colony stimulating factor (G-CSF), granulocyte macrophage colony stimulating factor (GM-CSF), hepatocyte growth factor (HGF), insulin-like growth factor (IGF), platelet derived growth factor (PDGF), transforming growth factor α or β, vascular endothelial growth factor (VEGF), epidermal growth factor receptor (EGFR), fibroblast growth factor receptor (FGFR), FGFR antagonist (sFGFR) transforming growth factor receptor (TGFR), vascular endothelial growth factor receptor (VEGFR), plasminogen activator, urokinase, Factor VIII, Factor IX, von Willebrand factor, growth hormone, metalloproteinase thrombospondin motifs 1 (METH-1), METH-2, tryptophanyl-tRNA synthetase (TrpRS) fragments, proliferin-related protein, prolactin fragment, pigment epithelium-derived factor (PEDF), vasostatin, angiostatin, endostatin, kininostatin, fibrinogen-E fragment, thrombospondin, tumstatin, canstatin, restin, soluble fms-like tyrosine kinase-1 (sFlt-1), soluble vascular endothelial growth factor receptors (sFlk), soluble Neuropilin 1 (sNRP1), Interferon gamma-induced protein 10 (IP-10), Platelet factor 4 (PF-4), Gro-beta, soluble Ephrin type-B receptor 4 (sEphB4), sephrinB2, IGF-1, herpes simplex virus thymidine kinase (HSV-TK), carboxypeptidase G2 (CPG2), carboxylesterase (CA), cytosine deaminase (CD), cytochrome P450 (cyt-450), deoxycytidine kinase (dCK), nitroreductase (NR), purine nucleoside phosphorylase (PNP), thymidine phosphorylase (TP), varicella zoster virus thymidine kinase (VZV-TK), xanthine-guanine phosphoribosyl transferase (XGPRT), Aspartylglucosaminidase, α-Galactosidase A, Palmitoyl Protein Thioesterase, Tripeptidyl Peptidase, Lysosomal transmembrane protein, cysteine transporter, Acid ceramidase, acid α-L-fucosidase, protective protein/cathepsin A, acid β-glucosidase or glucocerebrosidase, acid β-galactosidase, iduronate-2-sulfatase, α-L-Iduronidase, galactocerebrosidase, acid α-mannosidase, acid β-mannosidase, arylsulfatase B, aryl-sulfatase A, N-Acetylgalactosamine-6-sulfate sulfatase, N-Acetylglucosamine-1-phosphotransferase, Acid sphingomyelinase, Niemann-Pick disease, type C1 (NPC-1), β-Hexosaminidase B, Heparan N-sulfatase, α-N-Acetylglucosaminidase (NaGlu), Acetyl-CoA:αglucosaminide N-acetyltransferase, N-Acetylglucosamine-6-sulfate sulfatase, β-Glucuronidase, acid lipase, neprilysin, the insulin-degrading enzyme insulysin, thimet oligopeptidase, calbindin D28, parvalbumin, hypoxia induced factor 1-alpha (HIF1-alpha), sirtuin-2 (SIRT-2), survival motor neuron protein-1 (SMN-1), SMN-2, glial cell-derived neurotrophic factor (GDNF), ciliary neurotrophic factor (CNF), low density lipoprotein receptor (LDLR), lipoprotein lipase (LPL), Alpha-1-Antitrypsin (AAT), UDP-glucuronyl-transferase (UGT), UGT1A1, glucose-6 phosphatase, phosphoenolpyruvate-carboxykinase, galactose-1 phosphate uridyl transferase, phenylalanine hydroxylase, branched chain alpha-ketoacid dehydrogenase, fumarylacetoacetate hydrolase, methylmalonyl-CoA mutase, ornithine transcarbamylase, argininosuccinic acid synthetase, adenosine deaminase, hyposanthine guanine phosphoribosyl transferase, biotinidase, beta-glucocerebrosidase, beta-glucuronidase, porphobilinogen deaminase (PBDG) or p53.

In any of the methods provided herein, the nucleic acid molecule can be a therapeutic nucleic acid molecule that encodes a therapeutic product, whereby delivery of the nucleic acid molecule effects treatment of a disease or condition. The disease or condition can be an arthritis, chronic pain, HIV-related AIDS, atherosclerosis, restenosis, inherited enzyme deficiency, inherited immune deficiency, cancer, a retrovirus infection, hemophilia, diabetes, a muscular dystrophy, a cardiovascular disorder, cystic fibrosis, a neurodegenerative disorder, trauma, pain, sickle cell anemia, autoimmune disease, inflammatory disease, and hypertension. In particular examples, the nucleic acid encoded polypeptide can be a Factor VIII for the treatment of hemophilia A; a Factor IX for the treatment of hemophilia B; an insulin gene for treatment of type I diabetes mellitus; an alpha-1-antitrypsin (AAT) for the treatment of alpha-1-antitrypsin (AAT) deficiency; a hemochromatosis protein (HFE) for treatment of hemochromatosis; a copper-transporting ATPase 2 for treatment of Wilson's disease; UDP glucuronosyltransferase 1A1 (UGT1A1) for the treatment of Crigler-Najjar syndrome type I; ornithine transcarbamylase (OTC) for the treatment of ornithine transcarbamylase deficiency, type II; low density lipoprotein receptor (LDLR) for the treatment of familial hypercholesterolemia; fibrinogen alpha (FGA), beta (FGB) or gamma (FGB) for the treatment of afibrinogenemia; glucose-6-phosphate-α for the treatment of glycogen storage disease (GSD) type Ia; G6PT for the treatment of GSD type Ib; acid-α-glucosidase for the treatment of GSD type II (Pompe); α-L-iduronidase for the treatment of mucopolysaccharidosis (MPSI); sulphamidase for the treatment of MPS IIIA; α-N-acetylglucosaminidase (NaGlu) for the treatment of MPS IIIB; β-glucuronidase for the treatment of MPS VII; α-galactosidase A for the treatment of Fabry disease; glucocerebrosidase for the treatment of Gaucher's disease; acid sphingomyelinase for the treatment of Niemann-Pick syndrome; phenylalanine hydroxylase for the treatment of phenylketonuria; TIMP antagonist or anti-HSC molecules for the treatment of liver fibrosis; anti-ROS molecules for the treatment of liver ischemia reperfusion injury; amyloid-beta degrading enzyme neprilysin, the insulin-degrading enzyme insulysin, or thimet oligopeptidase for the treatment of Alzheimer's disease; insulin growth factor-1 (IGF-1), calbindin D28, parvalbumin, HIF1-alpha, SIRT-2, VEGF, SMN-1, SMN-2, GDNF or ciliary neurotrophic factor (CNF) for the treatment of Amyotrophic Lateral Sclerosis (ALS); galactose-1 phosphate uridyl transferase for the treatment of galactosemia; branched chain alpha-ketoacid dehydrogenase for the treatment of maple syrup urine disease; fumarylacetoacetate hydrolase for the treatment of tyrosinemia type 1; methylmalonyl-CoA mutase for the treatment of methylmalonic acidemia; argininosuccinic acid synthetase for the treatment of citrullinemia; hyposanthine guanine phosphoribosyl transferase for the treatment of Gout and Lesch Nyan syndrome; beta-glucuronidase for the treatment of Sly syndrome; peroxisome membrane protein 70 kDa for the treatment of Zellweger syndrome, enfuvirtide for the treatment of Human immunodeficiency virus (HIV) infection; adenosine deaminase (ADA) for the treatment of combined immunodeficiency disease (SCID); CFTR for the treatment of cystic fibrosis; porphobilinogen deaminase (PBDG) for the treatment of acute intermittent *porphyria*; interferon-beta for the treatment of multiple sclerosis; lipoprotein lipase for the treatment of lipoprotein lipase deficiency (LPLD), p53 for the treatment of cancer; and glutamic acid decarboxylase (GAD) for the treatment of Parkinson's Disease.

For example, the nucleic acids molecules can encode a protein for treatment of a cancer. For example, the cancer can be a solid tumor, including, but not limited to, breast cancer, melanoma, head and neck cancer, colon cancer, renal carcinoma and sarcoma. Such cancers can be treated with any molecule that inhibits angiogenesis. Hence, a nucleic acid molecule can encode a protein that inhibits angiogenesis, including, but not limited to, endostatin, angiostatin, vasculostatin, thrombospondin-1, tissue inhibitor of metalloprotease (TIMP), soluble vascular endothelial growth factor (VEGF) receptor and vasostatin (calreticulin fragment). Such anti-angiogenic agents also can be used in the treatment of other angiogenic diseases or conditions, such as ocular diseases.

In any of the methods provided herein, the nucleic acid molecule can encode a polypeptide that increases muscle production in an animal, increases hair production in an animal, increases wool production in an animal, increases growth of an animal, or is involved in nutrient synthesis or utilization. For example, the encoded polypeptide can be: a polypeptide that increases muscle production in an animal that is a myostatin inhibitor; a polypeptide that increases growth in an animal that is a growth hormone, IGF-1, a growth hormone releasing factor or chicken Ski; or a polypeptide that is involved in nutrient synthesis or utilization that is a serine transacetylase and o-acetylserine sulphydrylase. In particular examples, the myostatin inhibitor is follistatin.

In any of the methods provided herein, the nucleic agent molecule can be a DNA molecule, a RNA molecule, or an aptamer. For example, the nucleic acid molecule can be a microRNA, a small interfering RNA, a ribozyme or an antisense nucleic acid. The nucleic acid can be delivered in a vehicle, which can be lipid vesicle, a virus or a microorganism. For example, the lipid vesicle can be a liposome or micelle. In other examples, the vehicle is a virus, and the virus can be an adenovirus, an adeno-associated virus (AAV), a retrovirus, a vaccinia virus or a herpes simplex virus. The retrovirus can be a lentivirus. In particular examples, the virus is an adenovirus, and the adenovirus can include a deletion in an E1, E2a, E2b, E3, or E4 coding region and have a serotype of adenovirus type 2 or adenovirus type 5. In some of the examples of methods provided herein, the amount of virus administered can be from or from about 10 to $1\times10^{12}$ particles, 10 to $1\times10^6$ particles, $1\times10^3$ to $1\times10^{12}$ particles, $1\times10^6$ to $1\times10^{10}$ particles, or $1\times10^7$ to $1\times10^9$ particles; or is or is from or from about 10 to $1\times10^{12}$ pfu, 10 to $1\times10^6$ pfu, $1\times10^3$ to $1\times10^{12}\pm1\times10^6$ to $1\times10^{10}$ pfu, or $1\times10^7$ to $1\times10^9$ pfu; or less than $1\times10^{12}$ particles, $1\times10^{11}$ particles, $1\times10^{10}$ particles, $1\times10^9$ particles, $1\times10^8$ particles, $1\times10^7$ particles, $1\times10^6$ particles, $1\times10^5$ particles, $1\times10^4$ particles, $1\times10^3$ particles or less; or is less than $1\times10^{12}$ pfu, $1\times10^{11}$ pfu, $1\times10^{10}$ pfu, $1\times10^9$ pfu, $1\times10^8$ pfu, $1\times10^7$ pfu, $1\times10^6$ pfu, $1\times10^5$ pfu, $1\times10^4$ pfu, $1\times10^3$ pfu or less.

In any of the methods provided herein, the subject can be a mouse, rat, cow, pig, sheep, goat, horse and human. For example, subject can be a human child under the age of 18 or is a human fetus.

In any of the methods provided herein includes removing the device from the port, in which prior to removing the device from the port, the positioner is moved forward towards the distal end to engage with the first stop to move the sheath to enclose the injection needle inside the lumen of the sheath.

BRIEF DESCRIPTION OF THE DRAWINGS

The drawings described herein are for illustrative purposes only of selected embodiments and not all possible implementations, and are not intended to limit the scope of the present disclosure.

FIG. 1A shows a perspective view of an exemplary embodiment of an injection device containing a standard syringe at the proximal end of the device. FIG. 1B illustrates connection of the syringe barrel to the needle sheath controller.

FIG. 4A is a birds-eye view showing the positioner positioned towards the distal end so that the needle sheath is in the sheathed position. FIG. 4B is a birds-eye view showing the positioner in an intermediate or middle position with the needle sheath in the transitioning position moving between the sheathed and unsheathed position. FIG. 4C is a birds-eye view showing the positioner position towards the proximal end so that the needle sheath is in the unsheathed position.

FIG. 8A shows the needle sheath in the sheathed position. FIG. 8B shows the needle sheath in the unsheathed position.

FIGS. 9A-9D show enlarged perspective views of the needle sheath in the device shown in FIGS. 1A and 1B. FIG. 9A illustrates the needle sheath in the sheathed position in a windowless needle sheath shaft. FIG. 9B illustrates the needle sheath in the unsheathed position in a windowless needle sheath shaft. FIG. 9C illustrates the needle sheath in the sheathed position in a needle shaft with a visibility window. FIG. 9D illustrates the needle sheath in the unsheathed position in a needle shaft with a visibility window.

FIG. 10A is a sectional view of the needle sheath in the sheathed position. FIG. 10B is a sectional view of the needle sheath in the unsheathed position. FIG. 10C is a perspective view of the needle sheath in the sheathed position. FIG. 10D is a perspective view of the needle sheath in the unsheathed position.

FIGS. 11A-11D illustrate enlarged views of the device shown in FIG. 3. FIG. 11A is a perspective view of the distal end of the device illustrating the syringe adaptor cavity and the syringe adaptor with the dockable syringe in the undocked position. FIG. 11B is a perspective view of the distal end of the device, with the dockable syringe docked onto the syringe adaptor and the needle sheath in the sheathed position. FIG. 11C is a perspective view of the distal end of the device, with the dockable syringe docked onto the syringe adaptor and the needle sheath in the unsheathed position. FIG. 11D is a perspective view of the distal end of the device, with the dockable syringe docked onto the syringe adaptor, the needle sheath in the unsheathed position and the dockable syringe plunger in the depressed position.

Figure 1A:
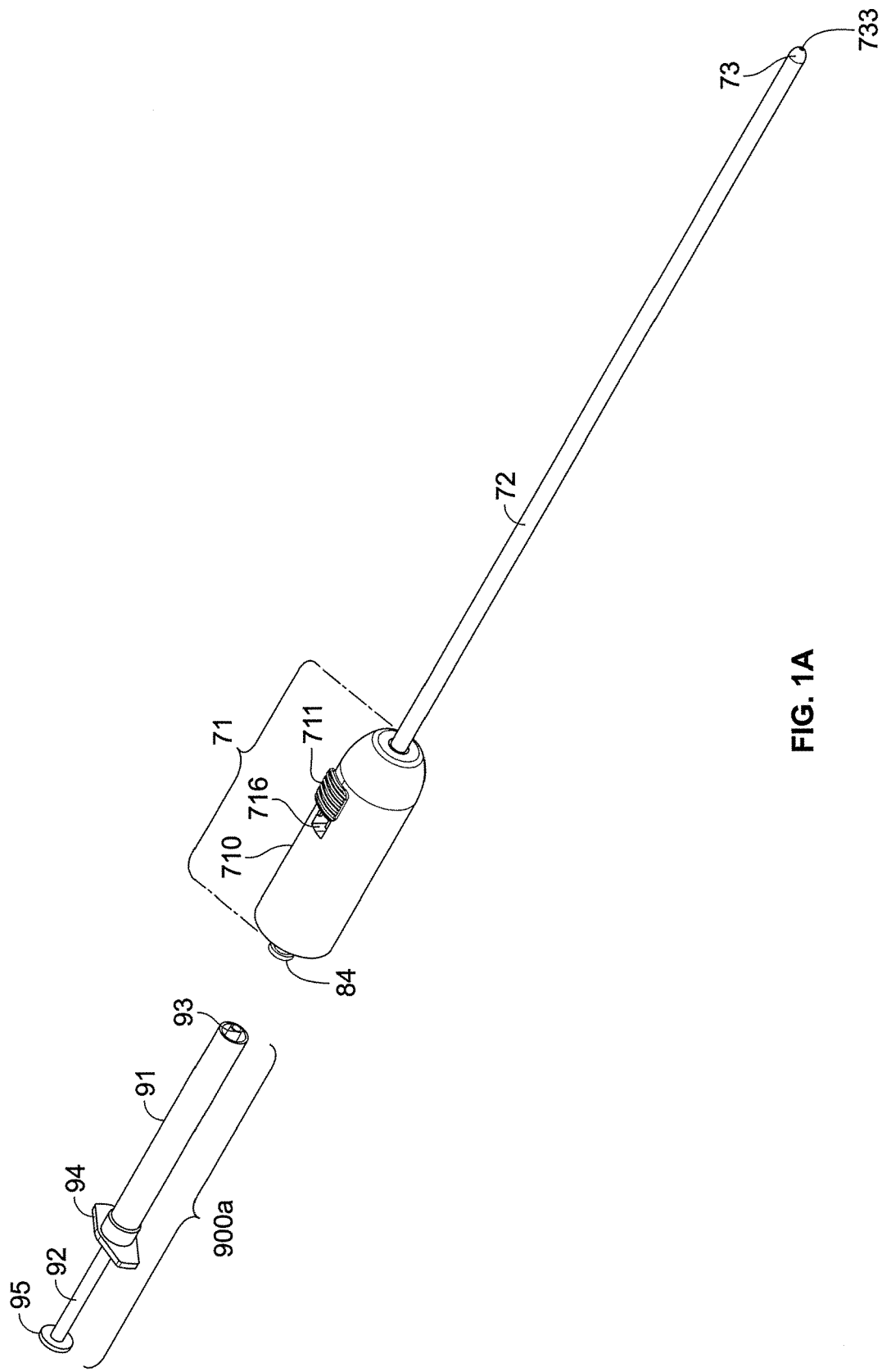
FIGS. 1A and 1B illustrate a standard syringe injection device.

Corresponding reference numerals indicate corresponding parts throughout the several views of the drawings. For parts which are similar but not the same as parts originally specified with a given number, a prime (') of the original numbers is used. A lowercase reference numeral (e.g. a, b, etc.) refers to the same part but in different positions or states.

DETAILED DESCRIPTION

A. Definitions
B. Injection Device
   1. Standard Injection Device
   2. Integrated Injection Device
   3. Dockable Injection Device
C. Applications and Uses
   1. Treating Diseases and Disorders
D. Examples

A. DEFINITIONS

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, reference to a "minimally invasive surgery" or a "minimally invasive procedure," also sometimes referred to as endoscopy, refers to any procedure (surgical or otherwise) that is less invasive than open surgery used for the same purpose. A minimally invasive procedure is carried out through the skin or through a body cavity or anatomical opening. The procedure typically involves use of devices suitable for the procedure, such as arthroscopic devices (for joints and the spine) or laparoscopic devices (for surgeries of abdomen). Minimally invasive procedures can be carried out with indirect observation of the surgical field through an endoscope or large scale display panel, and can involve manual or remote-control manipulation of instruments. Exemplary of a minimally invasive procedure is laparoscopy. Other minimally invasive procedures include, but are not limited to, refractive surgery, percutaneous surgery, arthroscopic surgery, cryosurgery, microsurgery, keyhole surgery, thoracoscopic surgery, endovascular surgery (such as angioplasty), coronary catheterization, stereotactic surgery, image-guided surgery, and ultrasound guided percutaneous ethanol treatment.

As used herein, "laparoscopy" or "laparoscopic surgery" refers to a minimally invasive surgical procedure in which operations in the abdomen are performed through small incisions. The incisions are typically 5 millimeters (mm) to 20 mm in length. One or several incisions are made, and laparoscopic ports, typically 5 mm to 12 mm in diameter, are inserted into the incisions. Laparoscopic surgical instruments are inserted or withdrawn through the laparoscopic ports.

As used herein, endoscope refers to an instrument that can be introduced into the body to give a view of its internal parts. A "laparoscope" refers to an instrument that can be introduced into the abdomen to give a view of its internal parts.

As used herein, "endoscopic port" refers to a medical appliance inserted into an incision for a minimally invasive procedure that provides a pathway that allows a minimally invasive device to pass through the skin or body cavity. With reference to laparoscopy, a "laparoscopic port" is a medial appliance inserted into an incision for a laparoscopic procedure that provides a pathway that allows a laparoscopic device to pass through the skin into the abdominal cavity.

As used herein, a device for minimally invasive procedures is a device that is sufficiently long and narrow to permit access to a tissue or an organ during minimally invasive procedures.

As used herein, a laparoscopic device is a device that is sufficiently long and narrow to permit access to a tissue or an organ during minimally invasive procedures.

As used herein, injection device refers to a device can that can be used to deliver fluids into the body or its cavities, such as a tissue or an organ or a portion thereof. The device generally contains a hollow barrel or syringe fitted with a plunger and a hollow needle for penetrating the target. For purposes herein, an injection device is one that can be used for minimally invasive procedures, such as laparoscopic surgeries or procedures.

As used herein, direct injection refers to injections given straight into the target, for example, straight into the tissue or organ or portion thereof.

As used herein, an organ or a tissue refers to differentiated parts of the body of a subject that performs a specific function. Tissues generally are a group of specialized cells that group together to form a specialized function. For example, muscle tissue is a specialized tissue that can contract. Organs are made up of tissues that perform a function. Examples of organs, include but are not limited to, the eyes, ears, lungs, liver, kidney, heart, or skin.

As used herein, reference to a "portion of a tissue or an organ" refers to part of a tissue or an organ of the body of a subject. The part can be a region, segment, lobe, section or other part of a tissue or an organ. The portion is one that can be mobilized or isolated separate from the rest of the tissue or organ. It also is a portion that is sufficient to effect delivery of the agent. It is within the skill of one in the art to determine the appropriate size of a portion of a tissue or an organ sufficient to effect delivery of the agent, and it depends upon the particular organ, the indication treated, the dosage, the size of the subject and other parameters. Typically, a portion of a tissue or an organ has a volume of at least about 5 mm$^3$, 10 mm$^3$ or more. For example, the portion can be any area of a tissue or an organ that has a length ranging from 0.5 cm to 25 cm, a height (or thickness) of 0.5 cm to 20 cm and/or a depth from 0.5 cm to 15 cm. As an example, a portion of a liver lobe or segment is one that has a length of 5 cm to 10 cm, a height of 1 cm to 3 cm and a depth (from the tip) of 1.5 cm to 3 cm. Smaller regions or portions are also contemplated so long as the portion is of a sufficient size to deliver a therapeutic or other agent.

As used herein, parenchyma refers to the portions of the tissue and associated cells of an organ that conducts the specific function of the organ and that makes up the bulk of the organ. Hence, the parenchyma is the main underlying functional tissue of an organ. These can include the epithelial tissue, muscle tissue, nervous tissue and associated cells thereof. Parenchyma is distinct from the stroma, which is the connective tissue, blood vessels, nerves and ducts. Hence, parenchyma does not include connective tissue, blood vessels, nerves and ducts. For example, the parenchyma of the liver includes hepatocytes, the parenchyma of the heart includes cardiac muscle cells such as myocytes, the parenchyma of the kidney includes nephrons. The parenchyma of the skin is the epidermis.

As used herein, "parenchymal cells" refers to the cells that are contained in or that make up the parenchyma of a tissue or an organ. For example, hepatocytes are cells of the main tissue of the liver, which make up 70-80% of the liver's mass. In the lung, 75% of all lung cells are contained in the parenchyma. These include, for example, fibroblasts of the interstitium and epithelial cells that line that alveoli, such as type 1 and type 2 cells (pneumocytes) and brush cells. In the skin, cells found in the parenchyma include epidermal cells such as keratinocytes. One of skill in the art is familiar with the parenchyma of various tissue and organs and cells therein.

As used herein, parenchymal injection refers to administration to the parenchyma of a tissue or an organ.

As used herein, "proximal" with reference to a component of the device or the device refers to the end of the component or the device that is closest to the medical professional operating the device during use of the device. It is understood that the proximal portion need not be the end of the component, but includes the entire portion of the component that is closest to the medical professional operating the device during use of the device.

As used herein, "distal" with reference to a component of the device or the device refers to the end of the device furthest from the medical professional during use of the device.

As used herein, "operably" or "operatively" when referring to two components means that the segments are arranged so that they function in concert for their intended purposes, e.g., movement of one component by another component.

As used herein, "engaged" refers to the condition in which two members that are designed to be contacted or connected are physically contacted to connected to each other in a manner in which they are designed to be contacted or connected. For example, an adaptor and a hub, such as Luer connectors, can be engaged when they are physically connected to each other in a manner in which they are designed to be connected. A groove (e.g. in sheath stops) and a notch that fits in the groove (e.g. in positioner), can be engaged when they are physically contacted to each other in a manner in which they are designed to be contacted.

As used herein, "male" with reference to a thread (e.g. of a Luer connector) refers to a member that includes a thread on its outer surface.

As used herein, "female" with reference to a thread (e.g. of a Luer connector) refers to a connecting member that includes a thread on its inner surface.

As used herein, elongate with reference to the sheath means that the sheath is long in relation to width or diameter. The elongate structure permits use of the device through ports to access the body cavity in minimally invasive procedures, such as laparoscopic procedures or surgeries.

As used herein, extended with reference to the plunger means that the proximal end of the plunger is not in proximity to the syringe barrel, such that the plunger is expanded or increased in length to cover a larger area so that it is able to operably connect with the syringe barrel.

As used herein, "substantially the same" with reference to the length of the exposed needle compared to the distance between sheath stops means that the length and distance are for the most part the same or essentially the same, but can differ slightly in a manner that is not significant. For example, the length of the exposed needle and the distance between sheath stops is substantially the same if the length of the exposed needle is longer or shorter than the distance between the sheath stops by no more than 1 mm, and generally less than 1 mm, 0.8 mm, 0.6 mm, 0.5 mm, 0.4 mm or less.

As used herein, sheath stop with reference to the needle sheath controller refers to an opening or groove formed in the controller to cease or halt or prevent the movement of the sheath. The engagement of the sheath with the stops need not be direct, but can be indirect. For example, the sheath can be operably coupled to a component that itself engages with stop. In examples of the device herein, the sheath is connected to a connection member that is connected to a positioner that engages directly with the stop to cease, halt or prevent the movement of the sheath. Hence, the stops lock the sheath from moving. The stops can be positioned at different distances from each other so that the sheath can be movably locked into more than one position (e.g. the sheathed and unsheathed position).

As used herein, "sheathed" or "the sheathed position" with reference to the injection needle means that the sheath is enclosed over the needle so that the sheath is not extended or exposed outside of the blunt end of the sheath.

As used herein, "unsheathed" or "the unsheathed position" with reference to the injection needle means that the distal tip of the needle extended or exposed outside of the sheath, and the sheath does not enclose the distal tip of the needle. The extent by which the distal tip of the needle is unsheathed is dependent on the particular device (e.g. sheath stops).

As used herein, axial force with reference to the plunger refers to force that directly acts on the center axis of an object. The axial force used herein is applied along the longitudinal axis. For example, axial force must be applied to depress or pull back the plunger. Axial force is typically compression force, e.g. depression of a plunger, or a stretching force, e.g. pulling back of a plunger.

As used herein, lumen refers to the inside space of a tubular structure. The tubular structure can have a regular tubular or cylindrical shape, or irregular tubular or cylindrical shape.

As used herein, cavity refers to an empty or hallow space or an opening leading to an empty space within an object.

As used herein, recess refers to an empty or hallow space created by part of an object which is constructed further back from the rest. It can be a hallow space created by walls surrounding the space. For example, a recess can be a groove with openings at one or both ends so that an item can pass through.

As used herein, predetermined length refers to a length that is set by the configuration of the device. Once the device has been constructed and configured, the predetermined length cannot be changed.

As used herein, loading a syringe refers to filling the syringe barrel, the fluid reservoir, with fluid. The syringe barrel is typically loaded or filled by pulling the plunger backward/rearward, toward the proximal end of the device.

As used herein, releasing, dispelling, expelling or ejecting a fluid from the syringe refers to emptying the fluid content of the syringe through the distal end of the syringe by depressing the plunger.

As used herein, lining refers to a separate layer of different material positioned on the inside surface of an object. For example, if a hallow tubular structure has another hallow tubular structure with a slightly smaller diameter fitted on the inside surface, the inner tubular structure is a lining for the outer tubular structure.

As used herein, integrated describes a part which is physically enclosed or encased with another part. Integrated parts cannot be separated from the part that encases or encloses the integrated part. With reference to the integrated injection device, the syringe barrel is enclosed or encased by the sheath and cannot be separated from the sheath.

As used herein, dockable or detachable describes a part which can be attached, docked, snap-fitted or placed into an adaptor of another part. Dockable parts can be attached docked, snap-fitted or placed into an adaptor in a reversible manner. For example, the part can be undocked or removed, i.e. separated from the part. Hence, the part is not physically bonded to the other part which contains the dock or the adaptor. With reference to the dockable syringe injection device, the syringe can be removed or undocked from the sheath. Likewise, with reference to the standard injection device, the syringe barrel can be detached from the device.

As used herein, dead volume refers to the volume of fluid that is loaded into the syringe barrel but cannot be expelled from the device and remains in the syringe barrel or needle. Factors that influence the amount of dead volume include the length of the needle, the diameter of the needle, and the diameter of the syringe barrel.

As used herein, injection pressure refers to the pressure required to inject the fluid out of the fluid reservoir into the target. Required injection pressure may differ depending on the properties of the composition of the fluid (e.g. viscosity), the length of the needle and the target site (e.g. hardness).

As used herein, pressure drop refers to the decrease in pressure as fluid flows through the fluid path, due to factors such as drag and frictional effect. Factors that can influence pressure drop include length of the needle, the diameter of the needle, and the viscosity of the fluid. If significant pressure drop occurs, the axial force applied to the plunger does not result in sufficient injection pressure at the needle.

As used herein, a composition refers to any mixture. It can be a solution, a suspension, fluid, powder, a paste, aqueous, non-aqueous or any combination thereof.

As used herein, fluid refers to any composition that can flow. Fluids thus encompass compositions that are in the form of semi-solids, pastes, solutions, aqueous mixtures, gels, lotions, creams and other such compositions. For purposes herein, a fluid generally is injectable.

As used herein, a therapeutic refers to an agent, a product, a compound or a composition that is capable of producing a therapeutic effect. The agent, product, compound or composition can comprise small molecule drugs, prodrugs, proteins, peptides, DNA, RNA, viruses, antibodies, organic molecules, saccharides, polysaccharides, lipids and combinations or conjugates thereof. The agent, product, compound or composition can include other pharmaceutically effective agents known in the general art to be of value in treating one or more of the diseases or medical conditions. Exemplary therapeutics are described herein.

As used herein, therapeutic effect means an effect resulting from treatment of a subject that alters, typically improves or ameliorates the symptoms of a disease or condition or that cures a disease or condition. A therapeutically effective amount refers to the amount of a composition, molecule or compound which results in a therapeutic effect following administration to a subject.

As used herein, "genetic therapy" or "gene therapy" involves the transfer of a nucleic acid molecule, such as heterologous DNA to certain cells, target cells, of a mammal, particularly a human, with a disorder or condition for which such therapy is sought. The DNA is introduced into the selected target cells in a manner such that the heterologous DNA is expressed and a therapeutic product encoded thereby is produced. Alternatively, the heterologous DNA can in some manner mediate expression of DNA that encodes the therapeutic product, it can encode a product, such as a peptide or RNA that in some manner mediates, directly or indirectly, expression of a therapeutic product. Genetic therapy also can be used to deliver nucleic acid encoding a gene product to replace a defective gene or supplement a gene product produced by the mammal or the cell in which it is introduced. The introduced nucleic acid can encode a therapeutic compound (e.g. a growth factor inhibitor thereof, or a tumor necrosis factor or inhibitor thereof, such as a receptor therefor), that is not normally produced in the mammalian host or that is not produced in therapeutically effective amounts or at a therapeutically useful time. The heterologous DNA encoding the therapeutic product can be modified prior to introduction into the cells of the afflicted host in order to enhance or otherwise alter the product or expression thereof.

As used herein, nucleic acid molecule refers to single-stranded and/or double-stranded polynucleotides, such as deoxyribonucleic acid (DNA) and ribonucleic acid (RNA), as well as analogs or derivatives of either RNA or DNA. Also included in the term "nucleic acid" are analogs of nucleic acids such as peptide nucleic acid (PNA), phosphorothioate DNA, and other such analogs and derivatives. Nucleic acids can encode gene products, such as, for example, polypeptides, regulatory RNAs, microRNAs, small inhibitory RNAs (siRNAs) and functional RNAs. Hence, nucleic acid molecule is meant to include all types and sizes of DNA molecules including siRNA, aptamers, ribozymes, complementary DNA (cDNA), plasmids and DNA including modified nucleotides and nucleotide analogs.

As used herein, a therapeutic nucleic acid is a nucleic acid molecule that encodes a therapeutic or is capable of producing a therapeutic effect. The product can be nucleic acid, such as a regulatory sequence or gene, or can encode a protein that has a therapeutic activity or effect. For example, therapeutic nucleic acid can be a ribozyme, antisense, double-stranded RNA, a nucleic acid encoding a protein and others.

As used herein, "vehicle" refers to the agent or conduit, such as vector or construct, that contains a nucleic acid molecule for gene therapy and that facilitates entry of the nucleic acid molecule into cells and/or expression thereof. Hence, the vehicle containing the nucleic acid is the delivered agent that is administered to a subject and that contains the nucleic acid molecule packaged therein or associated therewith. Examples of vehicles include, but are not limited to, a virus, virus-like particles, mini-circles, a plasmid or vector, a liposome and/or nanoparticle. For example, a vehicle can include a lipid-based or other polymer-based composition, such as liposome, micelle or reverse micelle, that is associated with a nucleic acid molecule or other agent, such as a non-viral vector or virus provided herein, for delivery into a host subject. The uptake of vehicles can be further increased or facilitated using various mechanical techniques such as electroporation, sonoporation or "gene gun."

As used herein, a heterologous nucleic acid (also referred to as exogenous nucleic acid or foreign nucleic acid) with reference to nucleic acid contained in the genome of a virus refers to a nucleic acid that is not normally produced in vivo by an organism or virus from which it is expressed or that is produced by an organism or a virus but is at a different locus, or that mediates or encodes mediators that alter expression of endogenous nucleic acid, such as DNA, by affecting transcription, translation, or other regulatable biochemical processes. Hence, heterologous nucleic acid is often not normally endogenous to an organism or a virus into which it is introduced. Heterologous nucleic acid can refer to a nucleic acid molecule from another virus in the same organism or another organism, including the same species or another species. Heterologous nucleic acid, however, can be endogenous, but is nucleic acid that is expressed from a different locus or altered in its expression or sequence (e.g., a plasmid). Thus, heterologous nucleic acid includes a nucleic acid molecule not present in the exact orientation or position as the counterpart nucleic acid molecule, such as DNA, is found in a genome. Generally, although not necessarily, such nucleic acid encodes RNA and proteins that are not normally produced by the organism or virus or in the same way in the virus in which it is expressed. Any nucleic acid, such as DNA, that one of skill in the art recognizes or considers as heterologous, exogenous or foreign to the virus in which the nucleic acid is expressed is herein encompassed by heterologous nucleic acid. Examples of heterologous nucleic acid include, but are not limited to, nucleic acid that encodes exogenous peptides/proteins, including diagnostic and/or therapeutic agents. Proteins that are encoded by heterologous nucleic acid can be expressed within the virus, secreted, or expressed on the surface of the virus in which the heterologous nucleic acid has been introduced.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, vector (or plasmid) refers to discrete elements that are used to introduce a heterologous nucleic acid into cells for either expression or replication thereof. The vectors typically remain episomal, but can be designed to effect integration of a gene or portion thereof into a chromosome of the genome. Vectors include non-viral vectors, such as non-viral expression vectors. Also contemplated are vectors that are artificial chromosomes, such as yeast artificial chromosomes and mammalian artificial chromosomes. Vectors also include "virus vectors" or "viral vectors." Selection and use of such vehicles are well known to those of skill in the art.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "virus," refers to any of a large group of infectious entities that cannot grow or replicate without a host cell. Viruses typically contain a protein coat surrounding an RNA or DNA core of genetic material, but no semipermeable membrane, and are capable of growth and multiplication only in living cells. Viruses include those that are formed when, such as when a vector containing all or a part of a viral genome, is transduced into an appropriate cell or cell line for the generation of such particles. The resulting viral particles have a variety of uses, including, but not limited to, transferring nucleic acids into cells either in vitro or in vivo. Thus, a virus is a packaged viral genome. A virus can refer to a single particle, a stock of particles or a viral genome.

As used herein, viral vector refers to a nucleic acid vector construct that includes at least one element of viral origin and can be packaged into a viral vector particle or virus. Reference to viral vector herein is used interchangeably with virus when it is packaged inside a protein coat. The viral vector particles or virus can be used for the purpose of transferring DNA, RNA or other nucleic acids into cells either in vitro or in vivo. Viral vectors include, but are not limited to, retroviral vectors, vaccinia vectors, lentiviral vectors, herpes virus vectors (e.g., HSV), baculoviral vectors, cytomegalovirus (CMV) vectors, papillomavirus vectors, simian virus (SV40) vectors, Sindbis vectors, Semliki Forest virus vectors, phage vectors, adenoviral vectors, and adeno-associated viral (AAV) vectors. Suitable viral vectors are described, for example, in U.S. Pat. Nos. 6,057,155, 5,543,328 and 5,756,086. Viral vectors typically include engineered viruses that are operatively linked to exogenous genes to transfer (as vehicles or shuttles) the exogenous genes into cells.

As used herein, "adenovirus vector" and "adenoviral vector" are used interchangeably and are well understood in the art to mean a polynucleotide containing all or a portion of an adenovirus genome. An adenoviral vector, refers to nucleic acid encoding a complete genome or a modified genome or one that can be used to introduce heterologous nucleic acid when transferred into a cell, particularly when packaged as a particle. An adenoviral vector can be in any of several forms, including, but not limited to, naked DNA, DNA encapsulated in an adenovirus capsid, DNA packaged in another viral or viral-like form (such as herpes simplex, and AAV), DNA encapsulated in liposomes, DNA complexed with polylysine, complexed with synthetic polycationic molecules, conjugated with transferrin, complexed with compounds such as PEG to immunologically "mask" the molecule and/or increase half-life, or conjugated to a non-viral protein.

As used herein, the term "adenovirus" or "adenoviral particle" is used to include any and all viruses that can be categorized as an adenovirus, including any adenovirus that infects a human or an animal, including all groups, subgroups, and serotypes. Depending upon the context reference to "adenovirus" can include adenoviral vectors. There are at least 51 serotypes of adenovirus that are classified into several subgroups. For example, subgroup A includes adenovirus serotypes 12, 18, and 31. Subgroup B includes adenovirus serotypes 3, 7, 11a, 11p, 14, 16, 21, 34, 35 and 50. Subgroup C includes adenovirus serotypes 1, 2, 5, and 6. Subgroup D includes adenovirus serotypes 8, 9, 10, 13, 15, 17, 19, 19p, 20, 22-30, 32, 33, 36-39, 42-49 and 51. Subgroup E includes adenovirus serotype 4. Subgroup F includes adenovirus serotypes 40 and 41. Thus, as used herein an adenovirus or adenovirus particle is a packaged vector or genome. For purposes herein, the viruses typically are recombinant adenoviruses containing a heterologous nucleic acid molecule in its genome and formed when an adenovirus vector is encapsulated in an adenovirus capsid.

Included among adenoviruses are any and all viruses that can be categorized as an adenovirus, including any adenovirus that infects a human or an animal, including all groups, subgroups, and serotypes. Thus, as used herein, "adenovirus" and "adenovirus particle" refer to the virus itself and derivatives thereof and cover all serotypes and subgroups and naturally occurring and recombinant forms, except where indicated otherwise. Included are adenoviruses that infect human cells. Adenoviruses can be wildtype or can be modified in various ways known in the art or as disclosed herein. Such modifications include, but are not limited to, modifications to the adenovirus genome that is packaged in the particle in order to make an infectious virus. Exemplary modifications include deletions known in the art, such as deletions in one or more of the E1a, E1b, E2a, E2b, E3, or E4 coding regions. Other exemplary modifications include deletions of all of the coding regions of the adenoviral genome. Such adenoviruses are known as "gutless" adenoviruses. The terms also include replication conditional adenoviruses, which are viruses that preferentially replicate in certain types of cells or tissues but to a lesser degree or not at all in other types.

As used herein, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject in need of a therapeutic agent. The term patient or subject includes human and veterinary subjects. Both therapeutic, industrial, veterinary and agricultural (e.g., meat production) uses are disclosed herein.

As used herein, a patient refers to a human subject.

As used herein, a combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, the singular forms "a," "an" and "the" include plural referents unless the context clearly dictates otherwise.

As used herein, the term "or" is used to mean "and/or" unless explicitly indicated to refer to alternatives only or the alternatives are mutually exclusive.

As used herein, ranges and amounts can be expressed as "about" a particular value or range. About also includes the exact amount. Hence "about 5 grams" means "about 5 grams" and also "5 grams." It also is understood that ranges expressed herein include whole numbers within the ranges and fractions thereof. For example, a range of between 5 grams and 20 grams includes whole number values such as 5, 6, 7, 8, 9, 10, 11, 12, 13, 14, 15, 16, 17, 18, 19 and 20 grams, and fractions within the range including, but not limited to, 5.25, 6.72, 8.5 and 11.95 grams.

As used herein, "optional" or "optionally" means that the subsequently described event or circumstance does or does not occur and that the description includes instances where said event or circumstance occurs and instances where it does not.

B. INJECTION DEVICE

Provided herein is are injection devices that can be used in minimally invasive procedures, such as laparoscopic procedures, for use in delivering fluids, such as therapeutics, by direct injection into a target locus, such as by direct injection into a target tissue. The device has an elongated needle sheath with a small diameter, and can be inserted through an endoscopic port, such as a laparoscopic ports, trocars or cannulas, to reach the internal target site. The device provided herein can deliver small and accurate doses of the fluid directly into the target tissue, without the need of large standard syringes and open surgery. The device can optionally deliver multiple doses to the same or different target sites.

The device can be used in any method that requires direct injection of an agent into a target site, in which access to the target site is limited, such as in minimally invasive procedures. For example, in addition to laparoscopic surgeries, the device provided herein can also be used for direct injection of a fluid, such as a therapeutic, during other minimally invasive medical or surgical procedures, such as thoracoscopic surgery. As described elsewhere herein, any fluid, such as a therapeutic, can be administered, including but not limited to, protein, nucleic acid, small molecule, virus, antibodies or other fluids. The device can be used in conjunction with other minimally invasive surgical devices using single-port or multi-port endoscopic (e.g. laparoscopic) surgery. The device can also be used to deliver multiple discrete doses to the same or different sites of injection without removing or after removing the device from the laparoscopic port.

As described further below, in all embodiments of the device, the device contains a movable sheath enclosing a fixed needle. The sheath contains an opening to expose the needle, whereby movement of the sheath is controlled by stops in a controller that can be adjusted by a positioner that moves between stops in the controller. The stops are positioned a predetermined distance so that movement of the positioner forward towards the distal end engages the first stop and moves the sheath to enclose the injection needle inside the lumen of the sheath, and movement of the positioner rearward towards the proximal end engages the second stop to move the sheath to expose no more than a predetermined length of the distal tip of the injection needle. Hence, the sheath moves around the fixed needle and is able to retract from its enclosed position to expose a desired length of needle for penetration of a tissue or organ. The particular length of the needle that is exposed is a function of the predetermined distance between the stops in the controller. The stops also can be locked to prevent movement of the needle once it is placed.

The ability to control movement of the sheath to fully enclose the needle or to expose the needle only a desired length, are features of the injection device that permit its use for direct administration to a parenchymal tissue or other desired locus. For example, the ability to enclose the needle by the sheath prevents unwanted exposure of the needle where its penetration into target tissues is not desired, which can occur when the device is being positioned for direct injection or when it is being removed from a subject. Also, the ability to control the extent or length of needle that is exposed ensures that the needle is no longer than the thickness of the tissue or organ so that the needle cannot puncture through the tissue or organ when it is injected.

Further, because the needle is fixed and does not move relative to the needle sheath controller, the positioner only controls the movement of the needle sheath, while the injection needle and other components of the device are stationary regardless of the position of the positioner. Thus, control of the movable sheath, and hence needle retraction or extension, is independent from movement of the plunger. This ensures precise injection into the tissue by the plunger without disturbing the placement of the needle in the tissue. In addition, because the needle is fixed and independent of the plunger, movement of the plunger only controls the drawing up and dispelling of fluids. This means that the plunger can be pulled back at the site of injection to draw up fluids to test needle placement (e.g. to confirm injection is not into a blood vessel), without disturbing placement of the needle. As described herein, embodiments of the injection device also can contain a visibility window (e.g. a transparent syringe barrel or needle coupler) to visualize the fluid that is drawn up by the plunger.

The injection devices provided herein include devices that are configured to minimize dead volume and/or avoid problems in pressure drops, which are problems with injection devices for minimally invasive, such as laparoscopic, surgeries. Thus, the injection devices generally avoid loss of the fluid, such as a therapeutic, that is being injected by the device. Also, because the injection devices provided herein are configured so that any problems with pressure drop are minimized, the injection devices provided herein also do not require undue axial force to depress the plunger to compensate for pressure drops. Therefore, the devices are safe to use and efficient to use.

The device, including exemplary embodiments of the device, will be described with reference to the accompanying drawings. As indicated, the use of a prime (') designation with a number indicates that the element shown or described is the same as the non-prime element, except as shown or described differently.

The device generally has two ends, the needle tip end and the plunger end. For clarity of description, it should be noted that the exemplary devices are depicted with the needle tip end generally towards the right side in the drawings, and the plunger end generally towards the left side of the drawing. The needle tip end will be generally described as the "distal end," and the plunger end will be generally described as the "proximal end." The term "distal end" is intended to refer to the end of the injection device furthest from the person holding the device, and the term "proximal end" is intended to refer to the end of the device closest to the holder of the device. If a component is described to be more "proximal" to another component, the component is closer to the proximal (plunger) end. If a component is described to be more "distal" to another component, the component is closer to the distal (needle tip) end.

Some components of the injection device can move in two general directions along the longitudinal axis relative to other components. For example, components can generally move towards the proximal end or distal end, or move in the proximal direction or the distal direction. Components that move towards the distal direction (needle tip) are described as moving forward, and components that move toward the proximal direction (plunger) are described as moving rearward/backward. The exemplary devices are also generally depicted with needle sheath controller positioned so that the positioner is pointing upward, with the exception of FIGS. 4A-4C, which are birds-eye views looking down on the device. Some of the components, such as the positioner, can move parallel to the vertical axis. The components can move in the upward direction or the downward direction. Pressing of the positioner toward the needle sheath controller will be described as pressing "downward" and releasing the positioner will be described as the positioner moving "upward."

In a general embodiment, the injection device, or apparatus, provided herein, includes a needle sheath and needle sheath controller, an injection needle with a needle tip that can be sheathed and unsheathed, a syringe barrel used as a reservoir for the fluid, such as a therapeutic, that is being delivered to the target tissue and a plunger that controls loading and release of the fluid. The needle sheath generally is a rigid shaft, but a flexible or steerable shaft can also be used depending on the purpose of use.

Figure 1B:
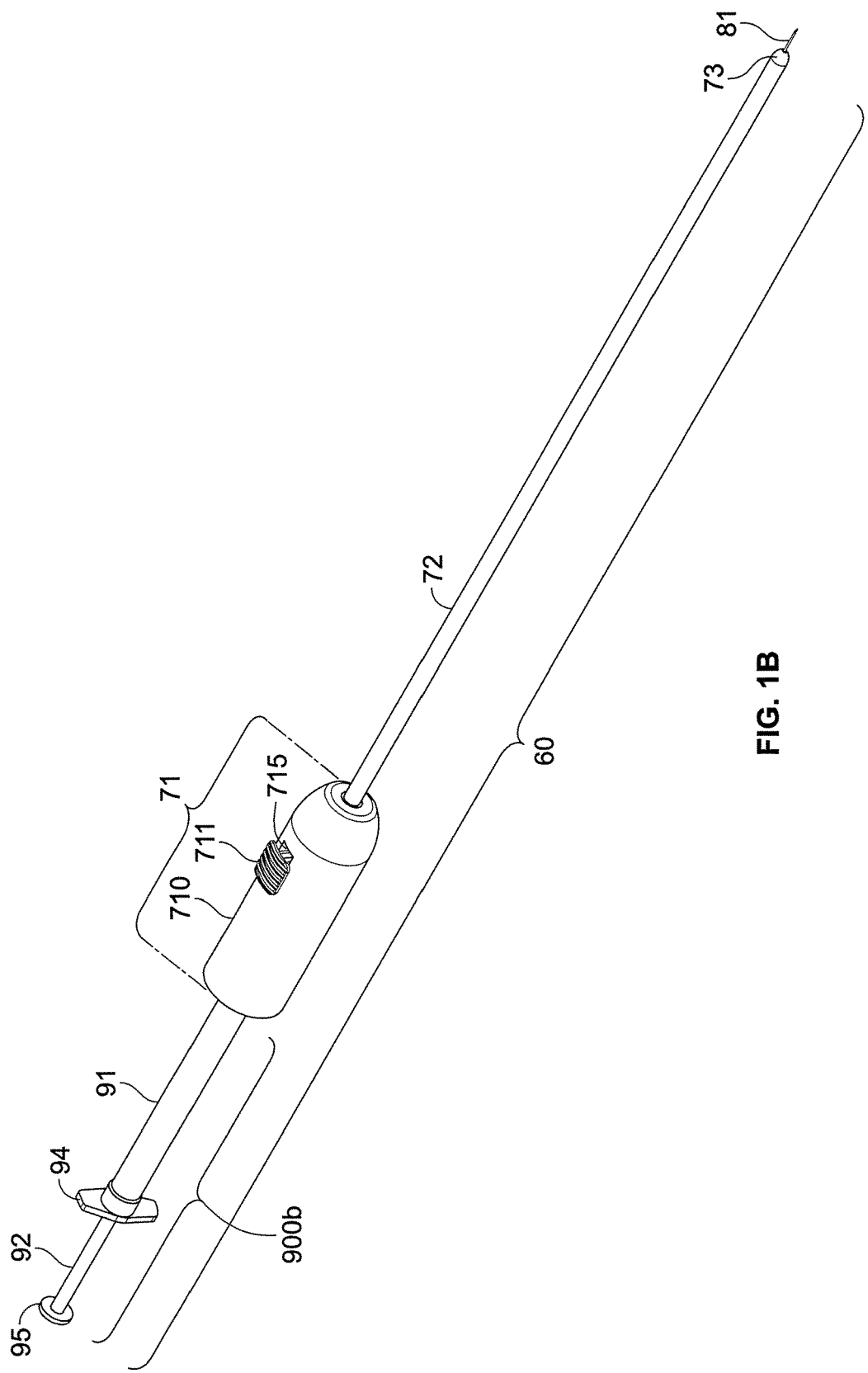
Figure 2:
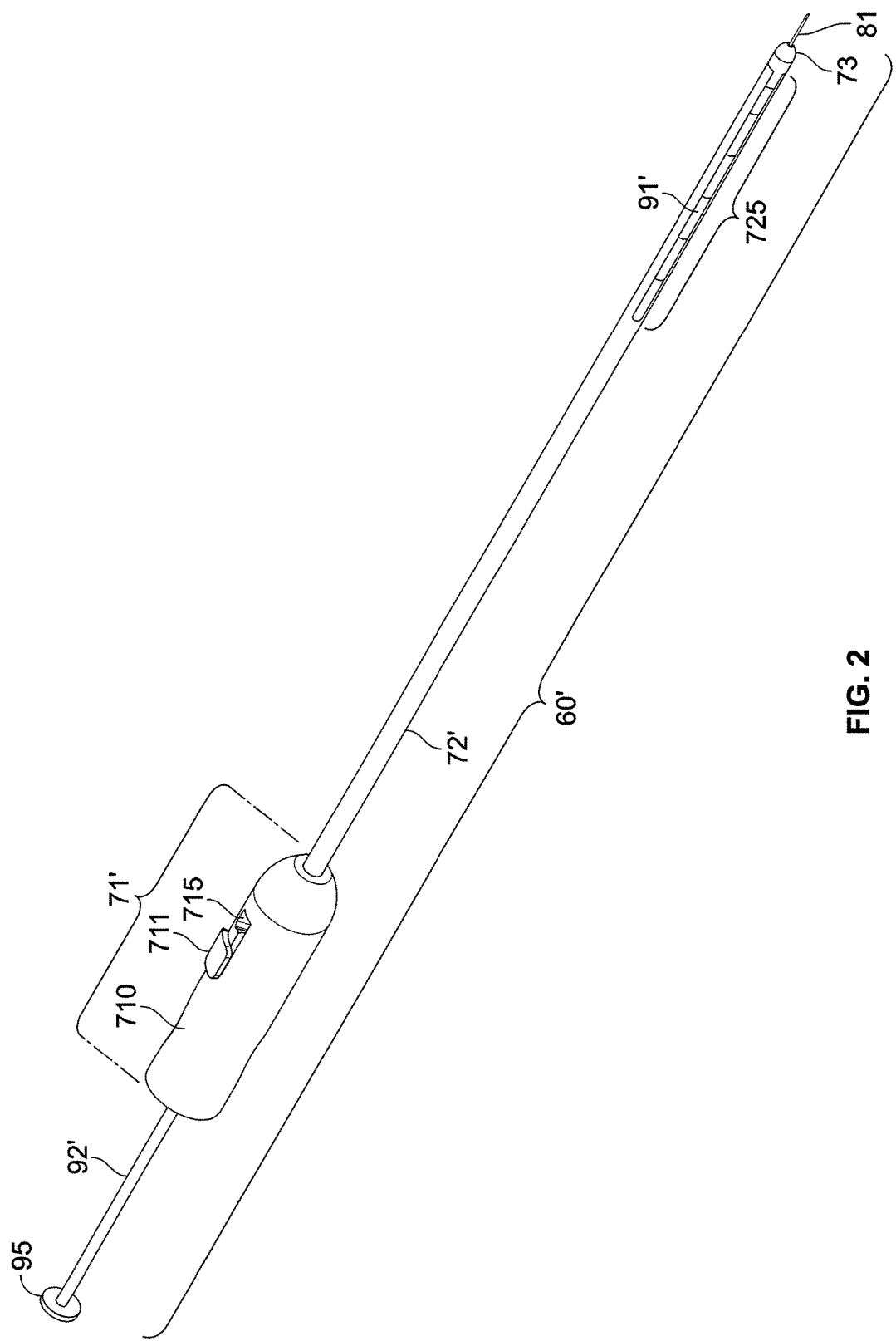
FIG. 2 shows a perspective view of an exemplary embodiment of an integrated syringe injection device in which a syringe barrel is integrated into the needle sheath lumen at the distal end of the device.
Figure 3:
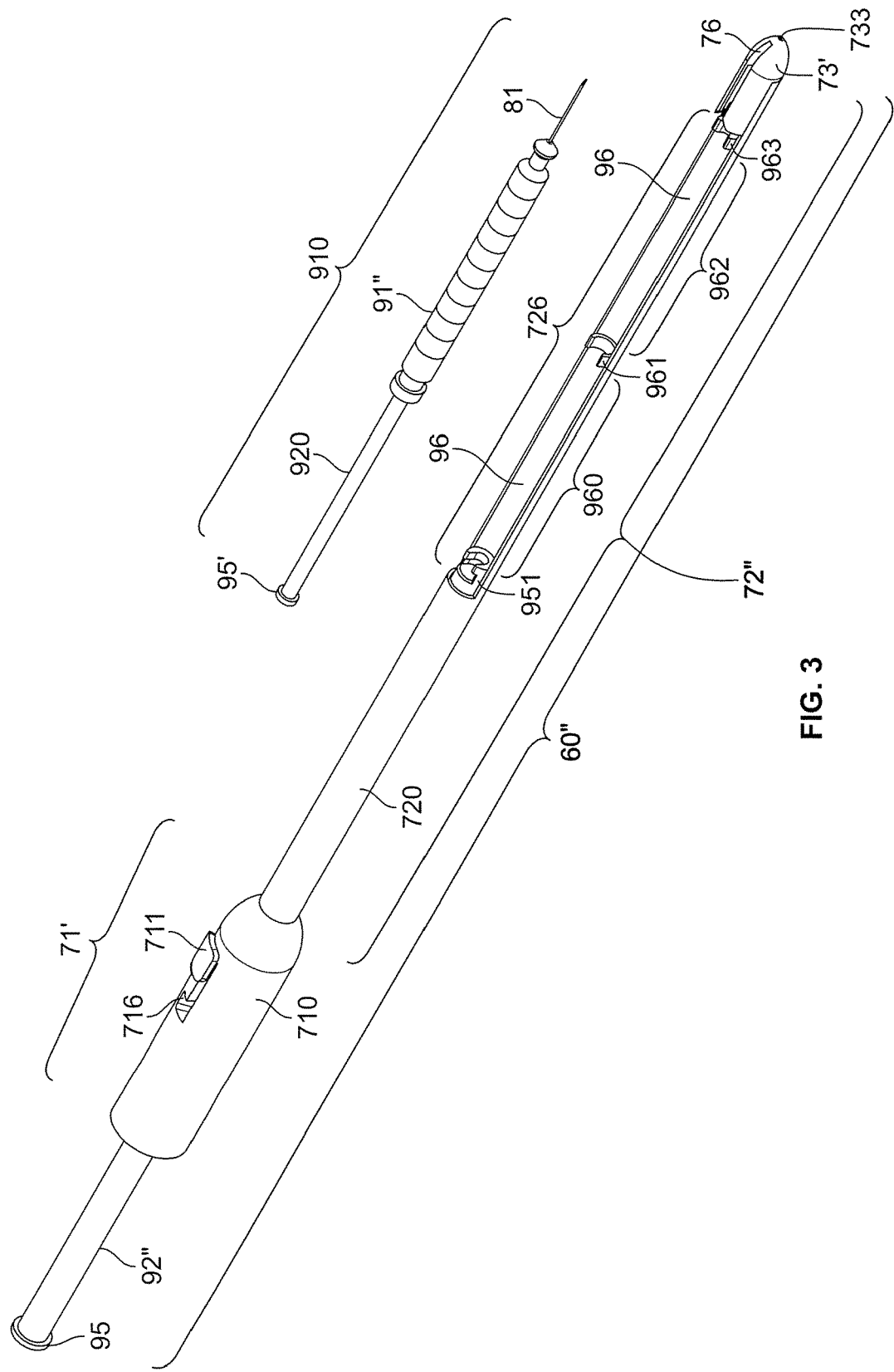
FIG. 3 shows a perspective view of an exemplary embodiment of a dockable syringe injection device in which a syringe containing an auxiliary plunger, barrel and injection needle are adapted to be docked onto a syringe adaptor within the needle sheath lumen at the distal end of the device

For example, with reference to FIGS. 1A and 1B, which illustrate a first exemplary embodiments provided herein, the syringe injection device is indicated generally by the reference numeral 60, and includes the needle sheath 72 and needle sheath controller 71, the injection needle 81, the syringe barrel 91 and the plunger 92. Other embodiments of the syringe device are described in FIG. 2 and FIG. 3, and other Figures as described below. For example, FIG. 2 shows a further embodiment indicated generally by the reference numeral 60', and includes the needle sheath 72', needle sheath controller 71', the injection needle 81, the syringe barrel 91' and the plunger 92'. In this embodiment, the needle sheath 72', needle sheath controller 71', the syringe barrel 91' and the plunger 92' are substantially the same as the embodiment of FIGS. 1A and 1B, except that that the syringe barrel 91' is located at the distal end of the device and is integrated with the needle sheath 72' and therefore the plunger 92' traverses through the needle control sheath controller 71'. FIG. 3 shows a further embodiment indicated generally by the reference numeral 60", and includes the needle sheath 72", the needle sheath controller 71', the injection needle 81, the syringe barrel 91" and the plunger 92". In this embodiment, the needle sheath 72", needle sheath controller 71', syringe barrel 91" and plunger 92" are substantially the same as the embodiment of FIGS. 1A and 1B, except that the syringe barrel 91" is located at the distal end of the device and is adapted so that it is dockable into the needle sheath 72". Further, the plunger 92" traverses the needle sheath controller 71', and is further adapted to associate with an auxiliary plunger 920 located distal to the needle sheath controller 71' where the auxiliary plunger 920 is adapted to move within the syringe barrel 91".

In all embodiments of the laparoscopic device provided herein, the dimensions of the laparoscopic device permits its use through typical ports for laparoscopic surgery or other minimally invasive surgical procedures. For example, typical ports for laparoscopic surgery, through which the instruments or devices enter the patient, is about 5 to 10 mm in diameter. The device is used to reach and inject into the target tissue, which is typically an internal tissue or organ of the body, including the parenchyma of an organ. The length of the device is sufficiently long to permit access to the particular desired target tissue through a laparoscopic port, while not being so unwieldy that it is difficult to control. The choice of dimension of the device is dependent on the particular user, the target tissue, the subject being treated, the agent being administered, and other factors within the level of a skilled artisan. Generally, the needle sheath 72, 72' or 72" of the injection device is of a sufficient length to permit laparoscopic access to the target of interest, and is generally a length of 200 mm to 600 mm, such as 250 to 400 mm, and generally at least or about at least or 300 mm.

In all aspects of the device provided herein, the syringe barrel 91, 91' or 91" is cylindrical in shape with a hollow center that can fit the plunger 92, 92' or 92" so that the plunger can move back and forth inside the syringe barrel. The syringe can be made out of plastic or glass or other suitable material. Generally, the syringe is made out of glass or plastic, such as polypropylene, polyethylene, or polycarbonate. Other types of biocompatible materials may also be used. The syringe barrel can contain calibrations or markings on the outer surface in order to measure or detect the volume of solution. The calibrations can be marked in any measurement such as in cubic centimeters (cc), milliliters (mL), tenths of a milliliter, hundredths of a milliliter or other measurement. The volume of the syringe barrel can be selected by the operator depending on the particular application, the agent being administered, the type of device that is being used and other similar factors. For example, the volume of the syringe barrel can depend on the desired amount of fluid, such as a therapeutic, to be delivered, which is generally between 200 μL and 10 mL, more typically 500 μL to 2.5 mL, such as at least 500 μL, 1 milliliter (mL), 2 mL, 2.5 mL, 3 mL, 4 mL, 5 mL, 6 mL, 7 mL, 8 mL, 9 mL, 10 mL or more. For example, the syringe barrel can be 0.5 mL to 20 mL (i.e. 0.5 cc to 20 cc), and generally is 0.5 mL to 3 mL (i.e. 0.5 cc to 3 cc), such as at least or about a 1 mL (i.e. 1 cc) syringe. The syringe barrel also can have unit calibrations, such as present on standard insulin syringes (e.g. 100 units correlates to 1 mL). Typically, 200 μL to 600 μL of the fluid, such as a therapeutic, is delivered to the target locus, and the volume of syringe barrel is 1 mL.

The syringe barrel 91, 91' or 91" is always positioned on the proximal side of the injection needle, but can be positioned on either side of the needle sheath controller and in a manner that is on the proximal or distal side of the needle sheath controller. For example, the syringe barrel can be positioned on the proximal side of the needle sheath controller, or inside the needle sheath 72, 72' or 72". In particular aspects, with reference to the Figures and description below, FIGS. 1A and 1B depict a device 60 where the syringe barrel 91 is proximal to the needle sheath controller 71. In contrast, FIG. 2 depicts a device 60' where the syringe barrel 91' is distal to the needle sheath controller 71' and is integrated with the needle sheath at its distal end. FIG. 3 depicts a device 60" where the syringe barrel 91" is distal to the needle sheath controller 71' and is dockable, and hence removable from, the needle sheath at the distal end.

In cases where sterile injections are required, the syringe barrel can be loaded with the fluid, such as a therapeutic, in a sterile environment, such as a sterile operating room, or a sterile pre-loaded syringe can be used. For example, a sterile standard or dockable syringe can be connected to the device after loading with the fluid, such as a therapeutic, in a sterile environment. In other cases, the entire device is loaded, manipulated and operated in a sterile environment.

The plunger is located at the proximal end of the device and is movable so that it can be pulled and pushed along the inside the syringe barrel. Portions of the plunger travel within the syringe barrel along the longitudinal axis of the device. The plunger is cylindrical to move through the syringe barrel, and is made of a material that permits ease of movement through the syringe barrel. For example, the plunger generally is made of a plastic, such as polypropylene or polyethylene. The plunger also contains a head at the proximal end of the device that can be conveniently grasped by the operator to manipulate the plunger. The plunger head can transmit axial force from the operator in both the distal or proximal directions, leading to depression and drawing back, respectively, of the plunger. The plunger can be drawn back to load the syringe barrel with the fluid, such as a therapeutic, or depressed to inject the fluid, such as a therapeutic, in the target tissue. Pulling back on the plunger draws in the fluid, such as a therapeutic, or air into the syringe barrel. Pushing in the plunger forces air or the fluid or air out of the syringe barrel. The plunger can also be pulled back at the site of injection to test needle placement.

The length of the plunger is sufficiently long to permit its association with the inside of the syringe barrel directly or indirectly in order to effect dispelling of the fluid, such as a therapeutic, or composition or solution through the distal end of the syringe (and into a needle or tube if connected thereto). For example, in some aspects herein, a control plunger that is accessible to the operator can be adapted to be used with an auxiliary plunger when the syringe barrel is distally located. The length of the plunger can be 5 mm to 500 mm, such as 10 mm to 300 mm, 10 mm to 200 mm or 10 mm to 100 mm. Depending on the positioning of the syringe barrel with reference to the needle sheath controller, in some aspects the plunger also traverses through the needle sheath controller. In particular aspects, with reference to the Figures and description below, FIGS. 1A and 1B depict a device 60 where the plunger 92 is a standard plunger that is sized to move only within the syringe barrel 91 located at the proximal end of the device relative to the needle sheath controller. In contrast, FIG. 2 depicts a device 60' where the plunger 92' is elongated to traverse through the needle sheath controller 71' and hollow lumen of the needle sheath before traveling through the syringe barrel 91' at the distal end of the device. In another aspect, FIG. 3 depicts a device 60" where the plunger 92" is elongated to traverse through the needle sheath controller 71' and hollow lumen of the needle sheath, but does not travel through the syringe barrel 92" at the distal end of the device. Instead, the plunger is adaptable with an auxiliary plunger 920 that is sized to move only with the syringe barrel located at the distal end of the device.

The plunger 92, 92' or 92" can be manually depressed or pulled back, or an automatic controller can be used to control the plunger. An automatic or mechanical plunger mechanism can deliver several fixed or variable doses of the fluid, such as a therapeutic, with or without having to remove the injection device from the laparoscopic port. For example, a means of depressing the plunger 92, 92' or 92" can include hydraulic components, such as mechanically or electronically actuated piston and cylinder assemblies operatively connected, via hydraulic fluid lines, to the respective plunger 92, 92' or 92" elements. The device can be used to deliver a single dose of the fluid, such as a therapeutic, or multiple injections to the same patient without withdrawing the device from the laparoscopic port. Multiple doses can be delivered at different injection sites, if the multiple sites are reasonably close to each other that removal from the laparoscopic port is not necessary. The injection of several discrete doses can be achieved using different controls, such as mechanical controls and hydraulic mechanisms. For example, hydraulic components, such as mechanically and/or electronically actuated piston/cylinder assemblies or hydraulic plunger actuators can be used to control the plunger, which permits the use of a stroke or a force multiplier, and also permits a flexible shaft for the plunger mechanism, to transmit axial force. For multiple injections, an indexed injection trigger is used to deliver discrete doses of the fluid, such as a therapeutic, for example 100 microliter (µL), upon each pull of the trigger. The doses for multiple injections can be fixed or variable, and a volume control or a feedback mechanism for dose control for multiple injections can be used. Multiple doses provide an advantage over a single large dose in that they can be manipulated by parameters such as the location of the tissue, geometrical parameters and temporal parameters.

In all aspects of the devices provided herein, the device contains an injection needle 81 that is located inside the sheath at the proximal end of the needle and can be sheathed and unsheathed at its distal tip. The injection needle typically contains a beveled tip sufficient to penetrate or pierce a tissue or an organ. The injection needle 81 can be directly or indirectly connected to the distal end of the syringe barrel in a manner that permits passage of a fluid or solution in the syringe barrel through the needle to its distal tip. For example, in some aspects, the injection needle 81 can be indirectly connected to the syringe barrel by an intermediary tube 83 that, together with the injection needle, form a continuous sealed fluid pathway for solution to move through. The intermediary tube can be a plastic or metal tube that is coupled directly or indirectly to the injection needle 81 by welding, bonding or molding. The intermediary injection tube 83 can be indirectly coupled to the injection tube 81 by a needle coupler 85. The needle coupler 85 can be made of any biocompatible and drug compatible rigid material, including metals, plastics, and ceramics, and is typically made of plastics such as polycarbonate or Acrylonitrile butadiene styrene (ABS). An optional coupling member 82 can be present inside the cavity of the needle coupler 85. The needle coupler 85 is coupled to each of the intermediary injection tube 83 and injection tube 81 by welding, bonding, molding or other procedure that creates a secure and reliable seal.

In some variations, the distal end of the syringe barrel can contain an adaptor that is compatible with a needle hub on the proximal end of the injection needle 81 or other intermediary tube 83 that itself is coupled to the injection needle 81. For example, with reference to FIG. 1A, and as described further below, the distal end of the syringe barrel 91 can contain a Luer fit adaptor 93 that is compatible with a needle hub 84 on the proximal end of intermediary injection tube 83, which itself is directly or indirectly connected to the injection needle 81. In other variations of the devices herein, the proximal portion of the injection needle 81 or other intermediary tube 83 that couples to the injection needle is directly affixed to the distal end of the syringe barrel and extends out of the syringe barrel. For example, with reference to FIGS. 2 and 3, the injection needle 81 is directly connected to the syringe barrel.

The size and diameter of the injection needle 81 is selected depending on the ease of insertion into tissue, damage to tissue that can be tolerated, shear/flow parameters of the fluid such as viscosity, injection force and injection rate required for the fluid, properties of the target tissue, amount of dead volume that remains in the device after injection, and other factors considered by persons skilled in the art. Typically, a small diameter needle 81 is employed to reduce the force required to insert the needle into the target tissue or organ, and to reduce trauma to the target tissue or organ. Generally, injection needle 81 is between 25 and 34 gauge, such as 25 gauge, 26 gauge, 27 gauge, 28 gauge, 29 gauge, 30 gauge or 31 gauge, and typically is 27 gauge.

The length of the injection needle 81 is dependent on the configuration of the syringe barrel in the device (i.e. whether the syringe barrel is located at the proximal or distal end of the device). The length of the injection needle 81 also is dependent on whether the needle is coupled directly to an intermediary injection tube 83 or is indirectly coupled to an intermediary injection tube 83 by a needle coupler 85. Such parameters can be related to the pressure drop that can be tolerated, the viscosity of fluid, the dead volume that can be tolerated, and other similar factors. For example, factors that influence pressure drop include the length of the needle, the diameter of the needle, and the viscosity of the fluid. A certain amount of injection pressure can be needed to deliver a fluid, such as a therapeutic, to a specific tissue. A specific injection pressure can be needed for delivery of certain fluid compositions. The injection pressure required can depend on factors such as parameters of the fluid being delivered such as viscosity, injection rate, and target tissue pressure.

For example, in some variations of the device, the injection needle 81 can be long and extend from the distal tip of the device through the sheath controller 71 where it is connected to syringe barrel 91 at the proximal end of the device. Hence, the length of the injection needle can range from 5 mm to 500 mm or more, such as 10 mm to 300 mm. Generally, in examples of the devices herein, the injection needle is shorter, which avoids problems in pressure drop that can occur when a solution is injected through a long needle. For example, the length of the injection needle generally can range from 5 mm and 40 mm, such as 10 mm to 40 mm. For example, common needle lengths that are widely available include for example, 12.7 mm, 25.4 mm or 38.1 mm needles. If a longer path is required for solution or fluid to travel (i.e. the syringe barrel is located at the proximal end of the device, e.g. FIGS. 1A and 1B), a smaller injection needle 81 can still be employed, but a pressure drop can be avoided by directly or indirectly coupling a smaller diameter injection needle 81 to an intermediary injection tube 83 of a greater diameter. For example, if the injection needle 81 is 27 gauge, the intermediary injection tube can be 15 gauge to 25 gauge, such as generally 20 gauge to 25 gauge, for example 21 gauge.

The injection needle 81 of the device is protected by a blunt, elongated needle sheath, which can sheathe and protect the needle prior to injection and unsheathe the needle at the site of injection. Hence, in all embodiments of the laparoscopic injection device provided herein, such as devices set forth in FIG. 1A, 1B, 2 or 3, the needle sheath 72, 72' or 72" is adapted so that the injection needle 81 can be sheathed and unsheathed. The ability to sheathe or unsheathe the injection needle 81 permits the operator of the device to control when the injection needle is exposed or when the injection needle is protected. For example, sheathing of the needle can prevent accidental injections or penetrations, damages to the patient's tissue, including the target tissue and non-target tissues, damages to the laparoscopic surgical instruments, such as damages to the elastomeric seals and valves of the laparoscopic port, damage to the needle, and accidental drip of the fluid, such as a therapeutic, during the insertion of the device into the laparoscopic port or removal of the device from the laparoscopic port. At the site of injection, the needle can be unsheathed, exposing the injection needle 81 to allow the needle tip to penetrate the target site and deliver the agent to the target site, such as the parenchyma of a target organ. The injection needle 81 can be sheathed again after injection to prevent accidental needle puncture of tissue other than the injection site.

In particular, the needle sheath 72, 72' or 72" is adapted to be controlled by the needle sheath controller 71 or 71'. The needle sheath controller 71 or 71' contains the components that control movement of the needle sheath 72, 72' or 72", connects the proximal and distal ends of the device, and is the conduit by which inner tubings, plungers or other components can travel between the proximal and distal ends of the device. The needle sheath controller 71 or 71' includes a controller housing 710 that encloses components internal to the needle sheath controller 71 or 71', and the proximal end of the needle sheath 72, 72' or 72". The needle sheath controller housing 710 can be made of any suitably resilient and rigid material, such as any polymeric material, including plastics, or rubber, metals, ceramics, composites, or other suitable material known to one of skill in the art. Typically, the needle sheath controller housing 710 is made from a plastic, including medical-grade plastics such as polypropylene, polystyrene, polyethylene, polyvinyl chloride, polyurethane, or silicone, rubber or acrylic. The needle sheath controller housing 710 can be molded using any technique known in the art, including compression-molding, thermoforming or injection-molding. The housing 710 can be made of one singular piece, using methods such as by an injection molding. Alternatively, the housing 710 can include multiple pieces that are separately manufactured and attached in a secondary process, such as with adhesive, locking joints, or other fasteners.

As shown in FIGS. 1A, 1B, 2 and 3, the needle sheath controller 71 or 71' is positioned on the proximal side of the needle sheath 72, 72' or 72". The needle sheath controller 71 or 71' is configured to be held and manipulated by an operator, such as a surgeon. The needle sheath controller 71 or 71' can be any shape and size that is convenient to permit the operator to hold and manipulate the device. Generally, the needle sheath controller 71 or 71' is cylindrical and can fit into the palm of an average person. The diameter of the needle sheath controller 71 or 71' is larger than the diameter of the needle sheath 72, 72' or 72" in order to accommodate the proximal end of the needle sheath 72, 72' or 72". For example, the diameter can be 15 mm to 100 mm, and is generally 20 to 35 mm. The diameter can be uniform or variable. For example, the outside of the needle sheath controller 71 or 71' can be graduated, contoured, beveled or grooved. The needle sheath controller 71 or 71' generally has a length of 30 mm to 225 mm, such as 50 mm to 75 mm. On the outside of the needle sheath controller 71 or 71', an optional grip can be present to facilitate the manipulation and handling of the device.

The needle sheath controller 71 or 71' contains an externally accessible positioner 711, which controls the position of the needle sheath 72 relative to the injection needle 81. As can be seen in FIGS. 1A, 1B, 2 and 3, the needle sheath controller 71 or 71' is a cylindrical ring having a positioner 711 extending out of the needle sheath controller 71 or 71' so that it is accessible to the operator. The positioner 711 can be integrally formed with the housing 710, or alternatively can be a separate piece coupled to the housing during assembly.

The positioner 711 is configured in the needle sheath controller 71 or 71' so that it is movable both forward and rearward relative to the needle sheath controller 71 or 71'. Movement of the positioner 711 forward or rearward controls movement of the needle sheath 72, 72' or 72" between two fixed or locked positions, the sheathed position 72a and unsheathed positions 72c. When sheathed, the injection needle 81 is hidden inside the needle sheath, and when unsheathed, the injection needle 81 is exposed outside of the needle sheath. The injection needle 81, however, is fixed and does not move relative to the needle sheath controller 71 or 71'. Thus, the positioner 711 only controls the movement of the needle sheath 72, 72' or 72", while the position of the injection needle 81 and other components of the device are stationary regardless of the position of the positioner 711. The relative position of the injection needle 81, however, changes with the movement of the needle sheath 72, 72' or 72", as the needle sheath 71 or 71' moves in the distal direction or the proximal direction, hiding or exposing the injection needle 81.

Figure 4A:
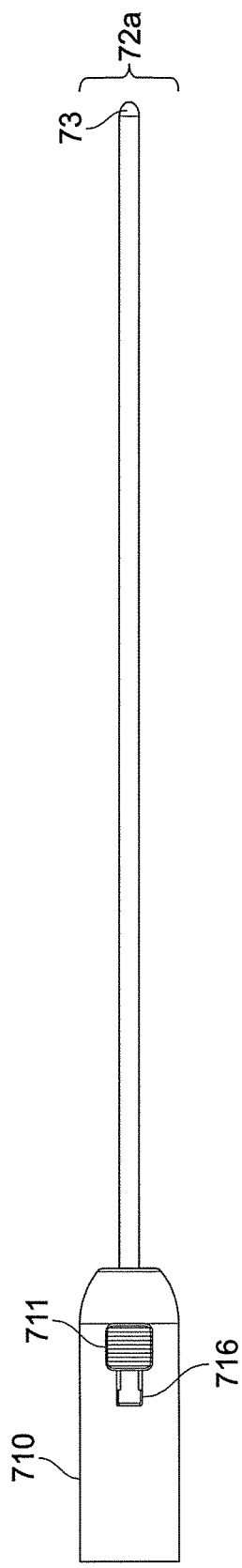
FIGS. 4A-C illustrate the movement of the needle sheath of the injection device between the sheathed and unsheathed position as controlled by the positioner.
Figure 4B:
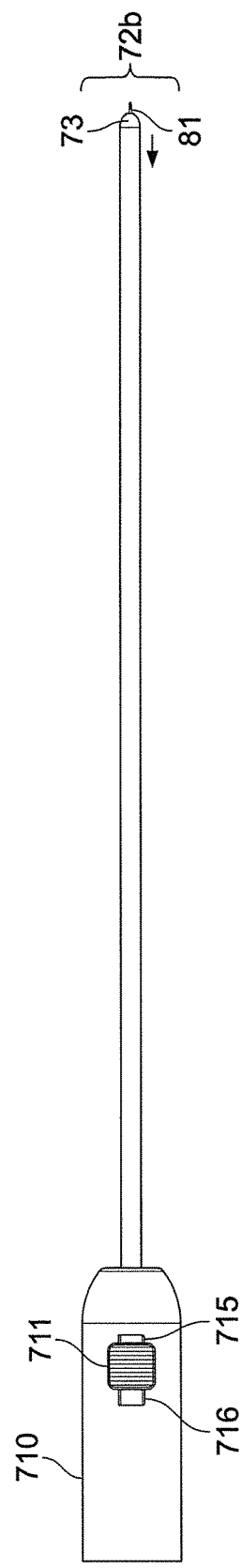

As shown in FIG. 4A, positioning of the positioner in a forward 711a position moves the needle sheath over the injection needle in the sheathed position 72a so that the injection needle is hidden inside the shaft of the needle sheath. As shown in FIG. 4B, positioning or moving the positioner to an intermediate position 711b, that is not fully locked forward or rearward, transitions the needle from outside of the needle sheath shaft to a transitional position 72b that exposes less of the needle than its maximum extent or length. As show in FIG. 4C, positioning of the positioner in the rearward 711c position moves the needle sheath proximally towards the needle sheath controller to its fully unsheathed position 72c, thereby permitting maximum exposure of the injection needle 81.

Figure 5:
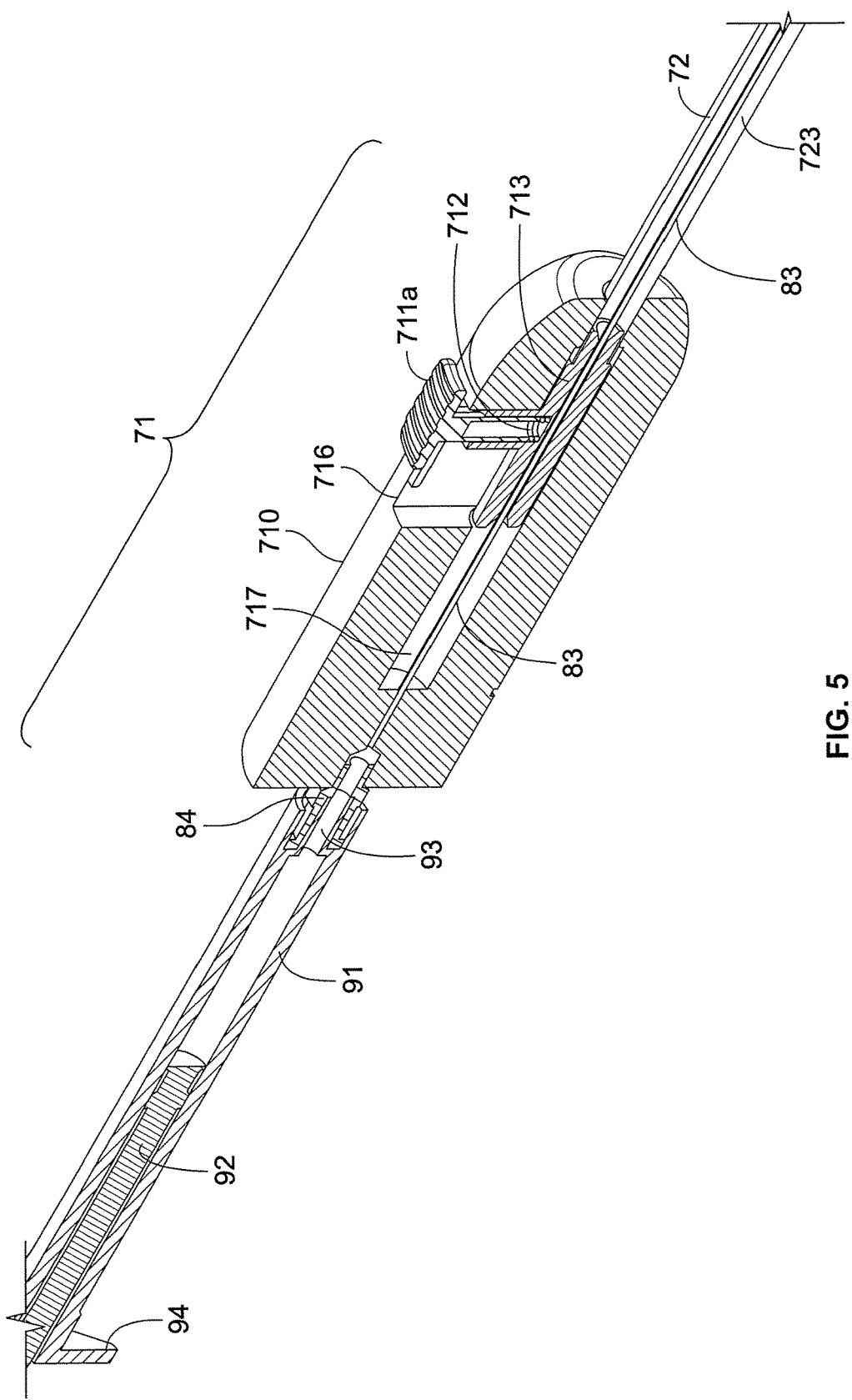
FIG. 5 is an enlarged sectional view of the needle sheath controller of the device depicted in FIGS. 1A and 1B.
Figure 6:
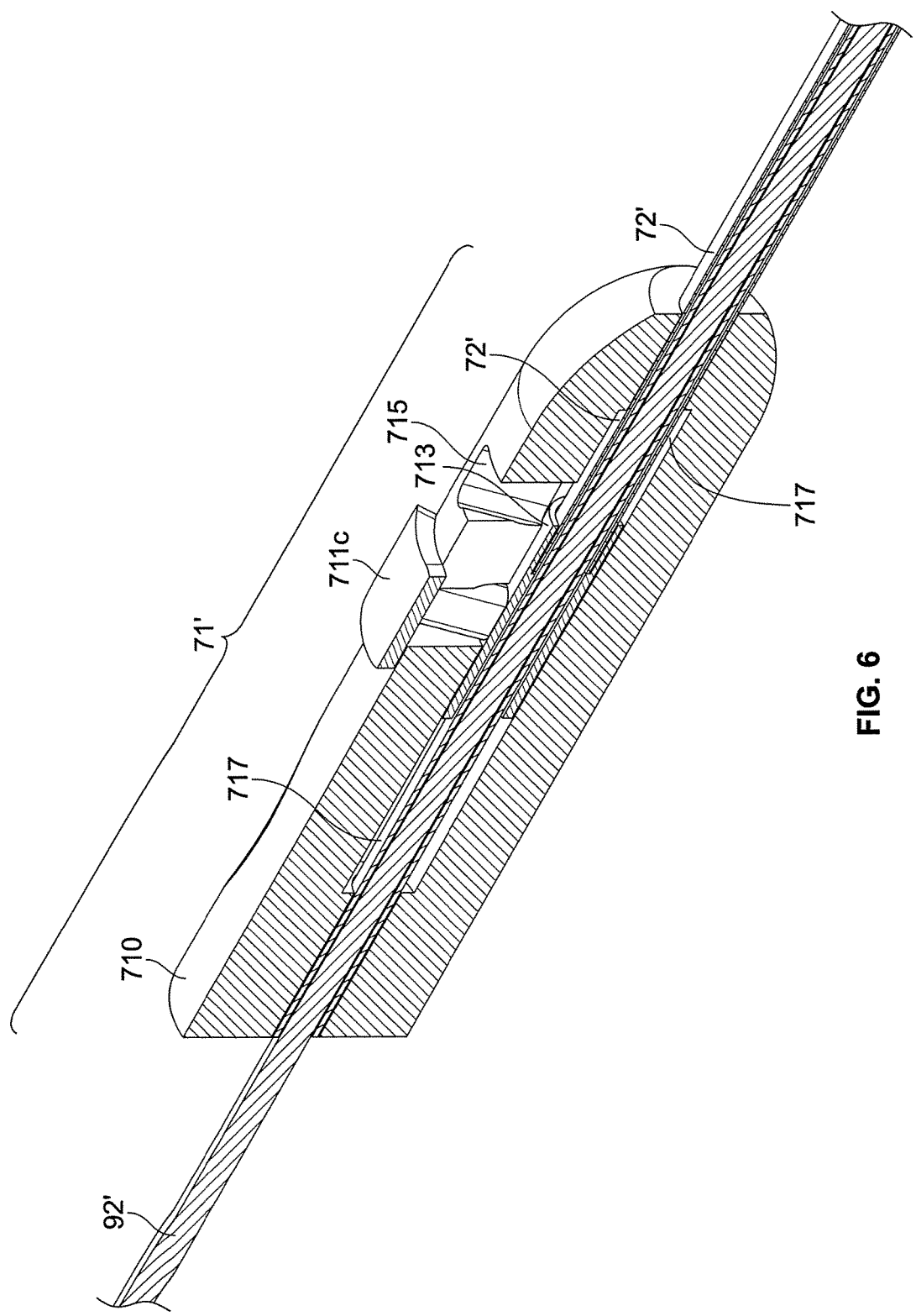
FIG. 6 is an enlarged sectional view of the needle sheath controller of the device depicted in FIG. 2.
Figure 7:
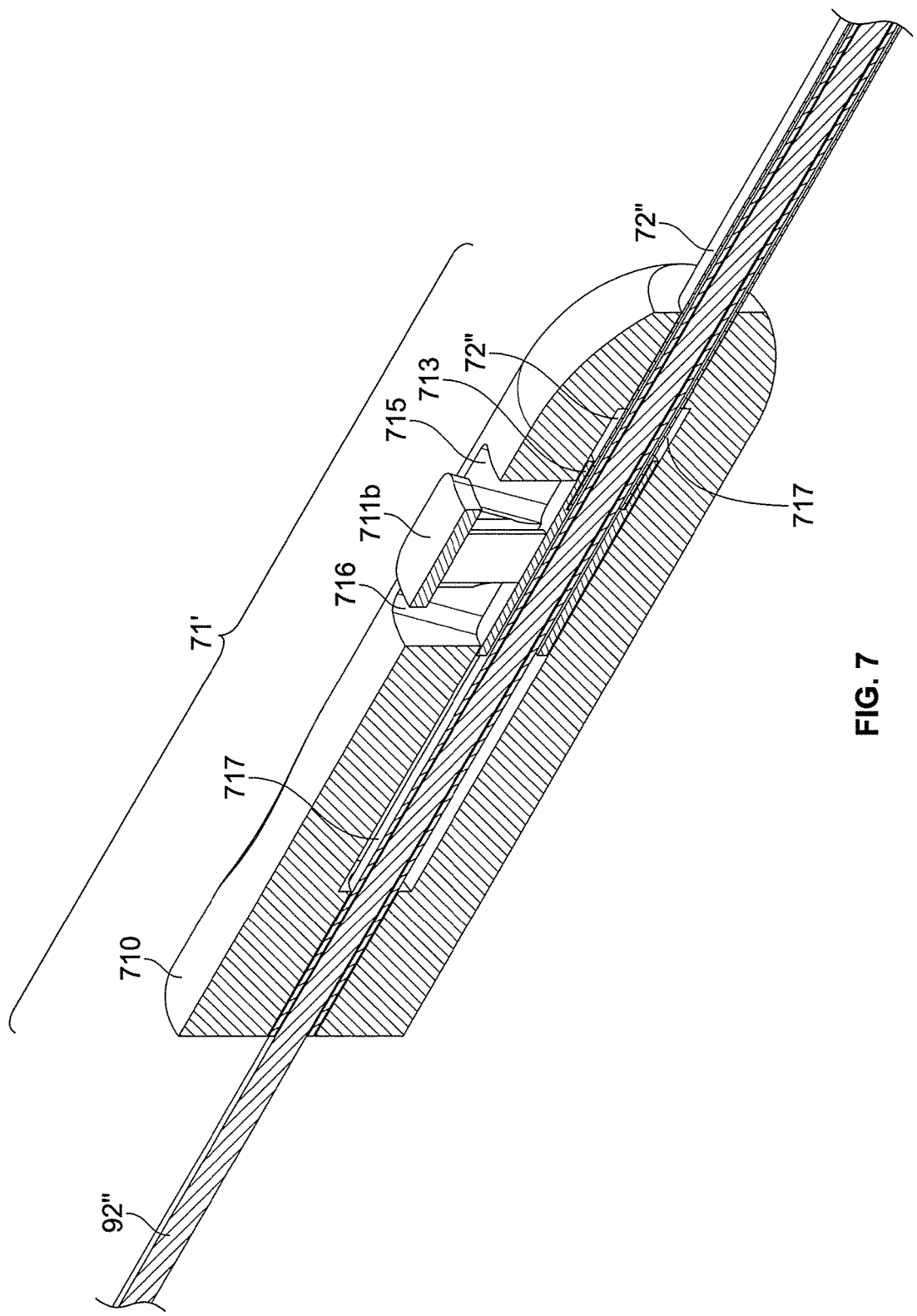
FIG. 7 is an enlarged sectional view of the needle sheath controller of the device depicted in FIG. 3.

The positioner 711 is engaged with the needle sheath and slides the needle sheath. As can be seen in FIGS. 5-7, the movement of the needle sheath 72, 72' or 72" by the positioner 711 is facilitated by a connection member 713. The connection member 713 is connected to the proximal end of the needle sheath 72, 72' or 72" and the lower part of the positioner 711. The positioner 711 and the needle sheath connector 713 can be connected to each other by welding, adhesive, locking joints, fasteners or other suitable means. The distal end of the connection member 713 is connected to the proximal end of the needle sheath 72, 72' or 72", such that the sheath is longitudinally movable relative to the controller housing 710 and the injection needle 81. In particular, the distal end of the outside of the connection member 713 is engaged with the proximal inside lumen 723 of the needle sheath around its circumference. The needle sheath 72, 72' or 72" can be connected to the connection member 713 by welding, adhesive, locking joints, fasteners or other suitable means.

The lower portion of the positioner 711, the connection member 713 and proximal end of the needle sheath 72, 72' or 72" are enclosed by the controller housing 710. With reference to FIGS. 5-7, the needle sheath controller housing 710 is molded with an internal needle sheath controller lumen 717 that is a hollow cavity inside the needle sheath controller 71 or 71' of a sufficient length and diameter to accommodate forward and rearward movement of the connection member 713. The length and diameter of the controller lumen 717, however, is always less than the total length and diameter of the needle sheath controller 71 or 71", thereby restricting movement of the needle sheath connector 713 within the inside of the needle sheath controller 71 or 71'. The controller lumen 717 is generally longitudinal along the housing body. The shape of the internal or central lumen 717 of the controller can be any of a variety of shapes and configurations, so long as it provides a tracking means along which the connection member 713 slides. For example, the controller lumen 717 can be cylindrical or rectangular. The controller lumen 717 also can be uniform or non-uniform in shape, size or diameter. For example, the distal and proximal ends can be the same diameter or different diameters.

The needle sheath controller housing 710 also contains cut-out grooves to serve as sheath stops 715 and 716 that provide a means to engage with the positioner 711. As shown in FIGS. 5-7, the positioner 711 contains a projected top portion or head that juts out of the needle sheath controller 71 or 71' where it can be moved forward or rearward by the operator. Internal to the needle sheath controller 71 or 71', the body of the positioner 711 is notched on its sides or is otherwise configured to engage with sheath stops. The sheath stops 715 and 716 are grooves in the needle sheath controller housing 710 that fit the notched body of the positioner and trap the positioner 711 so that it cannot be moved without external force.

The positioner 711 is configured to be lockable and releasable in the sheath stops 715 and 716, such that when the positioner is engaged in a sheath stop it is secure to prevent the sheath from moving, but can be conveniently repositioned to control the movement of the sheath. For example, the sheath stops can be configured in a manner that creates a cradle for the positioner so that the positioner 711 is secured within the sheath stop and is not able to fall out of the cradle in the stop. To move the positioner 711 out of the cradle in the stop, the positioner must be physically moved outward from the cradle, so that the positioner 711 can be repositioned. To lock the positioner, the positioner must be physically moved inward (towards the grooves or cradle in the stop) to engage with the cradle created in the stop. Thus, the positioner 711 can also be pivoted to move outward (away from the grooves or cradle in the stop) to unlock from the sheath stops 715 and 716, then slid along the longitudinal axis to change positions, and pivoted again to move inward (towards the grooves or cradle in the stop) to engage with and lock into the sheath stops 715 and 716 to lock the positioner 711 and the needle sheath 72.

As an alternative, the positioner 711 can contain a lock and release element that facilitates lock and release of the positioner with the grooves of the sheath stops. FIG. 5 depicts an optional lock and release element 712 that can be contained in the positioner to facilitate lock and release of the positioner 711 with the grooves of the sheath stops. For example, the lock and release element 712 can be a spring or other resilient means. When the positioner 711 is moved or fit into the grooves of a stop it is locked into place by a vertically upward force against the positioner 711 and a downward force against the connection member 713. Pressing the positioner 711 vertically downwards releases the vertically upward force applied by the lock and release element 712, and releases the positioner from the stops.

Because the positioner 711 and the connection member 713 are connected, the movement of the positioner 711 can control the movement of the connection member 713 and the connected needle sheath 72, 72' or 72". Therefore, movement of the positioner 711 between the sheath stops 715 and 716 moves the needle sheath 72, 72' or 72" between the sheathed and unsheathed positions. In other variations, the lock and release mechanism can be a latch or switch that can be selectively engaged or disengaged according to its mechanical nature, for example, by sliding a latch or pivoting a lever attached to the head of the positioner 711, thereby moving it out of the way of a notch or other fastening mechanisms in the groove of the sheath stops.

For example, with reference to FIGS. 5-7, the needle sheath controller housing 710 contains two sheath stops 715 and 716 that are arranged into the needle sheath controller housing 710 on the proximal and distal sides of the positioner 711. With reference to FIG. 5, when the positioner 711 is engaged in either of the sheath stops 715 or 716, the lock and release element 712, such as a spring, can exert a force against the positioner 711 in the vertically upward direction, and the connection member 713 in the downward direction. Unless force is applied against the lock and release element 712 by pressing the positioner 711 down, the positioner 711 and connection member 713 have a tendency to be pushed away from each other in the vertical direction, due to the force exerted by the lock and release element 712. The force that pushes the positioner 711 in the upward direction permits the positioner 711 to be locked in place in either the distal sheath stop 715 or the proximal sheath stop 716. If the positioner 711 is pressed vertically downward, the positioner 711 is freed from the grooves and can move in the forward or rearward direction longitudinally.

FIGS. 5-7 demonstrate the alternative positions of the positioner 711 relative to the sheath stops. For example, FIG. 5 depicts the positioner 711 in the forward position 711a where it is engaged or fit into the distal sheath stop 715. When the positioner 711 is engaged with distal stop 715, the connection member 713 is longitudinally moved to the furthest distal position within the controller lumen 717 and the sheath is in the extended position hiding the needle tip. FIG. 6 depicts the positioner 711 in the rearward position 711c where it is engaged or fit into the proximal sheath stop 716. When the positioner 711 is engaged with proximal stop 716, the connection member is longitudinally moved towards the proximal end of the needle sheath lumen, thereby exposing the injection needle. FIG. 7 depicts the positioner 711 in an intermediate position 711b after releasing the positioner from its locked position in either sheath stop and sliding the positioner along the longitudinal axis. In this position, the injection needle 81 is in an intermediate unsheathed position, but is not fully exposed.

The extent or length of the injection needle 81 that can be exposed or unsheathed at the distal end of the device is related to the distance along the longitudinal axis between a first sheath stop and a second sheath stop, which is the distance that the positioner 711, and hence connection member 713 controlling the position of the sheath, moves between locked positions. For example, with reference to FIGS. 5-7, the extent or length of the injection needle 81 that can be exposed or unsheathed at the distal end of the device can be substantially the same as the distance between the distal sheath stop 715 and the proximal sheath stop 716. It is understood, however, that the extent or length of the injection needle that is exposed can be somewhat longer or shorter than the distance between the first and second groove stop due to a slight recess of the distal tip of the injection needle in the distal tip of the needle sheath when it is unsheathed. For example, if the distal tip of the injection needle 81 is recessed from the distal tip of the needle sheath 73 in the fully sheathed position 72c, the extent or length the injection needle that can be exposed is shorter than the distance between a first sheath stop and a second sheath stop. A needle that is exposed substantially the same as the distance between the sheath stops is recessed only slightly and no more than 1 mm, such that the difference in the distance of the sheath stop and the length that the injection needle that can be exposed is less than 1 mm or 0.5 mm or less. As an example, if the distal tip of the injection needle 81 is slightly recessed from the distal tip of the needle sheath 73 in the fully sheathed position 72c, the maximum extent or length of the injection needle that can be exposed or unsheathed at the distal end of the device is the distance between the distal sheath stop 715 and the proximal sheath stop 716, minus the slight distance between the tip of the injection needle 81 and the distal tip of the needle sheath 73 in the fully sheathed position.

In other examples, the length of the injection needle that is exposed or extended is appreciably shorter than the distance between the sheath stops. In this case, the injection needle can be positioned so that it is recessed inside the distal tip of the needle sheath 73 in the unsheathed position 72c more than 1 mm, and generally 2 mm to 5 mm, from the distal tip of the needle sheath 73 in the unsheathed position 72c. Thus, if the distal tip of the injection needle 81 is recessed from the distal tip of the needle sheath 73 in the fully sheathed position 72c, the maximum extent or length of the injection needle that can be exposed or unsheathed at the distal end of the device is the distance between the distal sheath stop 715 and the proximal sheath stop 716, minus the distance between the tip of the injection needle 81 and the distal tip of the needle sheath 73 in the fully sheathed position.

The extent or length of the injection needle 81 that is exposed when unsheathed can be empirically determined, and is a function of the target tissue, the particular subject being treated, the agent being administered and other factors within the level of a skilled artisan. For example, the extent of the injection needle that is unsheathed is of a sufficient length so that the needle tip can penetrate the parenchyma of the target tissue of interest, but not so long that it can easily pass through or puncture the target tissue through to the other side. Typically, the desired length of the exposed injection needle when unsheathed is from or from about 2 mm to 10 mm, such as generally 5 mm to 10 mm. For example, general adult tissues, such as the liver, have a thickness of 10 mm to 30 mm. The thickness of the tissue can vary depending on the anatomical dimensions of the subject, such as age, height, weight, and/or the type of tissue or organ. Hence, the distance between the distal sheath stop 715 and the proximal sheath stop 716 is 2 mm to 15 mm, such as 2 mm to 12 mm, 2 mm to 10 mm, such as generally 5 mm to 10 mm.

In variations of the injection devices herein, more than two sheath stops, such as 3, 4, 5 or more sheath stops, can be configured into the needle sheath controlling housing 710 that can each engage separately with the positioner 711 to lock the sheath. Engagement of the positioner with the most distal sheath stop locks the sheath in its fullest extended position to completely hide the injection needle inside the needle sheath. Engagement of the positioner with the most proximal sheath stop locks the sheath in its fullest retracted or opened position to maximally expose the injection needle outside of the needle sheath. The other sheath stops provide means to vary the length of the exposed injection needle from its fully sheathed or unsheathed positions. Hence, the length of the exposed injection needle 81 can be varied with use of multiple needle sheath lock grooves. For example, in addition to the proximal 715 and distal 716 needle sheath stops, several additional sheath stops can be present, between the proximal and distal stops, permitting the positioner 711 and the needle sheath 72, 72' or 72" to be locked in several different positions, with different lengths of the injection needle 81 exposed. As an example, the controller housing 710 can contain four sheath stops that are separated along the longitudinal axis by a distance of 2 mm. Thus, the positioner 711 can be locked in four different positions, resulting in positioning of the injection needle so that it can be sheathed, or exposed by 2 mm, 4 mm or 6 mm.

The connection member 713 contains a central cavity that is also longitudinal along the housing body and is of a sufficient size to slide around and independently from components of the device that traverse through the needle sheath controller 71, 71' or 71". For example in FIGS. 5-7, an injection tube or plunger can traverse through the inside of the needle sheath controller across its longitudinal axis. In particular, FIG. 5 shows an intermediary injection tube 83 that traverses through the inside of the needle sheath controller, and the connection member 713 contains a central cavity that slides around and independently from the injection tube 83. The injection tube 83 is fixed to the needle sheath controller 71 at its proximal end. As shown in FIGS. 6-7, the plunger 92' or 92", respectively, longitudinally traverses through the inside of the needle sheath controller 71', and the connection member 713 contains a central cavity that accommodates and slides around and independently from the plunger 92' or 92". The plunger is movable within the needle sheath controller 71' and is not fixed thereto. The particular width or size of the cavity is dependent on the particular component that traverses through it. The connection member 713 is disengaged from and moves independently with respect to the components (e.g. injection tube or plunger) that run through its internal central cavity.

In aspects of the injection device provided herein, the needle sheath optionally has a visibility window, allowing visualization of the drawback fluids to test needle placement in target organs. For injections into the parenchyma of a target organ that has extensive vasculature, the drawback fluid can be used to confirm needle placement into the parenchyma, and avoid injections into the vasculature or the bile duct. At the site of injection, the plunger can be pulled back slightly to draw a small amount of fluids, in order to determine whether the needle was placed at a blood vessel or the target organ. Once the needle 81 is positioned and has penetrated the target injection site, the plunger 92, 92' or 92" can be depressed to deliver the fluid, such as a therapeutic, contained in the syringe barrel to the target site.

The syringe barrel 91, 91' or 91" and/or the device can be disposable or reusable. For example, except if the syringe is integrated with the device, the syringe barrel can be removed after injection or exhaustion of the fluid, such as a therapeutic, replaced with a new loaded syringe, or reloaded and re-connected. If the syringe barrel is at the outside the laparoscopic port, such as described with device 60, this can be achieved without the need to withdraw the device from the laparoscopic port. In some cases, the device can be withdrawn from the laparoscopic port and disposed of after one use. The method of loading and the type of syringe and syringe format employed can be empirically determined and is a function of factors considered by persons of skill in the art, such as the objective of the injection, target tissue or organ, dose and frequency of injections needed, properties of the fluid, such as a therapeutic, composition, and surgical environment.

For clarity of description, exemplary embodiments of the injection device are described below. It is understood that for the described embodiments, general aspects and components of the device are the same, and that different aspects or components are so described. Thus, except as noted, the description of the various exemplary embodiments and the structures of the embodiments described above apply to all embodiments of the injection device. Additionally, the methods of using the injection device, for example for injection of a fluid, such as a therapeutic, to a target tissue during a minimally invasive procedure, apply to all embodiments as well. The particular injection device employed can be empirically determined and is a function of factors considered by persons of skill in the art, such as the objective of the injection, target tissue or organ, dose and frequency of injections needed, properties of the fluid, such as a therapeutic, composition, and surgical environment.

1. Standard Injection Device

FIGS. 1A-B, 5, 8A-B, and 9A-D depict the injection device 60 and components and features thereof. The injection device as shown in FIGS. 1A and 1B includes needle sheath 72, needle sheath controller 71, injection needle 81, syringe barrel 91 and plunger 92. With reference to FIG. 1A, generally, the needle sheath 72 of the injection device is of a sufficient length to permit laparoscopic access to the target of interest, and is generally a length of 200 mm to 600 mm, such as 250 to 400 mm, and generally at least or about at least or 300 mm. The device is generally cylindrical around the longitudinal axis, generally having a smaller diameter in the needle sheath 72 region and the plunger 92 region, and a larger diameter in the needle controller 71 region. The needle sheath 72 portion of the device is typically inserted through the laparoscopic port. The diameter of the needle sheath 72 is typically between 3 mm to 12 mm in size, and typically from 5 mm to 10 mm. It is understood that the portions of the device external to the laparoscopic port can have a diameter greater than 10 mm. For example, the needle sheath controller body 71 can have a diameter sufficiently large, so long as it can be easily gripped or handled by the operator. The needle sheath controller body 71 is held by the operator, typically a surgeon, to manipulate and position the device 60, control the needle sheath 72, and support the device while manipulating the plunger 92.

The syringe barrel 91 is cylindrical in shape with a hollow center that can fit plunger 92 so that the plunger can move back and forth inside the syringe barrel. The syringe barrel is generally clear and transparent. The syringe barrel 91 can be made out of plastic or glass or other suitable material, and in particular is made out of plastic such as polypropylene, polyethylene, polycarbonate or other clear material. As described above, the syringe barrel 91 can contain calibrations or marking on the outer surface to indicate the volume of the agent within the barrel. As described above, the syringe barrel 91 can have a volume capacity that is from the range of 0.5 mL to 20 mL (i.e. 0.5 cc to 20 cc), and generally is 0.5 mL to 3 mL (i.e. 0.5 cc to 3 cc), such as at least or about a 1 mL (i.e. 1 cc) syringe. Typically, 200 µL to 600 µL of the fluid, such as a therapeutic, is delivered to the target locus, and the volume of syringe barrel is 1 mL.

The syringe barrel 91 is positioned proximal to the injection needle 81, and on the proximal side of the needle sheath controller 71. As shown in FIG. 1A, the distal end of the syringe barrel 91 contains a Luer fit adaptor 93 that is compatible with a needle hub 84 on the proximal side of the needle sheath controller 71. The syringe barrel 91 is removable and attachable with the needle sheath controller 71 and the connected needle sheath 72 by manipulation of the Luer fit locking mechanisms. FIG. 1A shows the syringe in the detached position 900a. Thus, a sterile syringe barrel 91 can conveniently be used when drawing up or loading the syringe with a fluid, such as a therapeutic, compositions or other solutions into the syringe barrel. If desired, a separately sterile needle can be fitted on the Luer fit adaptor 93 to permit loading of the syringe barrel 91 with a fluid, such as a therapeutic. After the agent is drawn up into the syringe, the syringe barrel 91 (without needle) can be secured to the needle sheath controller 71 through the Luer fit adaptor 93 on the distal end of the syringe barrel 91 and the needle hub 84 on the proximal end of the needle sheath controller 71. In some cases, a pre-loaded syringe a with standard Luer fit adaptor 93 can be connected. FIG. 1B shows injection device 60 with the syringe barrel 91 secured to the needle sheath controller, in the connected position 900b. Advantages of device 60 having a removable and attachable syringe barrel 91 include the ease of loading the syringe barrel and exchange of loaded syringe. Since standard syringes can be used to connect to the needle sheath control 71, a variety of syringe types can be used, and several different types of syringes can be used for one patient, if necessary. In cases where the syringe must be re-loaded or additional fluid is needed, new or re-loaded syringes can easily be connected.

The plunger 92 is located on the proximal end of the device 60 and is movable so that it can be pulled and pushed along the inside of the syringe barrel 91. The plunger 92 can be drawn back to load the syringe barrel 91 with the fluid or depressed to inject the fluid in the target tissue. The plunger 92 can also be pulled back at the site of injection to test needle placement. The plunger is cylindrical to move through the syringe barrel 91, and is made of a material that permits ease of movement through the syringe barrel, such as a plastic, for example polypropylene or polyethylene. The plunger contains a head 95 at the proximal end of the device that can be conveniently grasped by the operator to manipulate the plunger. The plunger head 95 also is generally made of plastic. The distal tip of the plunger 92 is generally made of silicone or other natural or synthetic rubber to provide a tight seal within the syringe barrel 91 when traveling within the syringe barrel 91.

The plunger 92 is long enough in length to permit its association with the inside of the syringe barrel 91 in order to dispel the fluid through the distal end of the syringe (and into a needle or tube if connected thereto). For example, the plunger is 5 cm to 50 cm, such as 5 cm to 30 cm or 10 cm to 20 cm. Pulling back on the plunger 92 draws in the fluid, such as a therapeutic, or air, and pushing the plunger 92 forces the fluid, such as a therapeutic, or air out of the syringe barrel. Optionally, the plunger can contain syringe barrel base 94 that can aid manipulation of the syringe barrel 91 with respect to the plunger 92.

The syringe barrel 91 and/or the device 60 can be disposable or reusable. For example, the syringe barrel 91 connected to the proximal side of the needle sheath controller 71 through a Luer fit adaptor 93, can be removed after injection of the fluid, such as a therapeutic, replaced with a new loaded syringe, or reloaded and re-connected, with or without the need to withdraw the device from the laparoscopic port. The device 60 can be withdrawn from the laparoscopic port and disposed of after one use.

The device 60 contains an injection needle 81 that is located inside the needle sheath 72 that can be sheathed and unsheathed at the distal tip of the needle 81. With reference to FIG. 1A, the distal tip of the needle sheath 73 contains a needle channel 733 that guides the needle outside of the needle sheath 72 when it is unsheathed as shown in FIG. 1B. As shown in FIG. 1B, the injection needle 81 contains a beveled tip sufficient to penetrate or pierce a tissue or an organ.

FIG. 5 depicts an enlarged cross section view of the distal end of the syringe barrel 91 and the needle sheath controller 71. As shown in FIG. 5, the plunger 92 is contained within the syringe barrel 91, which optionally can contain a syringe base 94, where it can movably travel. The needle sheath controller 71 is positioned on the proximal side of the needle sheath 72. The needle sheath controller 71 contains the components that control movement of the needle sheath 72, connect the proximal and distal ends of the device, and is the conduit by which the injection needle 81, directly or indirectly connected to an intermediary injection tube 83, travel between the proximal and distal ends of the device. The needle sheath controller 71 is configured to be held and manipulated by an operator, such as a surgeon. As discussed above, the needle sheath controller 71 can be any shape and size that is convenient to permit the operator to hold and manipulate the device, and typically is cylindrical in shape. The diameter of the needle sheath controller 71 is such that it can be held in the palm of an average adult, and is generally 20 mm to 100 mm in diameter with a length of 50 mm to 225 mm. The needle sheath controller 71 optionally can contain an outside grip for handling.

As shown in FIG. 1A-B and FIG. 5, the needle sheath controller 71 includes a controller housing 710 that encloses components internal to the needle sheath controller 71, and the proximal end of the needle sheath 72. As discussed above, the needle sheath controller housing 710 can be made of any suitably resilient and rigid material, such as any polymeric material, including plastics, or rubber, metals, ceramics, composites, or other suitable material known to one of skill in the art. The controller housing 710 is typically made of polypropylene, polystyrene, polyethylene, polyvinyl chloride, polyurethane, silicone, rubber or acrylic. As discussed above, the housing 710 can be made by any manufacturing known to a skilled artisan, and can be made as one singular piece or can be made of two or more pieces that are attached together, such as with adhesive, locking joints or fasteners.

As shown in FIGS. 1A and 1B, the needle sheath controller 71 contains an externally accessible positioner 711. As described above, the positioner 711 is configured in the needle sheath controller 71 so that it is movable both forward and rearward relative to the needle sheath controller 71. As described above, the positioner 711 is engaged with the needle sheath 72 through a connection member 713, and can be used to slide the needle sheath 72. This connection permits movement of the positioner 711 between the forward or rearward positions to control movement of the needle sheath between two fixed or locked positions, the sheathed and unsheathed positions. The sheathed position protects or hides the injection needle, while the unsheathed position exposes the needle.

With reference to FIG. 5, the connection member 713 is connected to the proximal end of the needle sheath 72, and the lower part of the positioner 711. The connection of the connection member 713 with the proximal end of the needle sheath is such that the needle sheath 72 is longitudinally movable relative to the controller housing 710 and the injection needle 81. For example, the distal end of the outside of the connection member 713 is engaged with the proximal inside cavity of the needle sheath 72 around its circumference. The connections of the control member 713 with the positioner 711 and needle sheath 72 can be by welding, adhesive, locking joints, fasteners or other suitable means.

As described above generally, the connection member 713 moves inside a hollow cavity or lumen 717 contained inside the housing 710 of the needle sheath controller 71 that is closed at both ends relative to the housing 710. The controller lumen 717 accommodates the connection member 713 such that the connection member 713 can easily glide or move forward or rearward in a restricted manner. For example, the connection member 713 can be cylindrical and fit inside a cylindrical hollow lumen cavity 717. As shown in FIG. 5, and discussed further below, the connection member 713 contains an internal hollow cavity to fit the injection tube 83 that passes through.

Movement of the connection member 713 is controlled by the positioner 711. As shown in FIGS. 1A, 1B and 5, the positioner 711 contains a projected top portion or head that juts out of the needle sheath controller 71 where it can be moved forward or rearward by the operator. As shown in FIG. 5, internal to the needle sheath controller 71, the body of the positioner 711 is notched on its sides or is otherwise configured to engage with sheath stops 715 or 716. Sheath stops 715 and 716 are grooves in the needle sheath controller housing 710 that fit the notched body of the positioner and trap the positioner 711 so that it cannot be moved.

FIG. 5 depicts the optional lock and release element 712 configured in the positioner 711 to facilitate lock and release of the positioner with the grooves of the sheath stop 715 or 716. For example, the lock and release element 712 can be a spring or other resilient means. The mechanism controlling lock and release of the positioner 711 with the grooves of the sheath stop 715 or 716 by the lock and release element 712 is as described above, whereby downward, vertical or lateral forces release or lock the positioner 711 from the sheath stops 715 or 716. Pushing downward on the positioner 711 permits the positioner to slide and to fit it into either of sheath stops 715 or 716.

Movement of the positioner 711 between the sheath stops 715 and 716 moves the connection member 713, and thereby also moves the needle sheath 72 so that it can transition from the sheathed and unsheathed positions by control of the positioner by the operator. When the positioner is in the forward position 711*a* as exemplified in FIG. 5, proximal sheath stop 716 is free and the positioner 711 is fit into the distal sheath stop 715, thereby sheathing the injection needle so that it is protected. While not shown in FIG. 5, the positioner 711 also can be in the rearward position 711*c* as exemplified in FIG. 6, where the distal sheath stop 715 is free and the positioner 711 is fit into the proximal sheath stop 716, thereby unsheathing the injection needle so that it is exposed. As a further position, the positioner 711 also can be in an intermediate position 711*b* as exemplified in FIG. 7, where both the distal sheath stop 715 and the proximal sheath stop 716 are free and not engaged with the positioner 711.

The injection needle 81 shown in FIG. 1B is indirectly connected to the syringe barrel 91 through an intermediary injection tube 83 as shown in FIGS. 1A and 5. The injection tube 83 contains a proximal needle hub 84 that is secured with the Luer fit adaptor 93 of the syringe barrel 91. The injection tube 83 is fixed directly to the needle sheath controller housing 710 so that the injection tube, and hence injection needle coupled thereto at the distal end of the device, is not movable.

As shown in FIG. 5, the injection tube 83 passes through the inside lumen 717 of the needle sheath controller 71 and passes through a central cavity of the connection member 713, but is not directly attached to the connection member. Hence, the connection member 713 can move independently around the fixed injection tube 83. As discussed above, because the needle sheath 72 is directly connected to the connection member 713 contained in the controller lumen 717, the injection tube 83 enters the lumen 723 of the needle sheath 72 inside the needle sheath controller 71. The injection tube 83 exits the distal end of the needle sheath controller 71 where it is contained within the hollow cavity of the needle sheath 72.

Figure 8A:
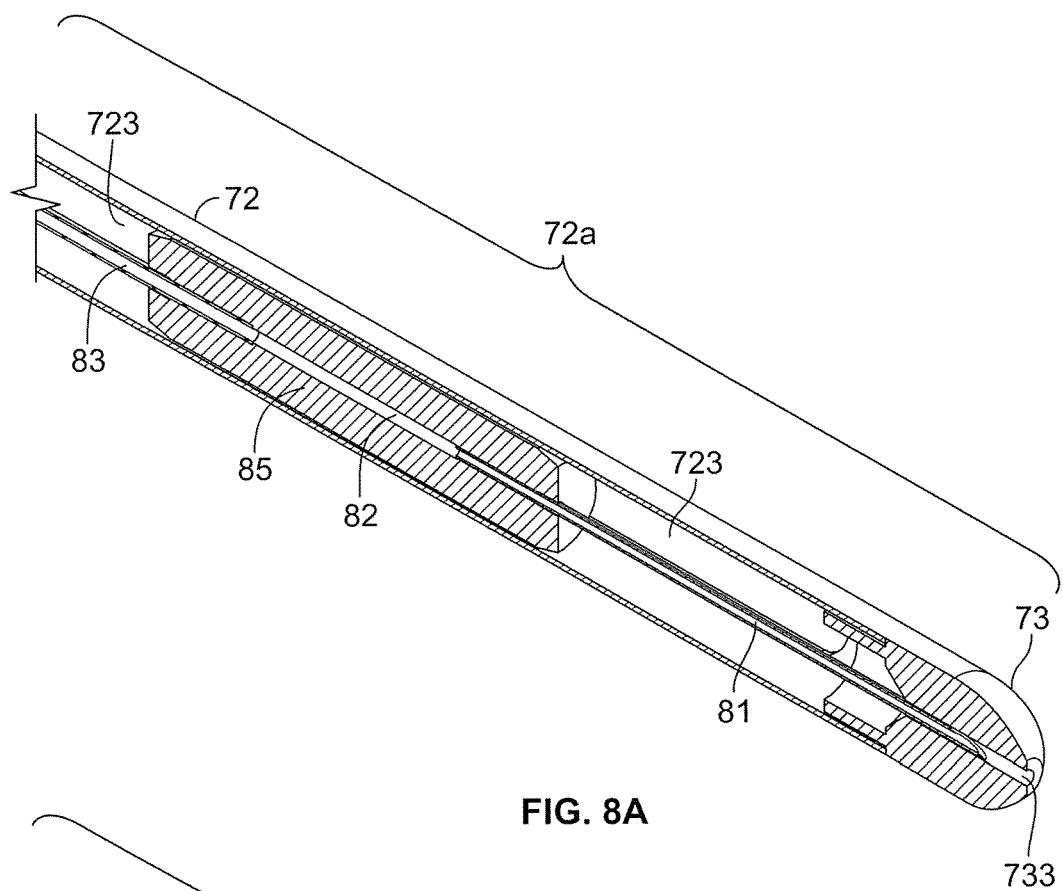
FIGS. 8A-8B show an enlarged sectional view of the tip of the needle sheath in the device shown in FIGS. 1A and 1B.
Figure 8B:
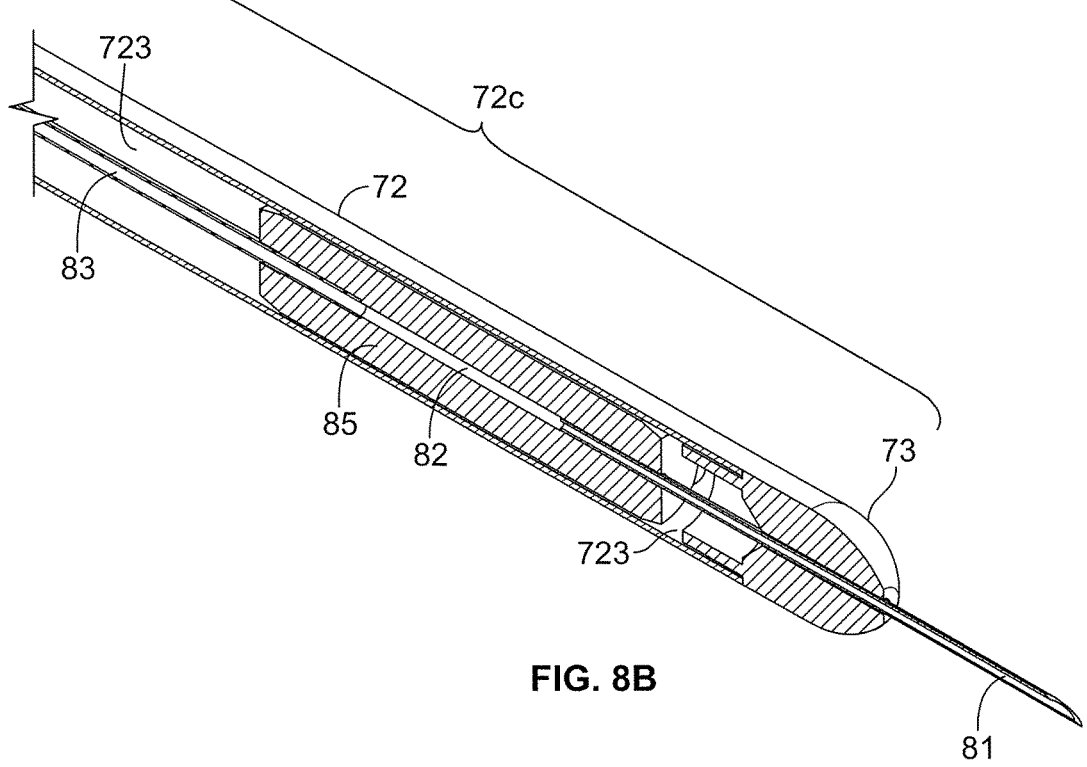

With reference to FIGS. 8A and 8B, the injection tube 83 runs distally and longitudinally through the needle sheath 72 where it is connected to the injection needle 81. The injection tube 83 and the injection needle 81 can be made of one piece, or made of more than one separate pieces. When the injection tube and injection needle 81 are made of one piece, the injection tube 83 can also be an elongated tapered needle, having a larger diameter in the proximal region, and a smaller diameter in the distal region near the injection needle 81. Optionally, a needle coupler 85, made of the same or different material, can be used to indirectly connect the two parts. The injection tube 83 and injection needle 81 can be made of the same material, or of different material. The injection tube 83 and the injection needle 81 have the same diameter, or a different diameter.

As shown in FIGS. 8A and 8B, the injection tube 83 is indirectly coupled to the injection needle 81 through a needle coupler 85. The coupler 85 connects the injection tube 83 to the injection needle 81 to form a continuous sealed fluid pathway for solution to move through. The connection can be by welding, bonding, molding or other procedure that creates a secure and reliable seal. The coupler 85 can be made of any biocompatible and drug compatible material suitable to provide a seal, and generally is made of a plastic. The coupler 85 can be clear or transparent or opaque. For example, the coupler 85 can be made of polycarbonate or other clear material. As discussed further below, in embodiments where the needle sheath 72 contains an optional visibility window 724 to view drawn up fluids, the needle coupler 85 generally is clear or transparent to permit visualization of the fluid or solution through the window.

The injection needle 81 contains a beveled tip sufficient to penetrate or pierce a tissue or an organ. The injection needle 81 is typically made of metal or alloy, such as surgical stainless steel or other medical grade metal. The size and diameter of the injection needle 81 is selected based on parameters described above. As described above, typically a small diameter needle 81 is employed to reduce the force required to insert the needle into the target tissue or organ, and to reduce trauma to the target tissue or organ. For example, the injection needle 81 is between 25 and 34 gauge, such as a 25 gauge, 26 gauge, 27 gauge, 28 gauge, 29 gauge, 30 gauge or 31 gauge needle, and typically is 27 gauge.

The gauge of the injection tube 83 can be the same or different than the injection needle 81. The device provided herein is generally designed, however, to minimize pressure drop throughout the path that the fluid traverses. Factors that influence the pressure within the column of fluid includes the length of the needle, viscosity of the fluid contained within, rate of delivery of the fluid, and the gauge of the needle. The device is designed to have reasonable axial force requirements to depress the plunger 92, thereby permitting delivery of the fluid in a laparoscopic manner with sufficient injection pressure. For example, the axial force required to depress the plunger 92 in order to inject the fluid to the target organ is typically less than 2 pounds of force (lbf), preferably less than 1 lbf. The axial force required to depress the plunger 92 can also depend on the desired rate of delivery of the fluid, and the optimal pressure can also depend on the operator. In some cases, a significant injection force can be required to inject the fluid through a long needle of the laparoscopic device. To prevent an immediate significant pressure drop when the fluid traverses the injection tube 83, a larger gauge injection tube can be used. Thus, in order to reduce pressure drops that can occur due to the long path created by the continuous sealed fluid pathway made up of the injection tube 83, coupler 85 and injection needle 81, the injection tube 83 generally has a larger diameter than the injection needle 81.

For example, if the syringe barrel 91 is positioned at least 300 mm proximal to the injection needle 81, and the fluid, such as a therapeutic, must traverse a long path through the needle sheath shaft 72, a significant pressure drop can occur. In this case, an injection tube 83 of a larger diameter can be used, coupled to an injection needle 81 with a smaller diameter, to prevent the large pressure drop when traversing through a narrow needle 80. An optional needle coupler 85 can be used to join the injection tube 83 with the injection needle 81. The needle coupler 85 contains a recess by which the injection tube 83 and the injection needle 81 can be press fit to stably hold the position of the needle components in place within the needle sheath lumen 723. The needle coupler 85, can optionally contain a coupling member 82 to facilitate coupling of the injection tube 83 and the injection needle 81 in the recess of the needle coupler 85.

If the gauge of the injection tube 83 and injection needle 81 are different, the coupler 85 can be sized to fit the opposing diameters, for example, it can be beveled on its proximal or distal end. In particular examples, the injection tube 83 is 15 gauge to 25 gauge, and the injection needle 81 is 25 gauge to 34 gauge. For example, the injection tube 83 is 21 gauge and the injection needle 81 is 27 gauge. The injection tube 83 can be made of metal or plastic, such as any surgical grade materials. The combined length of the injection tube 83, coupler 85 and injection needle 81 is sufficiently long to pass from the distal end of the syringe barrel 91 to the distal end of the needle sheath 72, for example is 100 mm to 600 mm long, and generally at least or about at least 300 mm. The particular size of the injection tube 83, coupler 85 and injection needle 81 can be chosen by the user and can depend, for example, on the convenience of available injection needles. For example, commonly used injection needles are sized as 12.7 mm, 25.4 mm or 38.1 mm needles.

The continuous sealed fluid pathway formed by the injection tube 83, coupler 85 and injection needle 81 pass through and traverse the central inside hollow cavity or lumen 723 of the needle sheath 72. The needle coupler 85 also holds the injection tube 83, and injection needle 81, so that the needle sheath 72 can slide over the injection tube 83, needle coupler 85 and injection needle 81 when the sheath is moved between the sheathed position 72a and unsheathed position 72c. For example, the needle coupler 85 is loosely fit into the hollow circular sheath lumen 723. Thus, the needle sheath 72 moves independently from the needle coupler 85. The needle coupler 85 can be made of any biocompatible and drug compatible rigid material, including metals, plastics, and ceramics, and is typically made of plastics such as polycarbonate or Acrylonitrile butadiene styrene (ABS). The injection tube 83 and injection needle 81 can be press fit into the recess of the needle coupler to create a stable fixed relationship with the needle coupler 85, and hence also the housing 710. An optional coupling member 82 can be present inside the recess of the needle coupler 85 and can be connected to the injection tube 83 and injection needle 81. The coupling member 82 is coupled to each of the intermediary injection tube 83 and injection tube 81 by welding, bonding, molding or other procedure that creates a secure and reliable seal. The coupling member 82 can be made of any biocompatible and drug compatible rigid material, including metals, plastics, and ceramics, and is typically made of plastics such as polycarbonate or Acrylonitrile butadiene styrene (ABS).

Figure 4C:
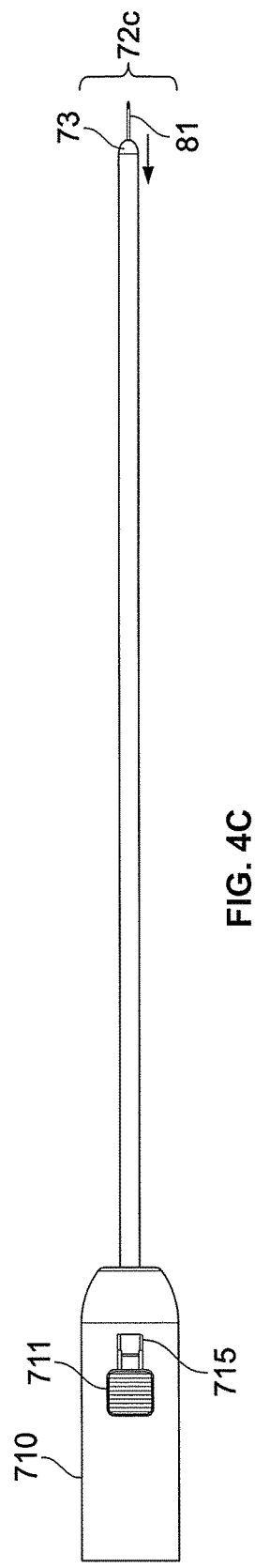

At the distal end of the device 60, the needle sheath 72 ends in a distal tip of the needle sheath 73 that contains a needle channel 733. The needle channel 733 is sufficiently sized to fit the injection needle 81 so that the injection needle can extend and retract through the needle channel 733 as the needle sheath 72 moves. In FIG. 8A, the injection needle 81 is covered by the needle sheath 72 and does not traverse through the distal portion of the needle channel 733. With reference to FIG. 4A, the device 60 in FIG. 8A is in the sheathed position 72a. In FIG. 8B, the injection needle 81 is extended out of the needle sheath 72 and does traverse through the distal portion of the needle channel 733. With reference to FIG. 4C, the device 60 in FIG. 8B is in the unsheathed position 72c.

In the unsheathed position, the needle sheath 72 is pulled back, but the injection tube 83, needle coupler 85 and injection needle 81 are fixed and do not move. For example, as shown in FIG. 8B, because the needle sheath 72 is pulled back, the size of the sheath lumen 723 between the distal end of the needle coupler 85 and the distal tip 73 of the device is shortened compared to the size of the corresponding sheath lumen shown in FIG. 8A. This demonstrates that movement of the sheath, as described with reference to FIG. 5 above using the positioner 711, only controls the movement of the needle sheath 72, while the position of the injection needle 81 and other components of the device are stationary regardless of the position of the positioner 711.

As described above, in the unsheathed position, the extent by which the injection needle 81 is extended or exposed out of the device 60 is a function of the distance between the sheath stops 715 and 716 as shown in FIG. 5. This distance is a function of the particular application of the device, the particular target tissue, the subject being treated and other considerations. For example, unsheathed needle that is exposed should not be so long that it can easily penetrate through to the other side of a target tissue. Generally, with reference to most target tissues (e.g. liver), the portion of the injection needle 81 shown in FIGS. 8B, 9B and 9D that can be unsheathed or exposed is generally less than 1 cm, such as 2 mm to 10 mm, and generally no more than 5 mm. For a child, the length can be smaller, and is generally less than 4 mm. For applications in utero, the length can be 2 mm to 3 mm.

The needle sheath 72 can be solid or can be transparent or clear. In some cases, the needle sheath 72 contains an optional visibility window 724. As described above, the presence of the visibility window 724 allows visualization of the administered agent or solution as well as the drawback fluids. For example, since some applications require injection directly into the parenchyma, and not into a vessel or bile duct, the ability to drawback and visualize fluid from the area the needle has penetrated can be used to confirm needle placement into the parenchyma, while avoiding injections into the vasculature or bile ducts. Since device 60 is long and the plunger 92 is outside of the body it is helpful to visualize the fluid path closer to the injection site and within the view of the laparoscope. To achieve this, a visibility window 724 can optionally be present in the needle sheath 72 to visualize the fluid path through a clear or transparent needle coupler 85. FIGS. 9A and 9C provide corresponding perspective views of the needle sheath shown in FIG. 8A in the sheathed position 72a. In FIG. 9A, the needle sheath 72 is solid and the injection needle inside the sheath cannot be visualized. In FIG. 9C, the needle sheath 72 contains a visibility window 724 that permits visualization of the inside components of the needle sheath 72, including the injection needle. Likewise, FIGS. 9B and 9D provide corresponding perspective views of the needle sheath shown in FIG. 8B in the unsheathed position 72c. In FIG. 9B, the needle sheath 72 is solid and the injection needle 81 inside the sheath is extended, but otherwise cannot be visualized inside the needle sheath 72. In FIG. 9D, the needle sheath 72 contains a visibility window 724 that permits visualization of the inside components of the needle sheath 72, including the portion of the injection needle 81 that is not extended out of the sheath. It is understood that the visualization window 724 in FIGS. 9B and 9D is for exemplification only, and that the visualization window can be any desired size. For example, the visualization window can extend the entire sheath. It also can extend distally and include portions of the distal tip of the needle sheath 73. Other variations also are contemplated and can be easily envisioned by a skilled artisan in view of this description.

The syringe barrel and/or the device can be disposable or reusable. For example, the syringe barrel 91 connected to the proximal side of the needle sheath controller 71 through a Luer fit adaptor 93, can be removed after injection or exhaustion of the fluid, such as a therapeutic, replaced with a new loaded syringe, or reloaded and re-connected, without the need to withdraw the device from the laparoscopic port. In some cases, the device 60 can be withdrawn from the laparoscopic port and disposed of after one use, or can be re-used.

With reference to the above Figures, exemplary of the mode of operation of the injection device 60 involves loading a standard syringe (e.g. 1 mL insulin syringe) containing a syringe barrel 91 and plunger 92 with a fluid, such as a therapeutic, prior to connecting the syringe to the needle sheath controller 71 via the Luer fit adaptor 93 of the syringe barrel 91 and the needle hub 84 connected to the injection tube 83. Once the syringe barrel 91 is loaded and connected to the needle sheath controller 71, the needle sheath 72 can be positioned in the sheathed position 72a, and the device can be inserted into a laparoscopic port to be placed near the site of injection. At the site of injection (target tissue), the needle sheath 72 can be unsheathed 72c, and the injection needle 81 can be exposed for injection. If necessary, the plunger 92 can be pulled back to draw fluids from the site of injection, to test the placement of the injection needle 81 at the injection site. The optional visibility window 724 can be used to visualize the drawback fluid from the injection site. Once the site of needle placement is determined, the plunger 92 can be depressed, to inject the fluid, such as a therapeutic, at the target tissue. After injection, the needle sheath 72 can be positioned in the sheathed position 72a, to protect the non-target organs and prevent accidental needle puncture, prior to removing the laparoscopic device from the injection site and through the laparoscopic port.

2. Integrated Injection Device

FIGS. 2, 6 and 10A-D depict the injection device 60' and components and features thereof. The injection device as shown in FIG. 2 includes needle sheath 72', needle sheath controller 71', injection needle 81, syringe barrel 91' and plunger 92'. The needle sheath 72' of the injection device is of a sufficient length to permit laparoscopic access to the target of interest, and is generally a length of 200 mm to 600 mm, such as 250 to 400 mm, and generally at least or about at least or 300 mm. The device is generally cylindrical around the longitudinal axis, generally having a smaller diameter in the needle sheath 72' region and the plunger 92' region and a larger diameter in the sheath controller 71' region. The needle sheath 72' of the device is typically inserted through the port (e.g. laparoscopic port). The diameter of the needle sheath 72' is typically from 3 mm to 12 mm in size, and typically from 5 mm to 10 mm. It is understood that portions of the device external to the laparoscopic port can have a diameter greater than 10 mm. For example, the needle sheath controller body 71' can have a diameter sufficiently large, so long as it can be easily gripped or handled by the operator. The needle sheath controller body 71' is held by the operator, typically a surgeon, to manipulate and position the device 60', control the needle sheath 72' and support the device while manipulating the plunger 92'.

The syringe barrel 91' is cylindrical in shape with a hollow center that can fit plunger 92' so that the plunger can move back and forth inside the syringe barrel. The syringe barrel is generally clear and transparent. The syringe barrel can be made out of plastic or glass or other suitable material, and in particular is made of plastic such as polypropylene, polyethylene, polycarbonate or other clear material. As described generally above, the syringe barrel 91' can contain calibrations or markings on the outer surface to indicate the volume of the agent within the barrel. As described above, the syringe barrel 91' can have a volume capacity that is from the range of 0.5 mL to 20 mL (i.e. 0.5 cc to 20 cc), and generally is 0.5 mL to 3 mL (i.e. 0.5 cc to 3 cc), such as at least or about a 1 mL (i.e. 1 cc) syringe. Typically, 200 µL to 600 µL of the fluid, such as a therapeutic, is delivered to the target locus, and the volume of syringe barrel is 1 mL.

Figure 10A:
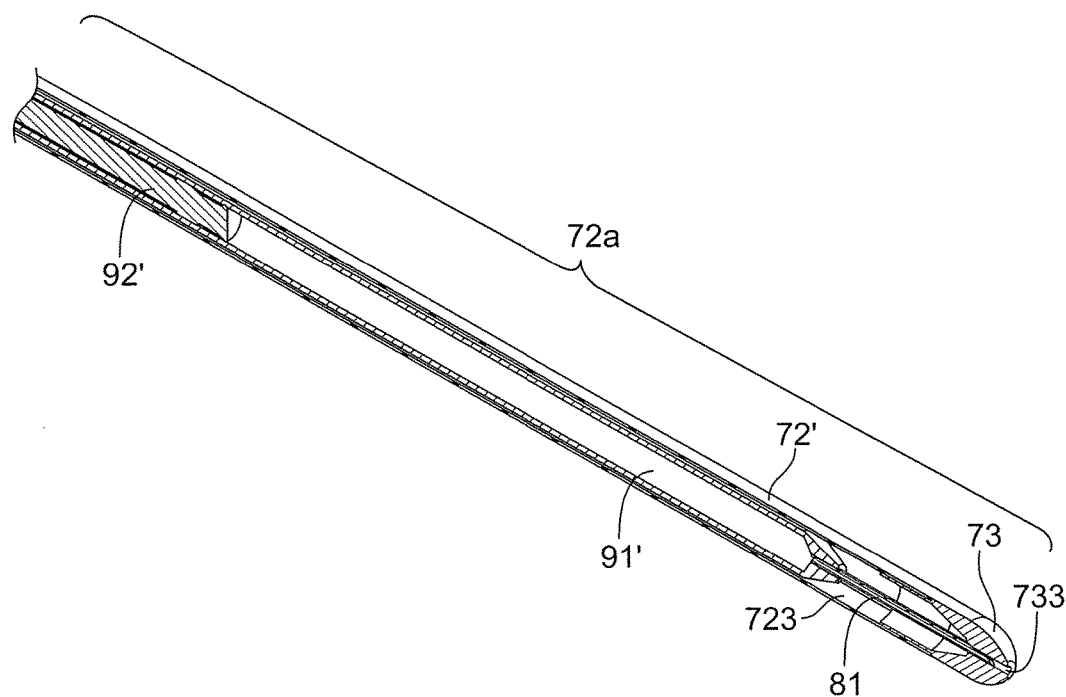
FIGS. 10A-10D illustrate enlarged views of the device shown in FIG. 2.
Figure 10B:
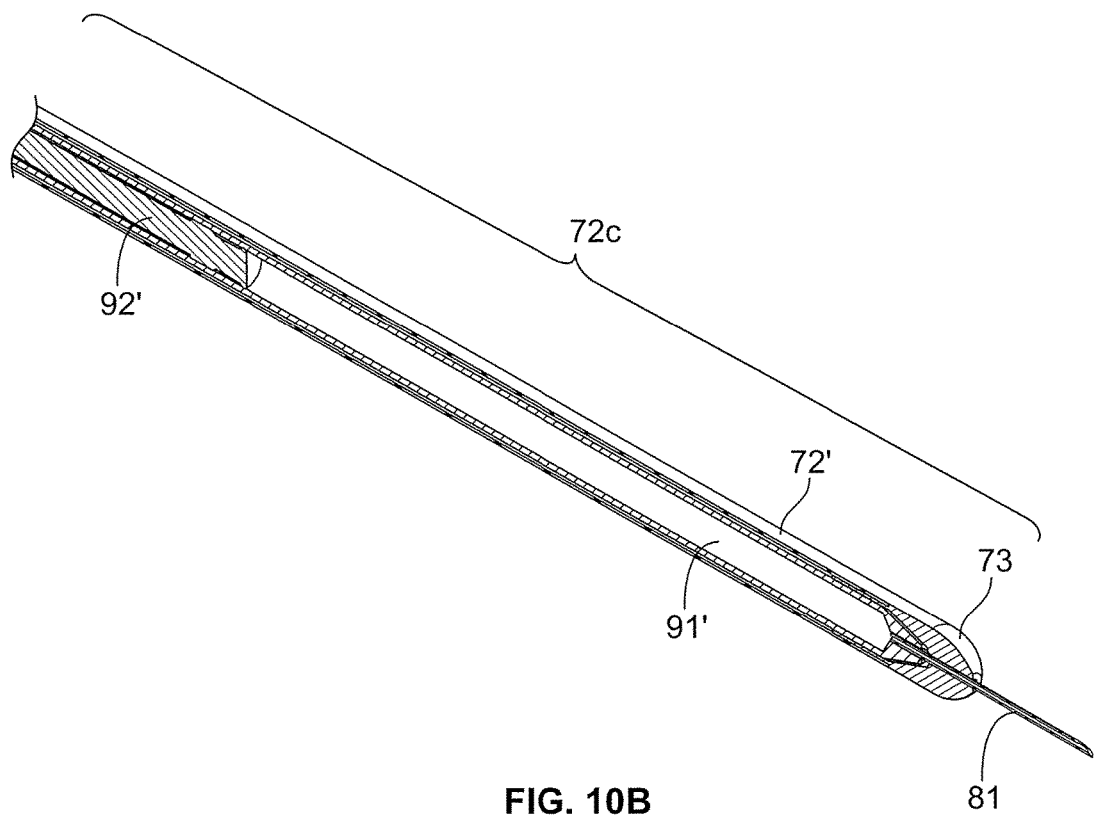

The syringe barrel 91' is positioned on the distal side of the needle sheath controller 71'. As shown in FIG. 2, the syringe barrel 91' is integrated and contained within the distal most lumen end of the needle sheath 72'. Thus, the syringe barrel is enclosed by the needle sheath 72'. As shown in FIGS. 10A and 10B, described in more detail below, the syringe barrel 91' is not directly connected to the lumen 723 of the sheath cavity, but is positioned so that it is immovable in relation to the needle sheath controller 71'. Thus, in this embodiment, the syringe barrel 91' is not removable from the needle sheath 72'.

The needle sheath 72' can be opaque or can be transparent or clear. Generally, the needle sheath 72' is opaque, but contains a visibility window 725 for visualization of the integrated syringe barrel 91'. Since device 60' contains a syringe barrel 91' that is enclosed within the needle sheath 72', and that would not otherwise be visible, the presence of the visibility window 725 permits visualization of the graduated markings on the syringe barrel to aid in drawing up agents or solutions. In addition to permitting visualization of the administered agent or solutions, the presence of the visibility window 725 allows visualization of drawback fluids. For example, since some applications require injection directly into the parenchyma, and not into a vessel or bile duct, the ability to drawback and visualize fluid from the area the needle has penetrated can be used to confirm needle placement into the parenchyma, while avoiding injections into the vasculature or bile ducts. The visibility window 725 can be made of glass or clear plastic such as polycarbonate. The visibility window 725 is integrated directly into the body of the needle sheath 72'. The visibility window can surround the entire circumference of the needle sheath 72' or can partially surround the circumference of needle sheath 72'. The visibility window 725 can be any desired length, and located anywhere along the needle sheath 72' so long as a portion of the syringe barrel 91' is exposed under the visibility window 725. Generally, the visibility window 725 exposes the distal portion of the syringe barrel 91', but can expose the entire syringe barrel 91. The visibility window 725 can be 10 cm to 300 mm, and generally is 20 mm to 100 mm in length.

The plunger 92' is located on the proximal end of the device 60' and passes through the needle sheath controller 71' and the needle sheath 72' where it can engage with and pass into the syringe barrel 91'. The plunger 92' is movable through the needle sheath controller 71', needle sheath 72' and syringe barrel 91' so that it can be pulled and pushed along inside the syringe barrel 91'. The plunger 92' can be drawn back to load the syringe barrel 91' with the fluid, such as a therapeutic, or depressed to inject the fluid, such as a therapeutic, in the target tissue. The plunger 92' also can be pulled back at the site of injection to test needle placement. The plunger is cylindrical to move through the syringe barrel 91', and is made of material that permits ease of movement through the needle sheath controller 71', needle sheath 72' and syringe barrel 91'. Typically, the plunger 92' is made of plastic, for example polypropylene or polyethylene. The plunger contains a head 95 at the proximal end of the device that can be conveniently grasped by the operator to manipulate the plunger. The plunger head 95 also is generally made of plastic. The distal tip of the plunger 92' is generally made of silicone or other natural or synthetic rubber to provide a tight seal within the syringe barrel 91' when traveling within the syringe barrel 91'.

The plunger 92' is long enough in length to permit its association with the inside of the syringe barrel 91' in order to dispel the fluid, such as a therapeutic through the distal end of the syringe and into the needle 81 connected thereto. Since the plunger essentially extends the length of the device, the plunger is generally at least as long as the sheath, and generally longer since it extends outside of the laparoscopic port. For example, the plunger 92' can be 200 mm to 800 mm, such as 300 to 600 mm, and generally at least or about at least or 300 to 400 mm. Pulling back on the plunger 92' draws in the fluid, such as a therapeutic, or air, and pushing the plunger 92' forces the fluid, such as a therapeutic, or air out of the syringe barrel.

The device 60' contains an injection needle 81 that is located inside the needle sheath 72' that can be sheathed and unsheathed at the distal tip of the needle 81. With reference to FIG. 10A, described in more detail below, the distal tip of the needle sheath 73 contains a needle channel 733 that guides the needle outside of the needle sheath 72' when it is unsheathed as shown in FIG. 2. As shown in FIG. 2, the injection needle contains a beveled tip sufficient to penetrate or pierce a tissue or an organ.

As discussed further below, because the injection needle 81 is directly attached to the syringe barrel 91' at the distal end of the device, the injection needle is relatively short. This avoids problems in pressure drop that can occur with longer needles. This also means that the dead volume in the device 60', which is the volume of fluid that is loaded into the syringe barrel 91', but cannot be expelled from the device and injected into the tissue, is generally small. Since therapeutics are often costly or limited, an injection device that minimizes amount of dead volume is advantageous. Factors that influence the amount of dead volume include the length of the needle, the diameter of the needle, and the diameter of the syringe barrel. In case of a long needle, the amount of air in the needle often is not tolerable in the patient and the target tissue and/or organ. Hence, the air needs to be removed from the needle and the needle is sometimes "primed." After the injection, the amount of fluid remaining in the fluid path between the tip of the plunger and the tip of the injection needle 81 cannot be expelled completely, and thus results in dead volume. In case of a long needle, the amount of dead volume is thus larger. In device 60', the syringe barrel 91' is located close to the tip of the needle sheath 72', and the dead volume occurs only in the tip of the syringe barrel 91' and the injection needle 81.

FIG. 6 depicts an enlarged cross section view of the needle sheath controller 71' and the plunger 92' extended through the needle sheath controller 71'. The needle sheath controller 71' is positioned on the proximal side of the needle sheath 72'. The needle sheath controller 71' contains the components that control movement of the needle sheath 72', connect the proximal and distal end of the device, and is the conduit by which the plunger 92' travels between the proximal and distal ends of the device. The needle sheath controller 71' is configured to be held and manipulated by an operator, such as a surgeon. As discussed above, the needle sheath controller 71' can be any shape and size that is convenient to permit the operator to hold and manipulate the device, and typically is cylindrical in shape. The diameter of the needle sheath controller 71' is such that it can be held in the palm of an average adult, and is generally 20 mm to 100 mm in diameter with a length of 50 mm to 225 mm. The needle sheath controller optionally can contain an outside grip for handling.

As shown in FIG. 2 and FIG. 6, the needle sheath controller 71' includes a controller housing 710 that encloses components internal to the needle sheath controller 71', and the proximal end of the needle sheath 72'. As discussed above, the needle sheath controller housing 710 can be made of any suitably resilient and rigid material, such as any polymeric material, including plastics, or rubber, metals, ceramics, composites, or other suitable material known to one of skill in the art. The controller housing 710 is typically made of polypropylene, polystyrene, polyethylene, polyvinyl chloride, polyurethane, silicone, rubber or acrylic. As discussed above, the housing 710 can be made by any manufacturing known to a skilled artisan, and can be made as one singular piece or can be made of two or more pieces that are attached together, such as with adhesive, locking joints or fasteners.

As shown in FIG. 2 and FIG. 6, the needle sheath controller 71' contains an externally accessible positioner 711. As described above, the positioner 711 is configured in the needle sheath controller 71' so that it is movable both forward and rearward relative to the needle sheath controller 71'. As described above, the positioner 711 is engaged with the needle sheath 72' through a connection member 713, and can be used to slide the needle sheath 72'. This connection permits movement of the positioner 711 between the forward or rearward positions to control movement of the needle sheath between two fixed or locked positions, the sheathed and unsheathed positions. The sheathed position protects or hides the injection needle, while the unsheathed position exposes the needle.

With reference to FIG. 6, the connection member 713 is connected to the proximal end of the needle sheath 72', and the lower part of the positioner 711. The connection of the connection member 713 with the proximal end of the needle sheath is such that the needle sheath 72' is longitudinally movable relative to the controller housing 710 and the injection needle 81. For example, the distal end of the outside of the connection member 713 is engaged with the proximal inside cavity of the needle sheath 72' around its circumference. The connections of the control member with the positioner 711 and needle sheath 72' can be by welding, adhesive, locking joints, fasteners or other suitable means.

As described above generally, the connection member 713 moves inside a hollow cavity or lumen 717 contained inside the housing 710 of the needle sheath controller 71' that is closed at both ends relative to the housing 710. The controller lumen 717 accommodates the connection member 713 such that the connection member 713 can easily glide or move forward or rearward in a restricted manner. For example, the connection member 713 can be cylindrical and fit inside a cylindrical hollow lumen cavity 717. As shown in FIG. 6, and discussed further below, the connection member 713 contains an internal hollow cavity sized to fit the plunger 92' that passes through.

Movement of the connection member 713 is controlled by the positioner 711. As shown in FIGS. 2 and 6, the positioner 711 contains a projected top portion or head that juts out of the needle sheath controller 71' where it can be moved forward or rearward by the operator. As shown in FIG. 6, internal to the needle sheath controller 71', the body of the positioner 711 is notched on its sides or is otherwise configured to engage with sheath stops 715 or 716. Sheath stops 715 and 716 are grooves in the needle sheath controller housing 710 that fit the notched body of the positioner and trap the positioner 711 so that it cannot be moved.

As exemplified in FIG. 5 with the exemplary device 60, device 60' also contains an optional lock and release element 712 configured in the positioner 711 to facilitate lock and release of the positioner with the grooves of the sheath stop 715 or 716. For example, the lock and release element 712 can be a spring or other resilient means. The mechanism controlling lock and release of the positioner 711 with the grooves of the sheath stop 715 or 716 by the lock and release element 712 is as described above, whereby downward, vertical or lateral forces release or lock the positioner 711 from the sheath stops 715 or 716. Pushing downward on the positioner 711 permits the positioner to slide and to fit it into either of sheath stops 715 or 716.

Movement of the positioner 711 between the sheath stops 715 and 716 moves the connection member 713, and thereby also moves the needle sheath 72' so that it can transition from the sheathed and unsheathed positions by control of the positioner by the operator. When the positioner is in the rearward position 711c as exemplified in FIG. 6, distal sheath stop 715 is free and the positioner 711 is fit into the proximal sheath stop 716, thereby unsheathing the injection needle so that it is exposed. While not shown in FIG. 6, the positioner 711 also can be in the forward position 711a as exemplified in FIG. 5, where the proximal sheath stop 716 is free and the positioner 711 is fit into the distal sheath stop 715, thereby sheathing the injection needle so that it is protected. As a further position, the positioner 711 also can be in an intermediate position 711b as exemplified in FIG. 7, where both the distal sheath stop 715 and the proximal sheath stop 716 are free and not engaged with the positioner 711.

As shown in FIG. 6, the plunger 92' passes through the inside lumen 717 of the needle sheath controller 71' and passes through a central cavity of the connection member 713, but is not directly attached to the needle sheath controller 71' or connection member 713. Hence, the connection member 713 can move independently around the plunger 92', and the plunger 92' can move independently through the connection member 713. As discussed above, because the needle sheath 72' is directly connected to the connection member 713 contained in the controller lumen 717, the plunger 92' enters the inside cavity of the needle sheath 72' inside the needle sheath controller 71'. The plunger 92' exists the distal end of the needle sheath controller 71' where it is contained within the lumen 723 of the needle sheath 72'.

With reference to FIGS. 10A and 10B, the plunger 92' runs distally and longitudinally through the needle sheath 72' where it engages with the proximal end of the syringe barrel 91'. The injection needle 81 is directly connected to the inside of the syringe barrel 91' at the distal end of the syringe barrel 91'. The injection needle 81 contains a beveled tip sufficient to penetrate or pierce a tissue or an organ. The injection needle 81 is typically made of metal or alloy, such as surgical stainless steel or other medica grade metal. The size and diameter of the injection needle 81 is selected based on parameters generally describe above. As described above, typically a small diameter needle 81 is employed to reduce the force required to insert the needle into the target tissue or organ, and to reduce trauma to the target tissue or organ. For example, the injection needle 81 is between 25 and 34 gauge, such as a 25 gauge, 26 gauge, 27 gauge, 28 gauge, 29 gauge, 30 gauge or 31 gauge needle, and typically is 27 gauge.

At the distal end of the device 60', the needle sheath 72' ends in a distal tip 73 that contains a needle channel 733. The needle channel 733 is sufficiently sized to fit the injection needle 81 so the injection needle can extend and retract through the needle channel 733 as the needle sheath 72' moves. In FIG. 10A, the injection needle 81 is covered by the needle sheath 72' and does not traverse through needle channel 733. With reference to FIG. 4A, the device 60' in FIG. 10A is in the sheathed position 72a. In FIG. 10B, the injection needle 81 is extended out of the needle sheath 72' and does traverse through needle channel 733. With reference to FIG. 4C, the device 60' in FIG. 10B is in the unsheathed position 72c.

As shown in FIGS. 10A and 10B, because the syringe barrel 91' is not connected to the needle sheath 72', the needle sheath 72' moves independently around the syringe 91'. In the unsheathed position, the needle sheath 72' is pulled back, but the syringe barrel 91' and injection needle 81 are fixed and do not move. For example, as shown in FIG. 10B, because the needle sheath 72' is pulled back, the size of the sheath lumen 723 is shortened compared to FIG. 10A when the needle sheath 72' is not pulled back. In the unsheathed position shown in FIG. 10B, the distal end of the syringe barrel 91' touches the distal tip of the sheath 73. A notch can be configured in the distal tip 73 in order to accommodate the syringe barrel 91' as it is positioned in the unsheathed position 72c. This demonstrates that movement of the sheath, as described with reference to FIG. 6 above using the positioner 711, only controls the movement of the needle sheath 72', while the position of the syringe barrel 91' and injection needle 81 of the device are stationary regardless of the position of the positioner 711.

As described above, in the unsheathed position, the extent by which the injection needle 81 is extended or exposed out of the device 60' is a function of the distance between the sheath stops 715 and 716 as shown in FIG. 6. This distance is a function of the particular application of the device, the particular target tissue, the subject being treated and other considerations. For example, unsheathed needle that is exposed should not be so long that it can easily penetrate through to the other side of a target tissue. Generally, with reference to most target tissues (e.g. liver), the portion of the injection needle 81 shown in FIG. 10B that can be unsheathed or exposed is generally less than 1 cm, such as 2 mm to 10 mm, and generally no more than 5 mm. For a child, the length can be smaller, and is generally less than 4 mm. For applications in utero, the length can be 2 mm to 3 mm. Generally, the total length of the injection needle 81 in device 60' is slightly longer than the unsheathed needle tip that extends out of the device. As shown in FIG. 10B, the extent of the extra length is sufficient to account for the distance of the distal sheath tip 73 and the extent to which the proximal end of the needle is connected to syringe barrel 91'. For example, the total length of the injection needle 81 can range from 5 mm to 40 mm, such as 10 mm to 40 mm, such as a 12.7 mm, 25.4 mm or 38.1 mm needle.

Figure 10C:
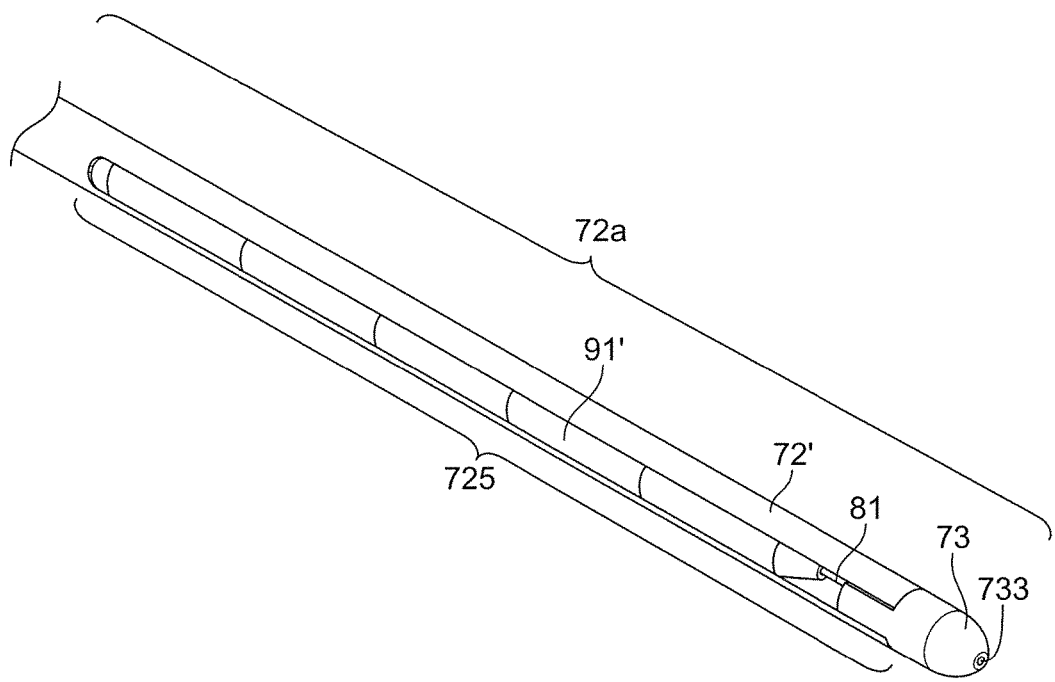
Figure 10D:
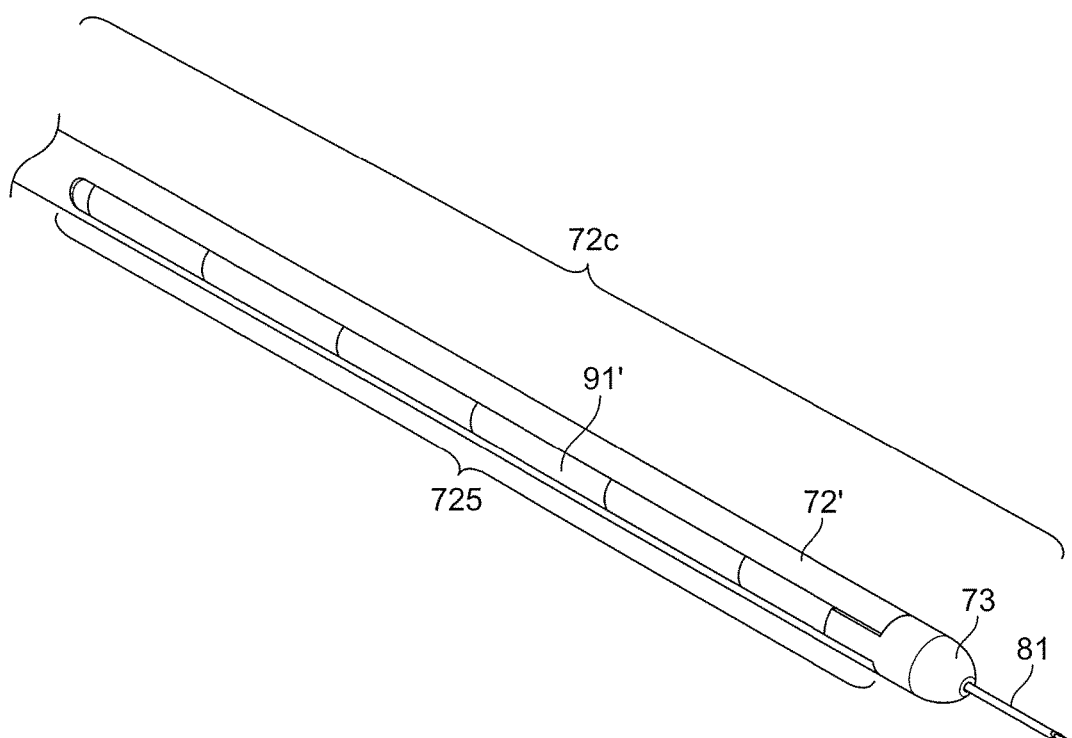

FIG. 10C provides a corresponding perspective view of the needle sheath shown in FIG. 10A in the sheathed position 72a. FIG. 10D provides a corresponding perspective view of the needle sheath shown in FIG. 10B in the unsheathed position 72c. In FIGS. 10A and D, the needle sheath 72' is opaque, but contains a visibility window 725 in order to view the syringe barrel 91' and injection needle 81 whether sheathed or unsheathed.

The device 60' can be disposable or reusable. For example, the device 60' can be withdrawn from the laparoscopic port and disposed of, or reloaded and reused. The device 60' also can be a sterile device. For example, the device 60' can be loaded through the injection needle 81 in a sterile environment, such as a sterile operating room. The device 60' can be pre-loaded with the fluid, such as a therapeutic, and provided as a sterile pre-loaded syringe. Furthermore, distribution of sterile disposable pre-loaded devices is easily achieved using this device 60' due to the complete integration of the syringe barrel into the needle shaft, thereby minimizing contamination that can occur when the syringe barrel and device must be packaged or stored separately. Alternatively, the injection needle 81 can be inserted into a container with the fluid, such as a therapeutic, composition, and the plunger 92' can be pulled back to load the fluid, such as a therapeutic, in the syringe barrel 91'.

With reference to the above Figures and description, exemplary of the mode of operation of the injection device 60' involves first loading the device 60' with a fluid, such as a therapeutic. With the needle sheath 72' in the unsheathed position 72c, the injection needle 81 can be inserted into a vial or a container of fluid, such as a therapeutic, and the integrated syringe plunger 92' can be pulled back to load the syringe with the fluid, such as a therapeutic. Optionally, a vial adaptor can be used when loading the syringe with the therapeutic compound, such that the long device can be stabilized over a vial or container of fluid, such as a therapeutic, loading the syringe barrel 92'. Once the syringe is loaded, the needle sheath 72' can be positioned in the sheathed position 72*a*, and the device can be inserted into a laparoscopic port to place the device near the site of injection. At the site of injection (target tissue), the needle sheath 72' can be unsheathed 72*c*, and the injection needle 81 can be exposed for injection. If necessary, the integrated syringe plunger 92' can be pulled back to draw fluids from the site of injection, to test the placement of the injection needle 81 at the injection site. The syringe visibility window 725 can be used to visualize the drawback and the movement of the plunger 92'. Once the site of needle placement is determined, the plunger 92' can be depressed, to inject the fluid, such as a therapeutic, at the target tissue. After injection, the needle sheath 72' can be positioned in the sheathed position 72*a*, to protect the non-target organs and prevent accidental needle puncture, prior to removing the laparoscopic device from the injection site and through the laparoscopic port.

3. Dockable Injection Device

FIGS. 3, 7 and 11A-D depict the injection device 60" and components and features thereof. The injection device as shown in FIG. 3 includes needle sheath 72", needle sheath controller 71', plunger 92" and a dockable syringe 910 containing injection needle 81, syringe barrel 91", and associated auxiliary plunger 920. The needle sheath 72" of the injection device is of a sufficient length to permit laparoscopic access to the target of interest, and is generally a length of 200 mm to 600 mm, such as 250 to 400 mm, and generally at least or about at least or 300 mm. The device is generally cylindrical around the longitudinal axis, generally having a smaller diameter in the needle sheath region 72" and the plunger region 92" and a larger diameter in the needle controller region 71'. The needle sheath 72" of the device is typically inserted through the port (e.g. laparoscopic port). The diameter of the needle sheath 72" is typically between 3 mm to 12 mm in size, and typically from 5 mm to 10 mm. It is understood that portions of the device external to the laparoscopic port can have a diameter greater than 10 mm. For example, the needle sheath controller body 71' can have a diameter sufficiently large, so long as it can be easily gripped or handled by the operator. The needle sheath controller body 71' is held by the operator, typically a surgeon, to manipulate and position the device 60", control the needle sheath 72" and support the device while manipulating the plunger 92".

Injection device 60" is adapted so that a dockable syringe 910 containing injection needle 81, syringe barrel 91" and associated auxiliary plunger 920 can be temporarily docked therewith. As shown in FIG. 3, the syringe barrel 91" is cylindrical in shape with a hollow center that can fit auxiliary plunger 920 so that the plunger can move back and forth inside the syringe barrel. The auxiliary plunger 920 is located on the proximal side of the syringe barrel 91" and is movable so that it can be pulled and pushed along inside of the syringe barrel 91". The auxiliary plunger 920 can be drawn back to load the syringe barrel 91" with the fluid, such as a therapeutic, or depressed to dispel or inject the fluid in the target tissue. The auxiliary plunger 920 can also be pulled back at the site of injection to test needle placement. As discussed below, movement of the auxiliary plunger 920 when docked in the device is controlled by the plunger 92". The auxiliary plunger 920 is cylindrical to move through the syringe barrel 91", and is made of material that permits ease of movement through the syringe barrel, such as a plastic, for example, polypropylene or polyethylene.

The auxiliary plunger 920 contains a plunger head 95 at the proximal end of the plunger that can be conveniently grasped by the operator to manipulate the plunger, or otherwise configured to control movement of auxiliary plunger 920. For example, the auxiliary plunger 920 can be independently moved and controlled, for example, when the dockable syringe 910 is in the undocked position (discussed further below). In other instances, when the dockable syringe 910 is docked in device 60", movement of the auxiliary plunger 920 is controlled by plunger 92" at the proximal end of device 60" through a plunger adaptor 951 (discussed further below). The plunger head 95 also is generally made of plastic. The distal tip of the auxiliary plunger 920 is generally made of silicone or other natural or synthetic rubber to provide a tight seal within the syringe barrel 91" when traveling within the syringe barrel 91".

The auxiliary plunger 920 is long enough in length to permit its association with the inside of syringe barrel 91" in order to dispel the fluid, such as a therapeutic, through the distal end of the syringe barrel 91" and into injection needle 81 connected thereto. For example, the auxiliary plunger 920 can have a length between 50 mm and 100 mm, typically 70 mm to 90 mm. Pulling back on the auxiliary plunger 920 draws in the fluid or air, and pushing the auxiliary plunger 920 forces the fluid or air out of the syringe barrel.

The syringe barrel 91" is generally clear and transparent. The syringe barrel 91" can be made out of plastic or glass or other suitable material, and in particular is made out of plastic such as polypropylene, polyethylene, polycarbonate or other clear material. As described above, the syringe barrel 91" can contain calibrations or marking on the outer surface to indicate the volume of the agent within the barrel. As described above, the syringe barrel 91" can have a volume capacity that is from the range of 0.5 mL to 20 mL (i.e. 0.5 cc to 20 cc), and generally is 0.5 mL to 3 mL (i.e. 0.5 cc to 3 cc), such as at least or about a 1 mL (i.e. 1 cc) syringe. Typically, 200 µL to 600 µL of the fluid, such as a therapeutic, is delivered to the target locus, and the volume of syringe barrel is 1 mL.

The dockable syringe 910 of device 60" contains an injection needle 81 that is located on the distal end of the syringe barrel 91", and hence the distal end of the device 60" when the dockable syringe 910 is docked into device 60" (discussed further below). The injection needle 81 can be connected directly or indirectly to syringe barrel 91". For example, the injection needle 81 can be directly affixed, such as by an adhesive, bonding or molding, to the inside of syringe barrel 91" at the distal end of syringe barrel 91". In other examples, the distal end of syringe barrel 91" can contain a Luer fit or other adaptor that is compatible with a hub on the proximal end of injection needle 81.

As shown FIG. 3, the injection needle contains a beveled tip sufficient to penetrate or pierce a tissue or an organ. The injection needle 81 is typically made of metal or alloy, such as surgical stainless steel or other medical grade metal. The size and diameter of the injection needle 81 is selected based on parameters generally describe above. As described above, typically a small diameter needle 81 is employed to reduce the force required to insert the needle into the target tissue or organ, and to reduce trauma to the target tissue or organ. For example, the injection needle 81 is between 25 and 34 gauge, such as a 25 gauge, 26 gauge, 27 gauge, 28 gauge, 29 gauge, 30 gauge or 31 gauge needle, and typically is 27 gauge.

Because the injection needle 81 is directly attached to the syringe barrel 91", the injection needle is relatively short. This avoids problems in pressure drop that can occur with longer needles. Similar to device 60' discussed above, this also means that there is generally a small dead volume created by device 60". For example, the total length of the injection needle 81 can range from 5 mm to 40 mm, such as 10 mm to 40 mm, such as a 12.7 mm, 25.4 mm or 38.1 mm needle. Generally, the use of shorter needle is desired in order to avoid problems related to dead volume and pressure drops.

Figure 11A:
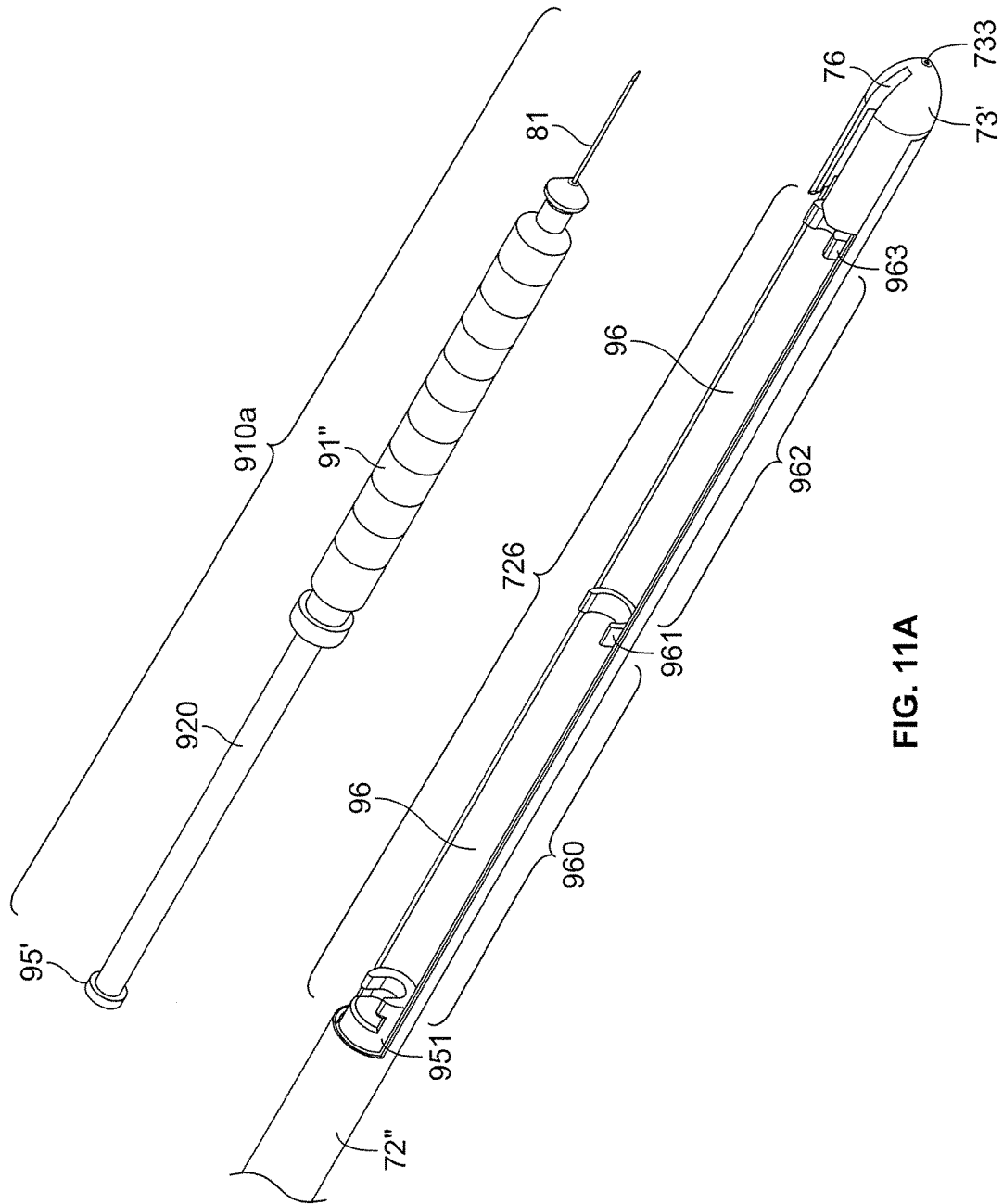

The needle sheath 72" can be opaque or can be transparent or clear. The needle sheath 72" is generally solid at the proximal portion of the needle sheath 720, but contains an open cavity 726 at its distal portion. The dockable syringe 910 containing auxiliary plunger 920, syringe barrel 91" and injection needle 81 is configured so that it can be docked and undocked in the open cavity of the sheath, and in a manner in which the needle sheath 72" is movable around the dockable syringe 910. As shown in FIG. 3 and FIG. 11A, the open cavity 726 is a cut out in the top half of the needle sheath 72". The inner side of the open cavity 726 of the sheath can be lined with a syringe adaptor lining 96 in a manner so that the sheath moves independently from the syringe adaptor lining 96. The syringe adaptor lining 96 also has an open cavity of substantially similar size.

Figure 11B:
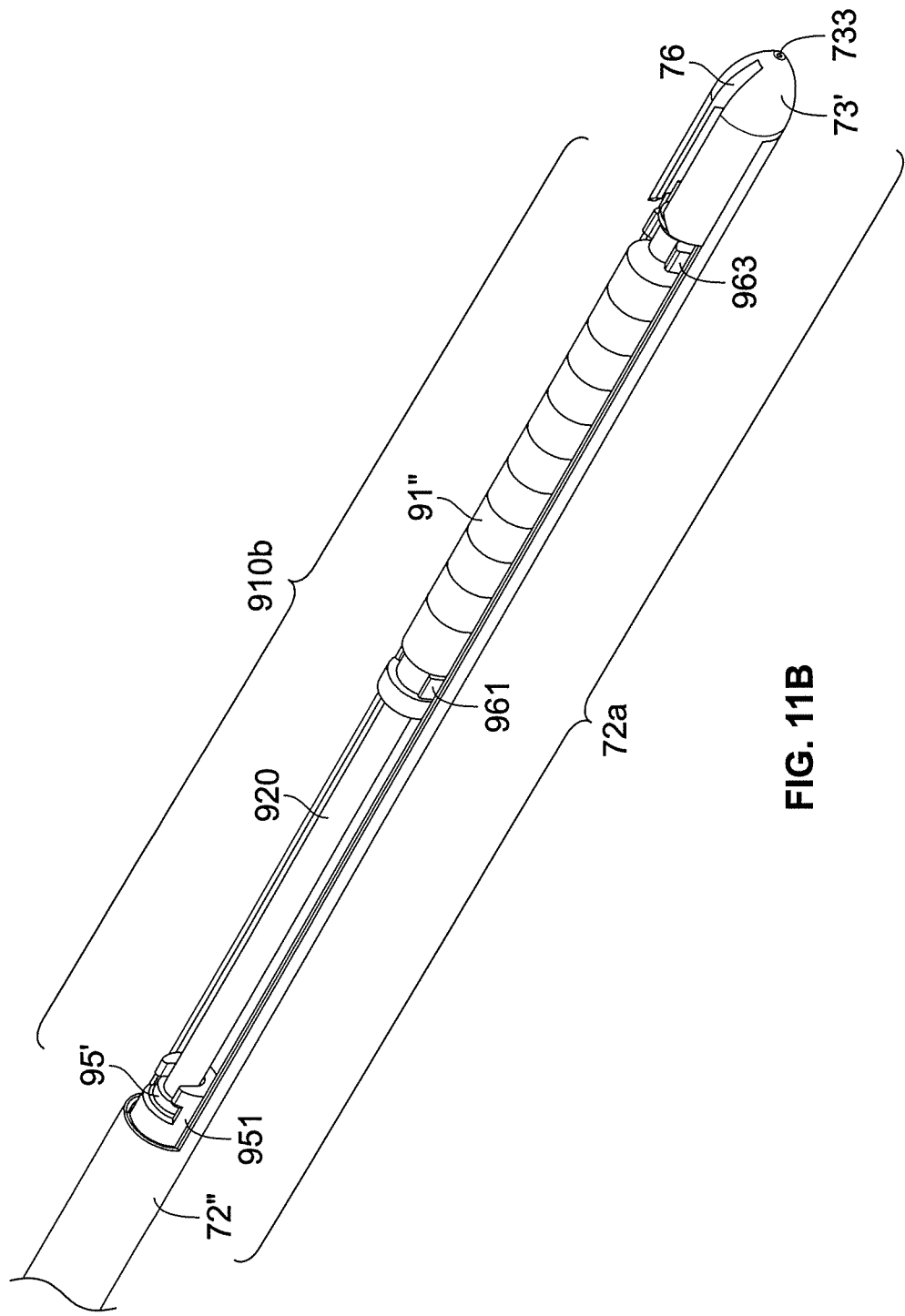

For example, as shown in FIGS. 11A and 11B, a syringe adaptor lining 96 can run through the sheath, such that the sheath moves independently around the syringe adaptor lining 96. The syringe adaptor lining 96 can be connected or fixed at its proximal end to the needle sheath controller 71' and have an open cavity at its distal end to form a nest for the dockable syringe. For example, the syringe adaptor lining 96 can be a hypodermic tubing that has a distal section removed to form a nest for the dockable syringe. The tubing can have a diameter smaller than the inside portion of the needle sheath 72" so that the tubing can run into and through the sheath where it can be connected to the needle sheath controller 71' in a fixed position.

The open cavity of the syringe adaptor lining 96 can contain a plunger rest cavity 960, a barrel rest cavity 962, and two barrel docks 961 and 963. The barrel rest cavity 962 is flanked by two barrel docks 961 and 963, which are clasps or fitting that are adapted to seat or secure the syringe barrel 91" at its proximal and distal end, respectively. The size of the barrel rest cavity 962 and the distance between the two barrel docks 961 and 963 permit engagement with the syringe barrel 91". If the syringe barrel 91" contains grooves to fit into the barrel docks 961 and 963, the length between the two barrel docks 961 and 963 is the same as the length between the corresponding grooves in the syringe barrel 91". The portion of the syringe barrel 91" that can dock with barrel docks 961 and 963 can be restricted by configuring syringe barrel 91" with narrow grooves at its proximal and distal ends that fit dock 961 and 963, respectively. This ensures that the syringe barrel 91", when fitted in the open cavity 726, is properly lined up for sheathing and unsheathing injection needle 81. The barrel docks 961 and 963 can be similarly sized, or can be different sizes depending on the particular size and configuration of syringe barrel 91". The barrel docks 961 or 963 can be rigid or flexible, and can be made out of metal or polymeric materials such as plastics. The barrel docks 961 and 963 can be features extruding from the syringe adaptor lining 96, or can be separate parts that are attached to the exposed part of the syringe adaptor lining 96. The barrel rest cavity 962 and the docks 961 and 963 are not directly connected to the needle sheath so that the needle sheath 72" moves around and independently from the syringe adaptor lining 96, including the barrel rest cavity and docks.

A plunger adaptor 951 that is part of the distal end of plunger 92" is located at the proximal end of the cavity 726. The plunger adaptor 951 rests inside open cavity of the syringe adaptor lining 96 when the plunger 92" is pulled back in an extended position. As discussed below, the plunger 92" is movable within the lumen of the syringe adaptor lining 96 in order to control movement of auxiliary plunger 920. The distance between barrel dock 961 and plunger adaptor 951 when the plunger 92" is in its extended position (i.e. pulled out to maximum length outside of syringe barrel) creates a plunger rest cavity 960 within the syringe adaptor lining 96 sufficiently sized to fit the auxiliary plunger 920 in its extended position.

Hence, the length of the open cavity 726 of the needle sheath 72" and the open cavity of the syringe adaptor lining 96 is sufficient to fit dockable syringe 910. In some instances, the cavity can span the entire length of the needle sheath 72", except for the distal tip of the needle sheath 73' discussed below. Typically, the open cavity 726 is 50 mm to 250 mm in length. Accordingly, the open cavity of the syringe adaptor lining 96, which has a substantially similar length to the open cavity 726 of the needle sheath, is 50 mm to 250 mm in length. The length of the open cavities also depends on the diameter of the needle sheath 72", the volume, length and diameter of the dockable syringe 910. If a larger volume of syringe barrel 91" is needed for a specific injection, the length of the syringe barrel 91" and the open cavities can be made larger. However, the stroke length of the auxiliary plunger 920 is limited to less than half of the entire length of the needle sheath 72", as both the fully extended auxiliary plunger 920 and the syringe barrel 91" must fit in the length of the needle sheath 72" and the open cavities. The stroke length of the plunger 92" is also limited to the maximum stroke length of the auxiliary plunger 920. Hence, if a larger volume of syringe barrel 91" is needed, the diameter of the needle sheath 72" can be larger. The optimal length and diameter of the syringe barrel 91" in relation to the stroke length and the length of the needle sheath 72", including the length of the proximal portion of the needle sheath 720, can be empirically determined based on the diameter of the laparoscopic ports, type of surgery, and the volume of syringe barrel required.

The open cavities terminate at the distal tip of the needle sheath 73'. The distal tip of the needle sheath 73' is solid, except that it contains an open needle groove 76 on its top side. The needle groove 76 is a narrow opening sufficient for injection needle 81 to drop into the distal tip of needle sheath 73' where it can line up with needle channel 733 to guide the injection needle 81 outside when unsheathed. The length and diameter of the groove 76 is sufficient to fit injection needle 81. For example, the needle groove 76 is 5 mm to 40 mm long, such as 10 mm to 40 mm. The width of the needle groove is 0.2 to 2 mm, such as 0.3 to 1 mm.

FIGS. 11A and 11B depict the dockable and undocked configurations of dockable syringe 910 with the syringe adaptor lining 96 and the needle sheath 72". For example, FIG. 11A shows the dockable syringe 910 in the undocked position 910a. As shown in FIG. 11A, a syringe adaptor lining 96 is inside the needle sheath 72". An open cavity of the syringe adaptor lining 96 configured into the open cavity 726 of the needle sheath 72" is configured to fit the dockable syringe 910 as described above. FIG. 11B shows the dockable syringe 910 in the docked position 910b. In the docked position 910b, the dockable syringe 910 is positioned on the distal side of the needle sheath controller 71'. When in the docked position 910b, the injection needle 81 is located inside the needle sheath 72" and can be sheathed and unsheathed at the distal tip of the needle 81 as discussed below.

The ability to dock into syringe dock accessible by the open cavity 726 of the needle sheath 72" and the open cavity of the syringe adaptor lining 96 permits visualization of the syringe barrel in device 60" so that the administered agent or drawback fluids can be visualized. For example, as discussed above, since some applications require injection directly into the parenchyma, and not into a vessel or bile duct, the ability to drawback and visualize fluid from the area the needle has penetrated can be used to confirm needle placement into the parenchyma, while avoiding injections into the vasculature or bile ducts.

In addition, the ability to remove or dock the syringe 910 in injection device 60" also provides advantages, including the ease of loading the syringe barrel, exchange of loaded syringe, and sterility of syringe. For example, a sterile syringe barrel 91" can conveniently be used when drawing up or loading the syringe with a fluid, such as a therapeutic, compositions or other solutions into the syringe barrel. If desired, a separately sterile needle 81 can be fitted to the syringe barrel 91", such as by a Luer fit adaptor, to permit loading of the syringe barrel 91" with a fluid, such as a therapeutic. Syringe barrel 91" also can be separately loaded prior to use of device 60", or a pre-loaded syringe barrel 91" can used. Also, a variety of syringe types and sizes can be used so long as they are dockable with the device 60". In some cases, several different types of syringes can be used for one patient, if necessary. In cases where the syringe must be re-loaded or additional fluid, such as a therapeutic, is needed, new or re-loaded syringes can be docked.

As shown in FIG. 3, plunger 92" is located on the proximal end of the device 60" where it can be controlled and operated by the operator outside of the laparoscopic port. Plunger 92" passes through the needle sheath controller 71' and the proximal portion of the needle sheath 72". The plunger 92" is generally cylindrical and movable within needle sheath controller 71' and needle sheath 72". The plunger 92" is made of material that permits ease of movement through the needle sheath controller 71' and needle sheath 72". Typically, the plunger 92" is made of plastic, for example polypropylene or polyethylene. The distal end of the plunger 92" contains a plunger adaptor 951 that is exposed through open cavity 726 in the needle sheath 72" where it associates with auxiliary plunger 920. The plunger 92" is long enough in length to permits its association with auxiliary plunger 920 in needle sheath 72" when auxiliary plunger 920 is docked in cavity 726. For example, the length of plunger 92" can range from 50 mm to 500 mm, such as 100 mm to 400 mm or 100 mm to 200 mm. Plunger 92" is generally longer than auxiliary plunger 920.

The plunger adaptor 951 contains a groove or notch to connect with auxiliary plunger 920 through plunger head 95' of auxiliary plunger 920. The plunger adaptor 951 is of a sufficient size and shape so that plunger head 95' of auxiliary plunger 920 can be seated or secured in the plunger rest cavity 960. As shown in FIG. 11B, when plunger head 95' of auxiliary plunger 920 is fitted or secured in plunger adaptor 951, the auxiliary plunger 920 and the plunger 92" are connected, such that movement of the plunger 92" controls movement of auxiliary plunger 920. The plunger 92" also contains a plunger head 95 at the proximal end of the device that can be conveniently grasped by the operator to manipulate plunger 92", and thus also auxiliary plunger 920. For example, pushing the plunger 92" also pushes the auxiliary plunger 920 and forces the fluid or air out of the syringe barrel 91".

FIG. 7 depicts an enlarged cross section view of the needle sheath controller 71' and the plunger 92" extended through the needle sheath controller 71'. The needle sheath controller 71' is positioned on the proximal side of the needle sheath 72". The needle sheath controller 71' contains the components that control movement of the needle sheath 72", connect the proximal and distal end of the device, and is the conduit by which the plunger 92" travels between the proximal and distal ends of the device. The needle sheath controller 71' is configured to be held and manipulated by an operator, such as a surgeon. As discussed above, the needle sheath controller 71' can be any shape and size that is convenient to permit the operator to hold and manipulate the device, and typically is cylindrical in shape. The diameter of the needle sheath controller 71' is such that it can be held in the palm of an average adult, and is generally 20 mm to 100 mm in diameter with a length of 50 mm to 225 mm. The needle sheath controller optionally can contain an outside grip for handling.

As shown in FIG. 3 and FIG. 7, the needle sheath controller 71' includes a controller housing 710 that encloses components internal to the needle sheath controller 71', and the proximal end of the needle sheath 72". As discussed above, the needle sheath controller housing 710 can be made of any suitably resilient and rigid material, such as any polymeric material, including plastics, or rubber, metals, ceramics, composites, or other suitable material known to one of skill in the art. The controller housing 710 is typically made of polypropylene, polystyrene, polyethylene, polyvinyl chloride, polyurethane, silicone, rubber or acrylic. As discussed above, the housing 710 can be made by any manufacturing known to a skilled artisan, and can be made as one singular piece or can be made of two or more pieces that are attached together, such as with adhesive, locking joints or fasteners.

As shown in FIG. 3 and FIG. 7, the needle sheath controller 71' contains an externally accessible positioner 711. As described above, the positioner 711 is configured in the needle sheath controller 71' so that it is movable both forward and rearward relative to the needle sheath controller 71'. As described above, the positioner 711 is engaged with the needle sheath 72" through a connection member 713, and can be used to slide the needle sheath 72". This connection permits movement of the positioner 711 between the forward or rearward positions to control movement of the needle sheath 72" between two fixed or locked positions, the sheathed and unsheathed positions. The sheathed position protects or hides the injection needle, while the unsheathed position exposes the needle.

With reference to FIG. 7, the connection member 713 is connected to the proximal end of the needle sheath 72", and the lower part of the positioner 711. The connection of the connection member 713 with the proximal end of the needle sheath is such that the needle sheath 72" is longitudinally movable relative to the controller housing 710 and the injection needle 81. For example, the distal end of the outside of the connection member 713 is engaged with the proximal inside lumen 723 of the needle sheath 72" around its circumference. The connections of the control member with the positioner 711 and needle sheath 72" can be by welding, adhesive, locking joints, fasteners or other suitable means.

As described above generally, the connection member 713 moves inside a hollow cavity or lumen 717 contained inside the housing 710 of the needle sheath controller 71' that is closed at both ends relative to the housing 710. The controller lumen 717 accommodates the connection member 713 such that the connection member 713 can easily glide or move forward or rearward in a restricted manner. For example, the connection member 713 can be cylindrical and fit inside a cylindrical hollow lumen cavity 717. As shown in FIG. 7, and discussed further below, the connection member 713 contains an internal hollow cavity sized to fit the plunger 92" that passes through.

Movement of the connection member 713 is controlled by the positioner 711. As shown in FIGS. 3 and 7, the positioner 711 contains a projected top portion or head that juts out of the needle sheath controller 71' where it can be moved forward or rearward by the operator. As shown in FIG. 7, internal to the needle sheath controller 71', the body of the positioner 711 is notched on its sides or is otherwise configured to engage with sheath stops 715 or 716. Sheath stops 715 and 716 are grooves in the needle sheath controller housing 710 that fit the notched body of the positioner and trap the positioner 711 so that it cannot be moved.

As exemplified in FIG. 5 with the exemplary device 60, device 60" also contains an optional lock and release element 712 configured in the positioner 711 to facilitate lock and release of the positioner with the grooves of the sheath stops 715 or 716. For example, the lock and release element 712 can be a spring or other resilient means. The mechanism controlling lock and release of the positioner 711 with the grooves of the sheath stops 715 or 716 by the lock and release element 712 is as described above, whereby downward, vertical or lateral forces release or lock the positioner 711 from the sheath stops 715 or 716. Pushing downward on the positioner 711 permits the positioner to slide and to fit it into either of sheath stops 715 or 716.

Movement of the positioner 711 between the sheath stops 715 and 716 moves the connection member 713, and thereby also moves the needle sheath 72" so that it can transition from the sheathed and unsheathed positions by control of the positioner by the operator. When the positioner is in the intermediate position as exemplified in FIG. 7, both distal sheath stop 715 and the proximal sheath stop 716 are free and not engaged with the positioner 711. While not shown in FIG. 7, the positioner 711 also can be in the forward position 711*a* as exemplified in FIG. 5, where the proximal sheath stop 716 is free and the positioner 711 is fit into the distal sheath stop 715, thereby sheathing the injection needle so that it is protected. As a further position, while not shown in FIG. 7, the positioner also can be in the rearward position 711*c* as shown in FIG. 6, where distal sheath stop 715 is free and the positioner 711 is fit into the proximal sheath stop 716, thereby unsheathing the injection needle so that it is exposed.

As shown in FIG. 7, the plunger 92" passes through the inside lumen 717 of the needle sheath controller 71' and passes through a central cavity of the connection member 713, but is not directly attached to the needle sheath controller 71' or connection member 713. Hence, the connection member 713 can move independently around the plunger 92", and the plunger 92" can move independently through the connection member 713. As discussed above, because the needle sheath 72" is directly connected to the connection member 713 contained in the controller lumen 717, the plunger 92" enters the inside cavity of the needle sheath 72" inside the needle sheath controller 71'. The plunger 92" exits the distal end of the needle sheath controller 71' where it is contained within the hollow cavity of the needle sheath 72".

Figure 11D:
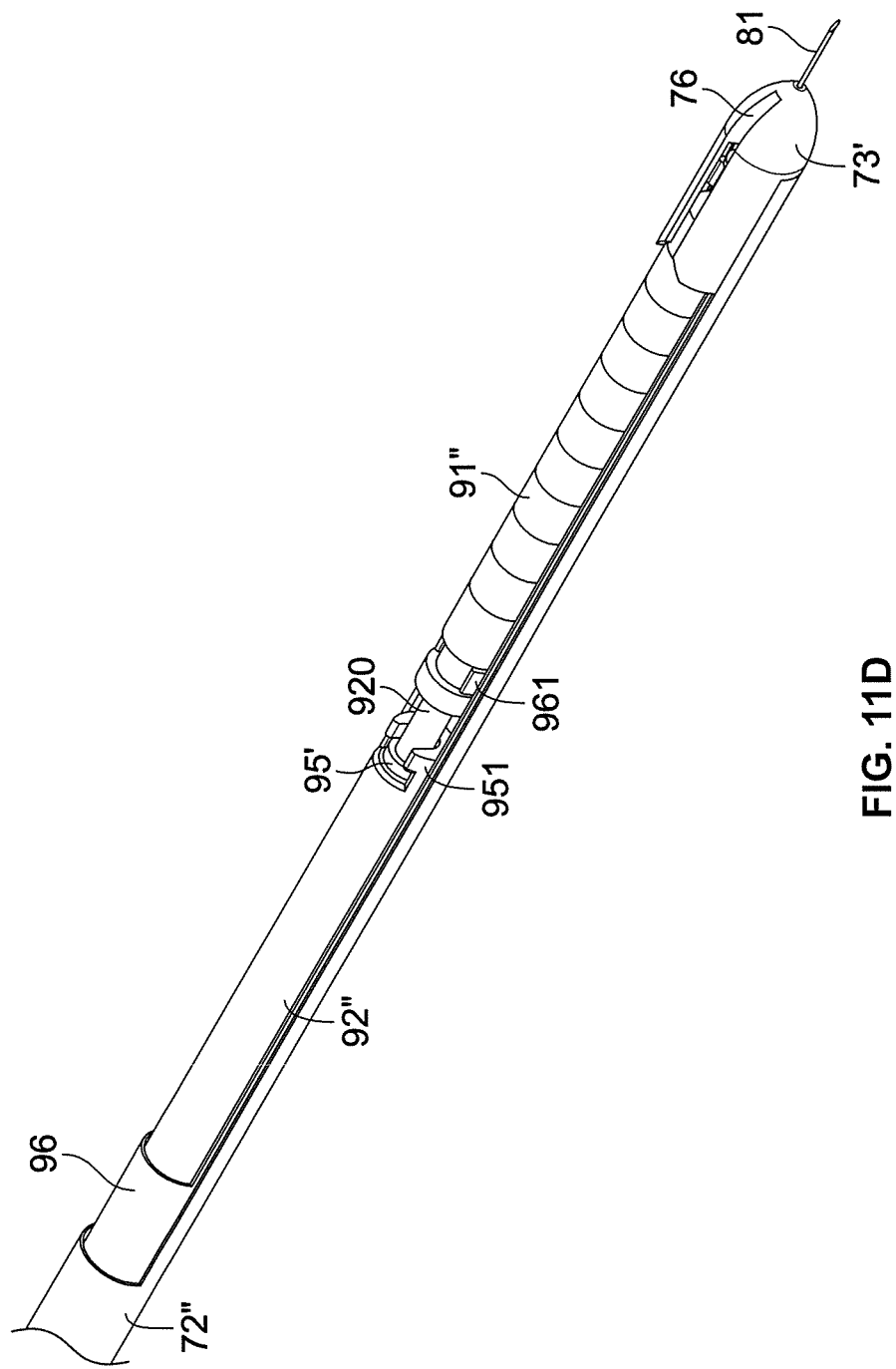

At the distal end of the device 60", the needle sheath 72" ends in a distal tip of the needle sheath 73' that contains a needle channel 733 that is sufficiently sized to fit injection needle 81. When the dockable syringe 910 is docked in the device in the docked position 910*b* as shown in FIGS. 11B-D, injection needle 81 fits through groove 76 where it is lined up to pass through needle channel 733 so that injection needle 81 can extend and retract through needle channel 733 as the needle sheath 72" moves. In FIG. 11B, injection needle 81 is fit into the groove 76 and contained in needle sheath 72", but does not traverse through the distal portion of needle channel 733. With reference to FIG. 4A, the device 60" in FIG. 11B is in the sheathed position 72*a*. In FIG. 11C, injection needle 81 is extended out of needle sheath 72" and does traverse through the distal portion through needle channel 733. With reference to FIG. 4C, the device 60" in FIG. 11C is in the unsheathed position.

As shown in FIGS. 11B and 11C, because syringe barrel 91" is not connected to needle sheath 72", the needle sheath 72" moves independently around syringe barrel 91". In the unsheathed position 72*c* as shown in FIG. 11C, the needle sheath 72" is pulled back, but the syringe barrel 91" and injection needle 81 are fixed and do not move. For example, as shown in FIG. 11C, because the needle sheath 72" is pulled back, the distal portion of the syringe barrel 91" is covered up by the distal tip of the needle sheath 73. In contrast, in the sheathed position 72*a* as shown in FIG. 11B, the sheath is not pulled back, such that the distal end of the syringe barrel 91" is not covered up by the distal tip of needle sheath 73. Hence, movement of the needle sheath 72" between sheathed and unsheathed positions, shortens the amount of syringe barrel 91" that is exposed in the docked cavity of device 60".

As described above, in the unsheathed position 72*c* as shown in FIG. 11C, the extent by which injection needle 81 is extended or exposed out of the device 60" is a function of the distance between sheath stops 715 and 716 as shown in FIG. 7 (and related FIGS. 5 and 6). This distance is a function of the particular application of the device, the particular target tissue, the subject being treated and other considerations. For example, unsheathed needle that is exposed should not be so long that it can easily penetrate through to the other side of a target tissue. Generally, with reference to most target tissues (e.g. liver), the portion of the injection needle 81 shown in FIG. 11C that can be unsheathed or exposed is generally less than 1 cm, such as 2 mm to 10 mm, and generally no more than 5 mm. For a child, the length can be smaller, and is generally less than 4 mm. For applications in utero, the length can be 2 mm to 3 mm. Generally, the total length of the injection needle 81 in device 60" is slightly longer than the unsheathed needle tip that can extend out of the device in the fully unsheathed position. As shown in FIG. 11C, the extent of the extra length is sufficient to account for the portion of the proximal end of the injection needle 81 still contained in the distal tip of sheath 73' and distal end of syringe barrel 91" when device is in the unsheathed position. For example, as described above, the total length of the injection needle 81 can range from 5 mm to 40 mm, such as 10 mm to 40 mm, such as a 12.7 mm, 25.4 mm or 38.1 mm needle.

Dispelling or ejecting a fluid, such as a therapeutic, or other solution through the injection needle is controlled by depressing plunger 92", which effects depression of auxiliary plunger 920 because of the connection achieved by plunger adaptor 951. With reference to FIG. 11C, plunger 92" is in an extended position, such that auxiliary plunger 920 also is in an extended position. In contrast, FIG. 11D illustrates plunger 92" in the depressed position, such that auxiliary plunger 920 also is in the depressed position. This allows the delivery of the fluid, such as a therapeutic, to the target tissue. The plunger 92" also can be used to control draw back of fluids from the injection site if drawback is required to test the needle placement. This is achieved by pulling or drawing back on plunger 92", which, through its connection with auxiliary plunger 920, also draws back auxiliary plunger 920. The drawback fluid can be visible in syringe barrel 91" where it is not covered by needle sheath 72".

The dockable syringe 910 (containing auxiliary plunger 920, syringe barrel 91" and injection needle 81) and/or the device 60" can be disposable or reusable. For example, after injection or exhaustion of the fluid, such as a therapeutic, from the syringe barrel 91", or when otherwise desirable, dockable syringe 910 can be withdrawn from the laparoscopic port. A newly loaded dockable syringe 910 can be docked into device 60". The newly loaded dockable syringe 910 can contain the previously used dockable syringe barrel 91" that can be re-loaded, or it can be new pre-loaded dockable syringe 910. Alternatively, the device 60" can be withdrawn from the laparoscopic port and disposed of after one use. In cases where sterile injections are required, the syringe barrel 91" can be loaded with the fluid, such as a therapeutic, in a sterile environment, such as a sterile operating room, and then docked into device 60". Alternatively, a sterile pre-loaded dockable syringe 910 can be used, which can be docked into device 60".

With reference to the above Figures and description, exemplary of the mode of operation of the injection device 60" involves first loading dockable syringe 910 with fluid, such as a therapeutic, prior to docking the syringe into the syringe adaptor in the syringe adaptor lining 96 located inside the needle sheath 72". Once the dockable syringe 910 is loaded, the syringe is docked into the syringe dock by engagement with barrel docks 961 and 963 and plunger adaptor 951. The needle sheath 72" can be positioned in the sheathed position 72a, and the device can be inserted into a laparoscopic port to be positioned close to the target site. At the site of injection (target tissue), the needle sheath 72" can be unsheathed 72c, and the injection needle 81 can be exposed for injection. If necessary, the control plunger 92" can be pulled back to draw fluids from the site of injection, for example, to test the placement of injection needle 81 at the injection site. The drawback fluid is visible at the distal end of syringe barrel 91" in needle sheath 72". The control plunger 92" can be depressed, to inject the fluid, such as a therapeutic, at the target tissue. After injection, the needle sheath 72" can be positioned in the sheathed position 72a, to protect the non-target organs and prevent accidental needle puncture, prior to removing the laparoscopic device from the injection site and through the laparoscopic port.

C. APPLICATIONS AND USES

The injection devices provided herein permits direct delivery of fluids, such as a therapeutic, into a specific target site, such as the parenchyma of an organ internal to the body of the subject, in minimally invasive procedures, such as surgeries, for example as laparoscopic surgeries. Accordingly, the injection device can be used in diverse applications, including, but not limited to, medical applications, including applications to exogenously administer a fluid, such as a therapeutic, for the treatment of a disease or condition, or other applications such as agricultural, veterinary and industrial applications that require direct delivery of a fluid to a target site in minimally invasive procedures. For example, the device can be used to deliver chemotherapeutic agents to a specific target organ, or the device can be used to deliver nucleic acids or viral agents to a specific organ targeted for gene therapy, without the need of invasive open surgery. In some examples, the injection device can be useful in delivering fluids, such as a therapeutic in settings where the fluid treats or ameliorates a disorder or condition in a subject or otherwise improves the quality of life in a subject. In other examples, the injection device can be useful in agricultural settings, for example, for applications that improve the quality or quantity of meat production.

The injection device can be used in any subject or patient that is in need of direct delivery of a fluid, such as a therapeutic, into a target site in a minimally invasive manner. Exemplary of such subjects include, but are not limited to, mice, rats, cows, pigs, sheep, goats, horses and humans. In particular examples, children under age 18, including infants, toddlers or young children, are contemplated herein for the delivery of fluids, such as therapeutics, for the treatment of diseases or conditions. In particular examples, in utero delivery of a fluid, such as a therapeutic, to the fetus is contemplated herein, for the treatment of diseases or conditions.

Exemplary applications of the method herein are provided below. It is understood that other applications exist depending on the particular fluid delivered, setting or subject. It is within the level of a person skilled in the art choose a fluid, setting, or subject of interest based on any desired application. The description herein below is for exemplification only.

1. Treating Diseases and Disorders

Provided herein are applications of treating a disease, disorder or condition by delivering a fluid, such as a therapeutic, directly into a target injection site in a subject using the injection device provided herein. The disease, disorder or condition that is treated is any that is amenable to treatment by an exogenously delivered fluid, such as a therapeutic, directly to the target site, such as the parenchyma of an internal organ of a subject. In any of such examples herein, the fluid, such as a therapeutic, is delivered directly and specifically to the target injection site during a minimally invasive procedure. Thus, provided herein is an injection device that is used to deliver an accurate amount of fluid to the target injection site of the subject in a minimally invasive procedure without accidental puncture of non-target sites or damage to the apparatuses used for minimally invasive procedures. The particular device used has an injection needle that when unsheathed also cannot puncture through the tissue or organ in which the direct injection is affected.

The fluid used for injection can be any fluid used for injection. In particular examples, the fluid contains a therapeutic used for treating a disease, disorder or a condition. The therapeutic can include a fluid comprising small molecule drugs, prodrugs, proteins, peptides, DNA, RNA, viruses, antibodies, organic molecules, saccharides, polysaccharides, lipids and combinations or conjugates thereof. In particular examples, the fluid can comprise a therapeutic including, but not limited to, a gene therapy agent, a chemotherapeutic agent, an analgesic agent, an anti-inflammatory agent, an antimicrobial agent, an amoebicidal agent, a trichomonocidal agent, an anti-parkinson agent, an antimalarial agent, an anticonvulsant agent, an anti-depressant agent, anantiarthritics agent, an anti-fungal agent, an anti-hypertensive agent, antipyretic agent, an anti-parasite agent, an antihistamine agent, an alpha-adrenargic agonist agent, an alpha blocker agent, an anesthetic agent, a bronchi dilator agent, a biocide agent, a bactericide agent, a bacteriostat agent, a betadrenergic blocker agent, a calcium channel blocker agent, a cardiovascular drug agent, a contraceptive agent, a decongestant agent, a diuretic agent, a depressant agent, a diagnostic agent, an electrolyte agent, a hypnotic agent, a hormone agent, a hyperglycemic agent, a muscle relaxant agent, a muscle contractant agent, an ophthalmic agent, a parasympathomimetic agent, a psychic energizer agent, a sedative agent, a sympathomimetic agent, a tranquilizer agent, a urinary agent, a vaginal agent, a viricide agent, a vitamin agent, a non-steroidal anti-inflammatory agent, an angiotensin converting enzyme inhibitor agent, an alcohol and a sleep inducer.

For example, the therapeutic can be a polypeptide, such as an enzyme, a hormone, a coagulation or clotting factor, a cytokine, a growth factor or active portion thereof, an antibody or antigen binding portions of antibodies, an angiogenesis modulator, an immunomodulator, a pain modulator, a receptor or active portion thereof, a transport protein, a regulatory protein, an antigen and an allergen.

In another example, the therapeutic can be a nucleic acid molecule for gene therapy, wherein the nucleic acid molecule encodes a polypeptide. The encoded polypeptide can include an enzyme, a hormone, a coagulation or clotting factor, a cytokine, a growth factor or active portion thereof, an antibody or antigen binding portions of antibodies, an angiogenesis modulator, an immunomodulator, a pain modulator, a receptor or active portion thereof, a transport protein, a regulatory protein, an antigen and an allergen. In a particular example, the polypeptides encoded can include adenosine deaminase, cystic fibrosis transmembrane conductance regulator (CTFR), galsulfase, laronidase, N-acetylgalactosamine 6-sulfatase, phenylalanine ammonia lyase, acid alpha glucosidase, imiglucerase, alglucosidase alpha, thyrotropin, growth hormone, insulin, thyroid hormone, erythropoietin (EPO), interleukin-1 (IL-1), IL-2, IL-3, IL-4, IL-5, IL-7, interferon-$\alpha$ (IFN-$\alpha$), IFN-$\beta$, IFN-$\gamma$, tumor necrosis factor (TNF), IL-12, IL-18, Fms-Related Tyrosine Kinase 3 (flt3), neuropilin-2 (NP2), bone morphogenic protein (BMPs), epidermal growth factor (EGF), erythropoietin (EPO), fibroblast growth factor (FGF), granulocyte colony stimulating factor (G-CSF), granulocyte macrophage colony stimulating factor (GM-CSF), hepatocyte growth factor (HGF), insulin-like growth factor (IGF), platelet derived growth factor (PDGF), transforming growth factor $\alpha$ or $\beta$, vascular endothelial growth factor (VEGF), epidermal growth factor receptor (EGFR), fibroblast growth factor receptor (FGFR), FGFR antagonist (sFGFR) transforming growth factor receptor (TGFR), vascular endothelial growth factor receptor (VEGFR), plasminogen activator, urokinase, Factor VIII, Factor IX, von Willebrand factor, growth hormone, metalloproteinase thrombospondin motifs 1 (METH-1), METH-2, tryptophanyl-tRNA synthetase (TrpRS) fragments, proliferin-related protein, prolactin fragment, pigment epithelium-derived factor (PEDF), vasostatin, angiostatin, endostatin, kininostatin, fibrinogen-E fragment, thrombospondin, tumstatin, canstatin, restin, soluble fms-like tyrosine kinase-1 (sFlt-1), soluble vascular endothelial growth factor receptors (sFlk), soluble Neuropilin 1 (sNRP1), Interferon gamma-induced protein 10 (IP-10), Platelet factor 4 (PF-4), Gro-beta, soluble Ephrin type-B receptor 4 (sEphB4), sephrinB2, IGF-1, herpes simplex virus thymidine kinase (HSV-TK), carboxypeptidase G2 (CPG2), carboxylesterase (CA), cytosine deaminase (CD), cytochrome P450 (cyt-450), deoxycytidine kinase (dCK), nitroreductase (NR), purine nucleoside phosphorylase (PNP), thymidine phosphorylase (TP), varicella zoster virus thymidine kinase (VZV-TK), xanthine-guanine phosphoribosyl transferase (XGPRT), Aspartylglucosaminidase, $\alpha$-Galactosidase A, Palmitoyl Protein Thioesterase, Tripeptidyl Peptidase, Lysosomal transmembrane protein, cysteine transporter, Acid ceramidase, acid $\alpha$-L-fucosidase, protective protein/cathepsin A, acid $\beta$-glucosidase or glucocerebrosidase, acid $\beta$-galactosidase, iduronate-2-sulfatase, $\alpha$-L-Iduronidase, galactocerebrosidase, acid $\alpha$-mannosidase, acid $\beta$-mannosidase, arylsulfatase B, arylsulfatase A, N-Acetylgalactosamine-6-sulfate sulfatase, N-Acetlylglucosamine-1-phosphotransferase, Acid sphingomyelinase, Niemann-Pick disease, type C1 (NPC-1), $\beta$-Hexosaminidase B, Heparan N-sulfatase, $\alpha$-N-Acetylglucosaminidase (Na-Glu), Acetyl-CoA:aglucosamininde N-acetyltransferase, N-Acetylglucosamine-6-sulfate sulfatase, $\beta$-Glucuronidase, acid lipase, neprilysin, the insulin-degrading enzyme insulysin, thimet oligopeptidase, calbindin D28, parvalbumin, hypoxia induced factor 1-alpha (HIF1-alpha), sirtuin-2 (SIRT-2), survival motor neuron protein-1 (SMN-1), SMN-2, glial cell-derived neurotrophic factor (GDNF), ciliary neurotrophic factor (CNF), low density lipoprotein receptor (LDLR), lipoprotein lipase (LPL), Alpha-1-Antitrypsin (AAT), UDP-glucuronyl-transferase (UGT), UGT1A1, glucose-6 phosphatase, phosphoenolpyruvate-carboxykinase, galactose-1 phosphate uridyl transferase, phenylalanine hydroxylase, branched chain alpha-ketoacid dehydrogenase, fumarylacetoacetate hydrolase, methylmalonyl-CoA mutase, ornithine transcarbamylase, argininosuccinic acid synthetase, adenosine deaminase, hyposanthine guanine phosphoribosyl transferase, biotinidase, beta-glucocerebrosidase, beta-glucuronidase, porphobilinogen deaminase (PBDG) and p53.

For example, diseases or conditions for which the injection device provided herein can be used include any in which treatment is effected by increasing or decreasing the activity of a specific protein or other cellular targets, decreasing or increasing expression of a gene associated with the condition, decreasing or increasing the activity of a gene product associated with the condition or otherwise countering the alteration associated with the condition (e.g. signs, symptoms or effects associated with the disease or condition), by direct delivery of the therapeutic to a target organ. For example, nonspecific or targeted chemotherapeutic agents can be delivered directly and specifically to the parenchyma of a solid tumor to kill rapidly dividing cells. The diseases or conditions for which the injection device provided can be used for include an arthritis, chronic pain, HIV-related AIDS, atherosclerosis, restenosis, inherited enzyme deficiency, inherited immune deficiency, cancer, a retrovirus infection, hemophilia, diabetes, a muscular dystrophy, a cardiovascular disorder, cystic fibrosis, a neurodegenerative disorder, trauma, pain, sickle cell anemia, autoimmune disease, inflammatory disease, and hypertension.

In another example, the device can be used to deliver fluids that include gene therapy agents, such as nucleic acids, vectors or viruses. Gene therapy can be used to treat diseases or conditions associated with genetic deficiencies, including monogenic diseases, (e.g. hemophilia A and B, type I diabetes mellitus, alpha-1-antitrypsin (AAT), cystic fibrosis, muscular dystrophy and numerous others) or can be used to treat diseases or conditions by encoding a therapeutic protein associated with ameliorating the disease or condition (e.g. cancers).

The injection device provided herein can be used in methods to inject a wide variety of fluids in medical applications. The delivered fluid, and the therapeutic agent therein, is selected based on the disorder or disease to be addressed, and the particular organ affected. As described elsewhere herein, one of skill in the art can determine the type of therapeutic agent depending on the particular disease or disorder that is being treated. As further exemplification, the injection device can be used to deliver anti-angiogenesis agents, such as angiostatin or endostain for the treatment of cancer, insulin for the treatment of diabetes mellitus, soluble tumor necrosis factor (TNF) receptor for the treatment of rheumatoid arthritis, angiostatin for the treatment of renal failure, anti-human immunodeficiency virus (HIV) agents for the treatment of HIV infection and acquired immunodeficiency syndrome (AIDS), ethanol for the treatment of papillary thyroid carcinoma (PTC), and Factor VIII or Factor IX for hemophilia. The therapeutic agents can also be in the form of nucleic acids that encode a protein required to ameliorate the disease symptoms or treat the disease. In other examples, the injection device can be used to deliver a nucleic acid encoding a Factor VIII for the treatment of hemophilia A; a Factor IX for the treatment of hemophilia B; an insulin gene for treatment of type I diabetes mellitus; an alpha-1-antitrypsin (AAT) for the treatment of alpha-1-antitrypsin (AAT) deficiency; a hemochromatosis protein (HFE) for treatment of hemochromatosis; a copper-transporting ATPase 2 for treatment of Wilson's disease; UDP glucuronosyltransferase 1A1 (UGT1A1) for the treatment of Crigler-Najjar syndrome type I; ornithine transcarbamylase (OTC) for the treatment of ornithine transcarbamylase deficiency, type II; low density lipoprotein receptor (LDLR) for the treatment of familial hypercholesterolemia; fibrinogen alpha (FGA), beta (FGB) or gamma (FGB) for the treatment of afibrinogenemia; glucose-6-phosphate-$\alpha$ for the treatment of glycogen storage disease (GSD) type Ia; G6PT for the treatment of GSD type Ib; acid-$\alpha$-glucosidase for the treatment of GSD type II (Pompe); $\alpha$-L-iduronidase for the treatment of mucopolysaccharidosis (MPSI); sulphamidase for the treatment of MPS IIIA; $\alpha$-N-acetylglucosaminidase (NaGlu) for the treatment of MPS IIIB; $\beta$-glucuronidase for the treatment of MPS VII; $\alpha$-galactosidase A for the treatment of Fabry disease; glucocerebrosidase for the treatment of Gaucher's disease; acid sphingomyelinase for the treatment of Niemann-Pick syndrome; phenylalanine hydroxylase for the treatment of phenylketonuria; TIMP antagonist or anti-HSC molecules for the treatment of liver fibrosis; anti-ROS molecules for the treatment of liver ischemia reperfusion injury; amyloid-beta degrading enzyme neprilysin, the insulin-degrading enzyme insulysin, or thimet oligopeptidase for the treatment of Alzheimer's disease; insulin growth factor-1 (IGF-1), calbindin D28, parvalbumin, HIF1-alpha, SIRT-2, VEGF, SMN-1, SMN-2, GDNF or ciliary neurotrophic factor (CNF) for the treatment of Amyotrophic Lateral Sclerosis (ALS); galactose-1 phosphate uridyl transferase for the treatment of galactosemia; branched chain alpha-ketoacid dehydrogenase for the treatment of maple syrup urine disease; fumarylacetoacetate hydrolase for the treatment of tyrosinemia type 1; methylmalonyl-CoA mutase for the treatment of methylmalonic acidemia; argininosuccinic acid synthetase for the treatment of citrullinemia; hyposanthine guanine phosphoribosyl transferase for the treatment of Gout and Lesch Nyan syndrome; beta-glucuronidase for the treatment of Sly syndrome; peroxisome membrane protein 70 kDa for the treatment of Zellweger syndrome, enfuvirtide for the treatment of Human immunodeficiency virus (HIV) infection; adenosine deaminase (ADA) for the treatment of combined immunodeficiency disease (SCID); cystic fibrosis transmembrane conductance regulator (CFTR) for the treatment of cystic fibrosis; porphobilinogen deaminase (PBDG) for the treatment of acute intermittent *porphyria*; interferon-beta for the treatment of multiple sclerosis; lipoprotein lipase for the treatment of lipoprotein lipase deficiency (LPLD), p53 for the treatment of cancer; glutamic acid decarboxylase (GAD) for the treatment of Parkinson's Disease; neuropilin-2 (NP2) for treatment of pain; a nucleic acid encoding an angiogenesis inhibitor or tumor suppressor for the treatment of cancer; and a nucleic acid encoding an insulin or exendin-4 for treatment of diabetes.

Further, it is known to one of skill in the art the particular target tissue or organ for direct injection of the fluid based on the disease or disorder to be treated, and the particular delivered therapeutic agent that is administered. In some cases, the delivered fluid such as a therapeutic does not exhibit specific tissue targeting when systemically administered, and thus is delivered directly to the affected target site, such as a tissue or an organ.

For specific target tissues or organs for delivery of fluids, such as a therapeutic, the lung is an important target organ for direct injection of therapeutics to treat or ameliorate many acute and chronic diseases, including cancer, asthma, cystic fibrosis, alpha-1-antitrypsin deficiency and respiratory distress syndrome, among others. The muscle is a target organ for direct injection of therapeutics for treatment of muscular or motor disorders like muscular dystrophy or charcot-Marie-Tooth (CMT) disease. The brain is an important target organ for direct injection of therapeutics of motor neuron diseases (e.g. spinal muscular atrophy (AMA), amyotrophic lateral sclerosis (ALS), X-linked adrenoleukodystrophy (ALD)), Parkinson's Disease, or diseases and conditions associated with a missing or defective gene, including metabolic or lysosomal disorders such as Sanfilippo (mucopolysaccharaidosis type III; MSPIII) or Canavan disease. The skin is a target organ for direct injection of therapeutics for chronic wounds, hypertrophic scars, keloids, cancer, genetic diseases and systemic diseases. The liver is a target organ for direct injection of therapeutics of numerous liver diseases and disorders including, but not limited to, hemochromatosis, hemophilia A and B, alpha 1 antitrypsin deficiency, Wilson's disease, Crigler-Najjar syndrome type I, ornithine transcarbamylase deficiency, type IIa familial hypercholesterolemia, afibrinogenemia, lysosomal storage diseases, glycogen storage diseases, phenylketonuria, Tay-Sachs disease, induced hepatitis.

This list is not intended to be limiting, as any disease or condition that can be addressed with a therapeutic agent that is directly and specifically delivered to a target injection site could be addressed. Exemplary methods of treating various diseases and conditions are described below.

D. EXAMPLES

The following examples are included for illustrative purposes only and are not intended to limit the scope of the invention.

Example 1

Construction of Syringe Injection Device

A syringe injection device 60 of the type depicted in FIGS. 1A, 1B, 5, 8A-B and 9A-D and as described in the detailed description was constructed. The device contains a plunger 92 and syringe barrel 91, a needle sheath controller 71, a needle sheath 72, and an injection needle 81. The device was configured so that a standard 1 cc syringe barrel 91 containing plunger 92, but without needle, is able to be separately attached to needle sheath controller 71. To permit laparoscopic access to a portion of the liver, the diameter of the needle sheath 72 was 5 mm and the length of the needle sheath 72 was 300 mm (see e.g. FIG. 1A showing syringe barrel removed from needle sheath controller, position 900a, and FIG. 1B showing syringe barrel attached to needle sheath controller, position 900*b*).

As constructed, when the syringe barrel 91 is connected to the needle sheath controller 71, the injection needle 81 is connected to syringe barrel 91 via an injection tube 83. The injection needle was a standard 27 gauge of 10 mm in length and was connected directly to a 27 gauge injection tube 83. The injection tube 83 and injection needle 81 were made of stainless steel. The injection tube 83 contained a needle hub 84 at proximal end, and the injection tube 83 and needle hub 84 were directly affixed to needle sheath controller 71 at the proximal end of the inside of the needle sheath controller 71 (see e.g. FIGS. 1A and 1B).

A standard 1 cc insulin syringe containing a syringe barrel 91 and plunger 92, but without a needle, was filled with 0.7 mL solution and purged. The syringe was attached to the proximal end of the needle hub 84 outside of the needle sheath controller 71 using a Luer fit adaptor 93 (see FIGS. 1A and 1B). The injection needle 81 was sheathed and locked by sliding the positioner 711 forward.

Example 2

Compartmentalized Transduction of the Liver in a Laparoscopic Simulator

A clamp device and the injection device 60 described in Example 1 were utilized in a laparoscopic simulator by a skilled surgeon/physician to effect clamping of a portion of the left median lobe of a liver to compartmentalize the region for delivery of an injectable solution. The laparoscopic simulator (Lapa-Pro, Mexico) was positioned at a 35° to 45° angle inclination to simulate the Semi-Fowlers position of a subject. The Semi-Fowlers position facilitates the access to the distal portion of the left lobe of the human liver using gravity to distally displace the abdominal organs. With respect to a subject, the entry ports of the simulator were positioned as follows: one entry port in the epigastric abdominal region; one entry port in the umbilical abdominal region; and two entry ports in the left lumbar abdominal region.

A freshly obtained cadaveric pig liver was positioned inside the laparoscopic simulator. The laparoscope was inserted through the umbilical entry port. A laparoscopic clamp was inserted through the epigastric entry port and was used to clamp a 5 cm portion of the distal portion of the left median lobe of the cadaveric pig liver.

A standard 1 cc insulin syringe was filled with 0.7 mL tap water solution and purged. The filled syringe containing a syringe barrel 91 and plunger 92 was attached to a needle hub 84 on the proximal end of the needle sheath controller 71 as depicted in FIG. 1B. The positioner 711 on the needle sheath controller 71 was slid backward to unlock the positioner 711 and to unsheathe the injection needle 81. The entire syringe injection device was purged by pressing the plunger until fluid was observed at the tip of the needle (approximately 200 μL). The positioner 711 on the needle sheath controller 71 was then slid forward to lock the positioner 711 in the forward position 711*a* and to sheathe the the injection needle 81. The injection device with the needle sheathed was introduced into the simulator through the proximal left lumbar entry port. Using the laparoscope monitor, the tip of the injection device was positioned close to the site of injection. The injection needle 81 on the injection device was unsheathed by sliding the positioner 711 backward and locking the positioner in the rearward position 711*c*. The tip of the injection needle 81 was introduced into the parenchymal tissue making sure that it did not go through the tissue. Once the tip of the injection needle 81 was carefully positioned inside the parenchyma, the plunger 92 was pressed until 500 μL of fluid was injected.

The positioner 711 on the needle sheath controller 71 was slid forward to lock the positioner 711 in the forward position 711*a* and to sheathe the needle. The injection device 60 was removed from the simulator. The clamp also was released from the liver. Once released, the procedure was over, and the clamp also was removed from the simulator.

Since modifications will be apparent to those of skill in the art, it is intended that this invention be limited only by the scope of the appended claims.

The invention claimed is:

1. An injection device, comprising:
   a) a syringe barrel, wherein the syringe barrel provides a fluid reservoir;
   b) a plunger configured to be controlled by the operator of the device and to move within the syringe barrel for loading and releasing fluid from the fluid reservoir in the syringe barrel;
   c) an injection needle that is fixed and operably coupled to the syringe barrel providing a fluid pathway for fluid contained in the syringe barrel to be injected into a target tissue when the plunger is depressed, wherein extraction or retraction of the needle is independent of movement of the plunger;
   d) an elongate sheath, comprising an internal lumen that contains the injection needle and having a distal tip that contains an opening for the injection needle, wherein: the sheath is movable around the injection needle; and control of the sheath is independent from movement of the plunger; and
   e) a controller for positioning the sheath, comprising:
      a housing, comprising at least a first and second stop to control exposure of the injection needle and that are provided within the housing at a predetermined distance from each other, wherein the stops can be locked;
      a central lumen in the housing comprising a connection member, wherein the connection member is configured to be movable in the central lumen in the housing and is coupled to the sheath, wherein the proximal end of the sheath is coupled to the distal end of the connection member so that movement of the connection member controls movement of the sheath; and
      a positioner mounted within the housing configured to move forward towards the distal end of the controller and rearward towards the proximal end of the controller, between the stops in the housing, wherein the positioner comprises a lock and release element that is configured in the positioner to engage the positioner with the stops, and is operatively connected to the connection member to guide movement of the connection member in the same direction, whereby movement of the positioner forward towards the distal end engages the first stop and moves the sheath to enclose the injection needle inside the lumen of the sheath, and movement of the positioner rearward towards the proximal end engages the second stop and moves the sheath to expose no more than a predetermined length of the distal tip of the injection needle through the opening for the injection needle for injection into the tissue.

2. The injection device of claim 1, wherein the elongate sheath is of a sufficient length and width to reach an organ through an endoscopic port.

3. The injection device of claim 1, wherein the elongate sheath has a length from its proximal to distal end of from about 200 mm to 600 mm and a diameter of from about 2 mm to 15 mm.

4. The injection device of claim 1, wherein the predetermined length of the distal tip of the injection needle that is exposed is 1 mm to 10 mm.

5. The injection device of claim 1, comprising at least 3 stops, 4 stops or 5 stops, wherein:
the second stop is the most proximal stop and the first stop is the most distal stop and the other stop or stops are positioned between the first stop and the second stop; and
each stop is positioned at a predetermined distance from the adjacent stop or stops to control exposure of the needle to different predetermined lengths, wherein the second stop controls exposure of the needle to its longest predetermined length, whereby the positioner can move between the adjacent stops to engage with the stop to expose different predetermined lengths of the injection needle.

6. The injection device of claim 1, wherein the predetermined distance between stops is substantially the same as the predetermined length of the exposed injection needle.

7. The injection device of claim 1, wherein the lock and release element is a spring that provides an upward force against the positioner and a downward force against the connection member to lock the positioner into the stop, and is capable of being compressed to release the positioner from the stop.

8. The injection device of claim 1, wherein the injection needle is 5 mm to 40 mm in length.

9. The injection device of claim 1, wherein the injection needle is 25 gauge to 34 gauge, 25 gauge to 30 gauge or 26 gauge to 28 gauge.

10. The injection device of claim 1, wherein the syringe barrel is proximal or distal to the controller.

11. The injection device of claim 10, wherein the syringe barrel is proximal to the controller and is operably coupled to the injection needle by an injection tube, wherein:
the injection tube comprises a proximal and a distal end, the proximal end connected to the syringe barrel and the distal end connected to the injection needle; and
the controller is configured to hold the injection tube and comprises an opening at the proximal end so that the injection tube is operably connected to the syringe barrel.

12. The injection device of claim 11, wherein the syringe barrel is configured to be connected to the injection tube so that the syringe barrel is detachable from the device.

13. The injection device of claim 12, wherein the injection tube comprises a hub on its proximal end that is compatible with an adaptor on the distal end of the syringe barrel and the hub of the injection tube connects to the adaptor of the syringe barrel.

14. The injection device of claim 11, wherein:
the injection tube is fixed in the controller;
the connection member in the controller comprises a recess by which the injection tube is routed to pass from the controller into the sheath at the junction where the connection member is coupled to the sheath; and
the connection member is movable around the injection tube.

15. The injection device of claim 11, wherein the injection tube is connected directly to the injection needle.

16. The injection device of claim 11, wherein the injection tube is connected indirectly to the injection needle via a coupler, the coupler having a proximal and distal end, the proximal end connected to the distal end of the injection tube and the distal end connected to the proximal end of the injection needle.

17. The injection device of claim 16, wherein:
the sheath is opaque;
the coupler is transparent; and
the sheath comprises a window configured in the sheath to view the coupler.

18. The injection device of claim 11, wherein the injection tube and injection needle are different gauges.

19. The injection device of claim 18, wherein:
the injection tube has a larger diameter than the injection needle;
the injection needle is 25 gauge to 34 gauge; and
the injection tube is 15 gauge to 25 gauge.

20. The injection device of claim 11, wherein the injection tube and injection needle are the same gauge.

21. The injection device of claim 1, wherein:
the injection needle is operably coupled to the syringe barrel by an injection tube, the injection tube comprises a proximal and a distal end, the proximal end connected to the syringe barrel and the distal end directly or indirectly connected to the injection needle;
the injection needle is 25 gauge to 34 gauge and has a length in the range from 5 mm to 40 mm;
the injection tube has a larger diameter than the injection needle, wherein the injection needle has a diameter less than 25 gauge; and
the controller is distal to the syringe barrel and plunger and comprises a cavity for the injection tube and an opening at the proximal end so that the injection tube extends out of the controller to connect to the syringe barrel, wherein the injection tube is fixed in the controller;
the connection member in the central lumen of the housing of the controller comprises a recess by which the injection tube is routed to pass from the controller into the distal lumen of the sheath at the junction where the connection member is coupled to the sheath; and
the connection member is configured to be movable in the central lumen in the housing around the injection tube.

22. The injection device of claim 1, wherein:
the syringe barrel is positioned distal to the controller and the internal lumen of the sheath comprises the syringe barrel in its distal end; and
the syringe barrel is configured in the lumen so that the sheath is movable around the syringe barrel.

23. The injection device of claim 22, wherein the sheath comprises an open cavity that comprises the syringe barrel.

24. The injection device of claim 23, wherein:
the open cavity of the sheath comprises a lining that is configured in the sheath so that the sheath is movable around the lining; and
the syringe barrel is mounted into the lining in the open cavity.

25. The injection device of claim 23, wherein the plunger is operably connected to the syringe barrel in the distal end of the lumen of the sheath and arranged so that the plunger is movable through the controller and within the lumen of the sheath.

26. The injection device of claim 25, wherein;
the plunger is operably connected to the syringe barrel by an auxiliary plunger provided in the lumen of the sheath; and
the plunger is adapted to couple with the auxiliary plunger in the lumen of the sheath and arranged so that the plunger is movable through the controller and sheath and the auxiliary plunger is movable through the sheath and configured to move within the syringe barrel, whereby depressing the plunger depresses the auxiliary plunger into the syringe barrel releasing fluid from the fluid reservoir in the syringe barrel and pulling back on the plunger pulls back on the auxiliary plunger to load fluid into the fluid reservoir in the syringe barrel.

27. The injection device of claim 26, wherein the plunger comprises an adaptor at its distal end to connect to the proximal end of the auxiliary plunger.

28. The injection device of claim 26, wherein:
the open cavity of the sheath comprises a detachable syringe; and
the detachable syringe comprises the syringe barrel, the auxiliary plunger having a distal end configured to be movable in the syringe barrel and a proximal end coupled to the plunger, and the injection needle that is operably coupled to the syringe.

29. The injection device of claim 28, wherein the open cavity of the sheath comprises a lining that is configured in the sheath so that the sheath is movable around the lining; and
the detachable syringe is mounted into the lining in the open cavity.

30. The injection device of claim 22, wherein the plunger is longer than the sheath and has a length that is from or from about 100 mm to 600 mm or 200 mm to 500 mm.

31. The injection device of claim 22, wherein the controller is configured to hold the plunger so that the plunger is movable within the controller, the controller comprising:
an opening at its proximal end to receive the plunger; and
a recess in the connection member of the controller by which the plunger is routed to pass from the controller into the lumen of the sheath at the junction where the connection member is coupled to the sheath, wherein the plunger and connection member move independently with respect to each other.

32. The injection device of claim 22, wherein:
the device further comprises an extended plunger configured to be controlled by the operator of the device and coupled to an auxiliary plunger to move within the syringe barrel for loading and releasing fluid from the fluid reservoir in the syringe barrel, whereby depressing the plunger depresses the auxiliary plunger into the syringe barrel releasing fluid from the fluid reservoir in the syringe barrel and pulling back on the plunger pulls back on the auxiliary plunger to load fluid into the fluid reservoir in the syringe barrel;
the injection needle is 25 gauge to 34 gauge and has a length in the range from 5 mm to 40 mm;
the internal lumen of the sheath further contains the plunger and the auxiliary plunger;
the sheath is enclosed at its proximal end and provides a conduit for the plunger, wherein the plunger is movable through the sheath;
the sheath comprises an open cavity at the distal end, the open cavity comprising the auxiliary plunger, syringe barrel and injection needle, wherein:
the open cavity of the sheath comprises a lining that is configured in the sheath so that the sheath is movable around the lining;
the auxiliary plunger, syringe barrel and injection needle are mounted into the lining in the open cavity; and
the auxiliary plunger, syringe barrel and injection needle are detachable as a unit from the open cavity;
the sheath is movable around the plunger, auxiliary plunger, syringe barrel and injection needle;
the controller comprises an opening at its proximal end to receive the plunger and a cavity configured to hold the plunger so that the plunger is movable within the controller; and
the connection member comprises a recess by which the plunger is routed to pass from the controller into the distal lumen of the sheath at the junction where the connection member is coupled to the sheath, wherein the plunger and connection member move independently with respect to each other.

33. The injection device of claim 22, wherein:
the device further comprises an extended plunger configured to be controlled by the operator of the device to move within the syringe barrel for loading and releasing fluid from the fluid reservoir in the syringe barrel;
the injection needle is 25 gauge to 34 gauge and has a length in the range from 5 mm to 40 mm;
the internal lumen of the sheath further contains the plunger;
the sheath is enclosed to provide a conduit for the plunger, wherein the plunger is movable through the sheath;
the sheath comprises a window to view the syringe barrel;
the sheath is movable around the plunger;
the controller comprises an opening at its proximal end to receive the plunger and a cavity configured to hold the plunger so that the plunger is movable within the controller; and
the connection member comprises a recess by which the plunger is routed to pass from the controller into the distal lumen of the sheath at the junction where the connection member is coupled to the sheath, wherein the plunger and connection member move independently with respect to each other.

34. The injection device of claim 22, wherein the sheath encloses the syringe barrel.

35. The injection device of claim 34, wherein the sheath comprises a window to view the syringe barrel.

36. The injection device of claim 1 for delivering a therapeutic to an organ or tissue.

37. The injection device of claim 36, wherein the therapeutic is a biologic, chemotherapeutic or gene therapy agent.

38. The injection device of claim 36, wherein the therapeutic is a small molecule drug, prodrug, protein, peptide, DNA, RNA, virus, antibody, organic molecule, saccharide, polysaccharide, lipid and combinations or conjugates thereof.

39. A method of directly administering a fluid to a tissue or an organ in a subject during a minimally invasive procedure, comprising:
inserting the injection device of claim 1 into a port or cannula configured to provide access to the tissue or organ during the minimally invasive procedure; and
depressing the plunger to inject the fluid into the tissue.

40. The method of claim 39, wherein the subject is selected from among a mouse, rat, dog, cow, pig, sheep, goat, horse and human.

41. The method of claim 39, further comprising removing the device from the port.

42. The method of claim 41, wherein prior to removing the device from the port, moving the positioner forward towards the distal end to engage with the first stop to move the sheath to enclose the injection needle inside the lumen of the sheath.

43. The method of claim 39, wherein:
the device is provided for inserting into the port with the positioner moved forward towards the distal end to engage with the first stop to move the sheath to enclose the injection needle inside the lumen of the sheath; and
prior to depressing the plunger, the positioner is moved rearward toward the proximal end to engage the second stop to move the sheath to expose the injection needle.

44. The method of claim 39, wherein the tissue or organ is selected from among a liver, brain, spinal cord, pancreas, heart, skin, kidney, lung, blood vessel, bone, muscle, uterus, cervix, prostate, urethra, and intestine.

45. The method of claim 39, wherein the fluid is a composition comprising a therapeutic.

46. The method of claim 45, wherein the therapeutic is a biologic, chemotherapeutic or gene therapy agent.

47. The method of claim 45, wherein the composition is a pharmaceutical composition.

48. The method of claim 45, wherein the therapeutic is a small molecule drug, prodrug, protein, peptide, DNA, RNA, virus, antibody, organic molecule, saccharide, polysaccharide, lipid and combinations or conjugates thereof.

49. The method of claim 45, wherein the therapeutic is a nucleic acid molecule for gene therapy, and the nucleic acid molecule encodes a polypeptide.

50. The method of claim 49, wherein the nucleic acid molecule is a therapeutic nucleic acid molecule that encodes a therapeutic product, whereby delivery of the nucleic acid molecule effects treatment of a disease or condition.

51. The method of claim 49, wherein the nucleic acid molecule is delivered in a vehicle selected from among a lipid vesicle, a virus and a microorganism.

52. The injection device of claim 1, wherein:
the controller for positioning the sheath comprises at least three stops, wherein:
the second stop is the most proximal stop, and the first stop is the most distal stop and the other stop or stops are positioned between the first stop and the second stop; and
each stop is positioned at a predetermined distance from the adjacent stop or stops to control exposure of the injection needle to different predetermined lengths, wherein the second stop controls exposure of the injection needle at its longest predetermined length, whereby the positioner can move between the adjacent stops to engage with the stop to expose different predetermined lengths of the injection needle; and
the positioner comprises a lock and release element that is a spring that provides an upward force against the positioner and a downward force against the connection member to lock the positioner into the stop, and is capable of being compressed to release the positioner from the stop.

* * * * *

UNITED STATES PATENT AND TRADEMARK OFFICE
CERTIFICATE OF CORRECTION

PATENT NO. : 10,245,388 B2
APPLICATION NO. : 14/455865
DATED : April 2, 2019
INVENTOR(S) : Cabrera Aquino et al.

Page 1 of 2

It is certified that error appears in the above-identified patent and that said Letters Patent is hereby corrected as shown below:

In the Specification

At Column 10, Line 5, please replace "Acetyl-CoA:αglucosamininde" with —Acetyl-CoA:αglucosaminide—;

At Column 12, Line 3, please replace "$1\times10^{12}\pm1\times10^{6}$" with —$1\times10^{12}$ pfu, $1\times10^{6}$—;

At Column 60, Line 9, please replace "Acetyl-CoA:aglucosamininde" with —Acetyl-CoA:αglucosaminide—.

In the Claims

At Column 66, Lines 23-46, please replace Claim 21 with the following amended claim:
—21. The injection device of claim 1, wherein:
    the injection needle is operably coupled to the syringe barrel by an injection tube, the injection tube comprises a proximal and a distal end, the proximal end connected to the syringe barrel and the distal end directly or indirectly connected to the injection needle;
    the injection needle is 25 gauge to 34 gauge and has a length in the range from 5 mm to 40 mm;
    the injection tube has a larger diameter than the injection needle, wherein the injection needle has a diameter less than 25 gauge;
    the controller is distal to the syringe barrel and plunger and comprises a cavity for the injection tube and an opening at the proximal end so that the injection tube extends out of the controller to connect to the syringe barrel, wherein the injection tube is fixed in the controller;
    the connection member in the central lumen of the housing of the controller comprises a recess by which the injection tube is routed to pass from the controller into the distal lumen of the sheath at the junction where the connection member is coupled to the sheath; and
    the connection member is configured to be movable in the central lumen in the housing around the injection tube.—;

Signed and Sealed this
Sixteenth Day of July, 2019

Andrei Iancu
*Director of the United States Patent and Trademark Office*

CERTIFICATE OF CORRECTION (continued)
U.S. Pat. No. 10,245,388 B2

At Column 68, Lines 52-56, please replace Claim 38 with the following amended claim:
—38. The injection device of claim 36, wherein the therapeutic is a small molecule drug, prodrug, protein, peptide, DNA, RNA, virus, antibody, organic molecule, saccharide, polysaccharide, lipid, and combinations or conjugates thereof.—;

At Column 69, Lines 26-29, please replace Claim 48 with the following amended claim:
—48. The method of claim 45, wherein the therapeutic is a small molecule drug, prodrug, protein, peptide, DNA, RNA, virus, antibody, organic molecule, saccharide, polysaccharide, lipid, and combinations or conjugates thereof.—.